(12) United States Patent
Mitchell et al.

(10) Patent No.: US 8,048,121 B2
(45) Date of Patent: *Nov. 1, 2011

(54) SPINE IMPLANT WITH A DEFELCTION ROD SYSTEM ANCHORED TO A BONE ANCHOR AND METHOD

(75) Inventors: Steven T. Mitchell, Concord, CA (US); Charles J. Winslow, Walnut Creek, CA (US); John J. Flynn, Walnut Creek, CA (US); James F. Zucherman, San Francisco, CA (US); Ken Y. Hsu, San Francisco, CA (US); Donald L. Cain, Oakland, CA (US); Henry A. Klyce, Piedmont, CA (US); H. Adam R. Klyce, Berkeley, CA (US)

(73) Assignee: Spartek Medical, Inc., Alameda, CA (US)

( * ) Notice: Subject to any disclaimer, the term of this patent is extended or adjusted under 35 U.S.C. 154(b) by 651 days.

This patent is subject to a terminal disclaimer.

(21) Appl. No.: 12/130,032

(22) Filed: May 30, 2008

(65) Prior Publication Data

US 2008/0306540 A1 Dec. 11, 2008

Related U.S. Application Data

(60) Provisional application No. 61/057,340, filed on May 30, 2008, provisional application No. 60/942,162, filed on Jun. 5, 2007, provisional application No. 61/028,792, filed on Feb. 14, 2008, provisional application No. 61/031,598, filed on Feb. 26, 2008.

(51) Int. Cl.
*A61B 17/70* (2006.01)
*A61B 17/04* (2006.01)

(52) U.S. Cl. .......................................... 606/254
(58) Field of Classification Search ............... 606/279, 606/257, 255, 263, 276, 254, 264, 246, 278, 606/301, 305; 411/400, 401; 403/76, 77
See application file for complete search history.

(56) References Cited

U.S. PATENT DOCUMENTS

| | | | |
|---|---|---|---|
| 4,041,939 A | 8/1977 | Hall | 128/69 |
| 4,065,817 A | 1/1978 | Branemark et al. | 3/1.91 |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |

(Continued)

FOREIGN PATENT DOCUMENTS

DE 2649042 B1 10/1976

(Continued)

OTHER PUBLICATIONS

International Search Report for PCT/US/08/65443 dated Sep. 16, 2008, 4 pages.

(Continued)

*Primary Examiner* — Pedro Philogene
(74) *Attorney, Agent, or Firm* — Fliesler Meyer LLP

(57) ABSTRACT

A dynamic stabilization, motion preservation spinal implant system includes a deflection rod system implant. The system is modular so that various constructs and configurations can be created and customized to a patient.

20 Claims, 31 Drawing Sheets

U.S. PATENT DOCUMENTS

| | | | |
|---|---|---|---|
| 4,422,451 A | 12/1983 | Kalamchi | 128/69 |
| 4,479,491 A | 10/1984 | Martin | 128/92 |
| 4,567,885 A | 2/1986 | Androphy | 128/92 |
| 4,573,454 A | 3/1986 | Hoffman | 128/69 |
| 4,604,995 A | 8/1986 | Stephens et al. | 128/69 |
| 4,611,580 A | 9/1986 | Wu | 128/69 |
| 4,611,581 A | 9/1986 | Steffee | 128/69 |
| 4,611,582 A | 9/1986 | Duff | 128/69 |
| 4,641,636 A | 2/1987 | Cotrel | 128/69 |
| 4,648,388 A | 3/1987 | Steffee | 128/69 |
| 4,653,481 A | 3/1987 | Howland et al. | 128/69 |
| 4,653,489 A | 3/1987 | Tronzo | 128/92 |
| 4,655,199 A | 4/1987 | Steffee | 128/69 |
| 4,658,809 A | 4/1987 | Ulrich et al. | 128/92 |
| 4,696,290 A | 9/1987 | Steffee | 128/69 |
| 4,719,905 A | 1/1988 | Steffee | 128/69 |
| 4,763,644 A | 8/1988 | Webb | 128/69 |
| 4,773,402 A | 9/1988 | Asher et al. | 128/69 |
| 4,805,602 A | 2/1989 | Puno et al. | 128/69 |
| 4,815,453 A | 3/1989 | Cotrel | 128/69 |
| 4,887,595 A | 12/1989 | Heinig et al. | 606/61 |
| 4,913,134 A | 4/1990 | Luque | 128/69 |
| 4,946,458 A | 8/1990 | Harms et al. | 606/61 |
| 4,950,269 A | 8/1990 | Gaines, Jr. | 606/61 |
| 4,955,885 A | 9/1990 | Meyers | 606/53 |
| 4,987,892 A | 1/1991 | Krag et al. | 606/61 |
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,042,982 A | 8/1991 | Harms et al. | 606/61 |
| 5,047,029 A | 9/1991 | Aebi et al. | 606/61 |
| 5,067,955 A | 11/1991 | Cotrel | 606/61 |
| 5,074,864 A | 12/1991 | Cozad et al. | 606/54 |
| 5,084,049 A | 1/1992 | Asher et al. | 606/61 |
| 5,092,866 A | 3/1992 | Breard et al. | 606/61 |
| 5,102,412 A | 4/1992 | Rogozinski | 606/61 |
| 5,112,332 A | 5/1992 | Cozad et al. | 606/61 |
| 5,113,685 A | 5/1992 | Asher et al. | 72/458 |
| 5,127,912 A | 7/1992 | Ray et al. | 606/61 |
| 5,129,388 A | 7/1992 | Vignaud et al. | 606/61 |
| 5,129,900 A | 7/1992 | Asher et al. | 606/61 |
| 5,147,359 A | 9/1992 | Cozad et al. | 606/61 |
| 5,154,718 A | 10/1992 | Cozad et al. | 606/61 |
| 5,176,680 A | 1/1993 | Vignaud et al. | 606/61 |
| 5,180,393 A | 1/1993 | Commarmond | 623/13 |
| 5,190,543 A | 3/1993 | Schläpfer | 606/61 |
| 5,201,734 A | 4/1993 | Cozad et al. | 606/62 |
| 5,207,678 A | 5/1993 | Harms et al. | 606/61 |
| 5,261,911 A | 11/1993 | Carl | 606/61 |
| 5,261,912 A | 11/1993 | Frigg | 606/61 |
| 5,261,913 A | 11/1993 | Marnay | 606/61 |
| 5,281,222 A | 1/1994 | Allard et al. | 606/54 |
| 5,282,801 A | 2/1994 | Sherman | 606/61 |
| 5,282,863 A | 2/1994 | Burton | 623/17 |
| 5,290,289 A | 3/1994 | Sanders et al. | 606/61 |
| 5,312,402 A | 5/1994 | Schläpfer et al. | 606/53 |
| 5,312,404 A | 5/1994 | Asher et al. | 606/61 |
| 5,344,422 A | 9/1994 | Frigg | 606/61 |
| 5,346,493 A | 9/1994 | Stahurski et al. | 606/61 |
| 5,360,429 A | 11/1994 | Jeanson et al. | 606/61 |
| 5,360,431 A | 11/1994 | Puno et al. | 606/72 |
| 5,380,325 A | 1/1995 | Lahille et al. | 606/61 |
| 5,380,326 A | 1/1995 | Lin | 606/61 |
| 5,382,248 A | 1/1995 | Jacobson et al. | 606/60 |
| 5,385,583 A | 1/1995 | Cotrel | 623/17 |
| 5,387,213 A | 2/1995 | Breard et al. | 606/61 |
| 5,415,661 A | 5/1995 | Holmes | 606/69 |
| 5,429,639 A | 7/1995 | Judet | 606/61 |
| 5,437,672 A | 8/1995 | Alleyne | |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,487,742 A | 1/1996 | Cotrel | 606/61 |
| 5,496,321 A | 3/1996 | Puno et al. | 606/61 |
| 5,498,264 A | 3/1996 | Schlapfer et al. | 606/72 |
| 5,520,689 A | 5/1996 | Schläpfer et al. | 606/61 |
| 5,534,001 A | 7/1996 | Schlapfer et al. | 606/61 |
| 5,536,268 A | 7/1996 | Griss | 606/61 |
| 5,540,688 A | 7/1996 | Navas | 606/61 |
| 5,545,167 A | 8/1996 | Lin | 606/61 |
| 5,549,607 A | 8/1996 | Olson et al. | 606/61 |
| 5,562,737 A | 10/1996 | Graf | 623/17 |
| 5,569,248 A | 10/1996 | Mathews | 606/61 |
| 5,609,592 A | 3/1997 | Brumfield et al. | 606/61 |
| 5,609,593 A | 3/1997 | Errico et al. | 606/61 |
| 5,611,800 A | 3/1997 | Davis et al. | 606/61 |
| 5,624,441 A | 4/1997 | Sherman et al. | 606/61 |
| 5,628,740 A | 5/1997 | Mullane | 606/61 |
| 5,630,816 A | 5/1997 | Kambin | 606/61 |
| 5,643,260 A | 7/1997 | Doherty | 606/61 |
| 5,645,599 A | 7/1997 | Samani | 623/17 |
| 5,651,789 A | 7/1997 | Cotrel | 606/61 |
| 5,653,708 A | 8/1997 | Howland | 606/61 |
| 5,658,284 A | 8/1997 | Sebastian et al. | 606/61 |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,672,175 A | 9/1997 | Martin | 606/61 |
| 5,672,176 A | 9/1997 | Biedermann et al. | 606/61 |
| 5,676,665 A | 10/1997 | Bryan | 606/61 |
| 5,676,703 A | 10/1997 | Gelbard | 623/17 |
| 5,681,311 A | 10/1997 | Foley et al. | 606/61 |
| 5,681,319 A | 10/1997 | Biedermann et al. | 606/104 |
| 5,683,391 A | 11/1997 | Boyd | 606/61 |
| 5,683,392 A | 11/1997 | Richelsoph et al. | 606/61 |
| 5,683,393 A | 11/1997 | Ralph | 606/61 |
| 5,688,272 A | 11/1997 | Montague et al. | 606/61 |
| 5,688,273 A | 11/1997 | Errico et al. | 606/61 |
| 5,690,629 A | 11/1997 | Asher et al. | 606/61 |
| 5,690,632 A | 11/1997 | Schwartz et al. | 606/73 |
| 5,690,633 A | 11/1997 | Taylor et al. | 606/73 |
| 5,693,053 A | 12/1997 | Estes | 606/61 |
| 5,697,929 A | 12/1997 | Mellinger | 606/61 |
| 5,700,292 A | 12/1997 | Margulies | 623/17 |
| 5,702,392 A | 12/1997 | Wu et al. | 606/61 |
| 5,702,394 A | 12/1997 | Henry et al. | 606/61 |
| 5,702,395 A | 12/1997 | Hopf | 606/61 |
| 5,702,396 A | 12/1997 | Hoenig et al. | 606/69 |
| 5,702,399 A | 12/1997 | Kilpela et al. | 606/72 |
| 5,702,452 A | 12/1997 | Argenson et al. | 623/17 |
| 5,713,900 A | 2/1998 | Benzel et al. | 606/61 |
| 5,713,904 A | 2/1998 | Errico et al. | 606/73 |
| 5,716,355 A | 2/1998 | Jackson et al. | 606/61 |
| 5,716,356 A | 2/1998 | Biedermann et al. | 606/61 |
| 5,716,357 A | 2/1998 | Rogozinski | 606/61 |
| 5,716,358 A | 2/1998 | Ochoa et al. | 606/62 |
| 5,716,359 A | 2/1998 | Ojima et al. | 606/76 |
| 5,720,751 A | 2/1998 | Jackson | 606/86 |
| 5,725,528 A | 3/1998 | Errico et al. | 606/61 |
| 5,725,582 A | 3/1998 | Bevan et al. | 623/17 |
| 5,728,098 A | 3/1998 | Sherman et al. | 606/61 |
| 5,733,286 A | 3/1998 | Errico et al. | 606/61 |
| 5,735,851 A | 4/1998 | Errico et al. | 606/61 |
| 5,741,254 A | 4/1998 | Henry et al. | 606/61 |
| 5,743,907 A | 4/1998 | Asher et al. | 606/61 |
| 5,743,911 A | 4/1998 | Cotrel | 606/61 |
| 5,752,957 A | 5/1998 | Ralph et al. | 606/61 |
| 5,766,254 A | 6/1998 | Gelbard | 623/17 |
| 5,776,135 A | 7/1998 | Errico et al. | 606/61 |
| 5,782,833 A | 7/1998 | Haider | 606/61 |
| 5,785,711 A | 7/1998 | Errico et al. | 606/61 |
| 5,797,911 A | 8/1998 | Sherman et al. | 606/61 |
| 5,800,435 A | 9/1998 | Errico et al. | 606/61 |
| 5,810,819 A | 9/1998 | Errico et al. | 606/61 |
| 5,863,293 A | 1/1999 | Richelsoph | 606/61 |
| 5,879,350 A | 3/1999 | Sherman et al. | 606/61 |
| 5,885,286 A | 3/1999 | Sherman et al. | 606/61 |
| 5,891,145 A | 4/1999 | Morrison et al. | 606/61 |
| 5,899,904 A | 5/1999 | Errico et al. | 606/61 |
| RE36,221 E | 6/1999 | Breard et al. | 606/61 |
| 5,910,142 A | 6/1999 | Tatar | 606/61 |
| 5,925,047 A | 7/1999 | Errico et al. | 606/65 |
| 5,928,231 A | 7/1999 | Klein et al. | 606/60 |
| 5,928,232 A | 7/1999 | Howland et al. | 606/61 |
| 5,928,233 A | 7/1999 | Apfelbaum et al. | 606/61 |
| 5,947,965 A | 9/1999 | Bryan | 606/61 |
| 5,947,969 A | 9/1999 | Errico et al. | 606/61 |

| Patent No. | Date | Inventor | Class |
|---|---|---|---|
| 5,954,725 A | 9/1999 | Sherman et al. | 606/78 |
| 5,961,517 A | 10/1999 | Biedermann et al. | 606/61 |
| 5,964,760 A | 10/1999 | Richelsoph | 606/61 |
| 5,980,521 A | 11/1999 | Montague et al. | 606/61 |
| 5,980,523 A | 11/1999 | Jackson | 606/61 |
| 5,984,922 A | 11/1999 | McKay | 606/61 |
| 5,989,251 A | 11/1999 | Nichols | 606/61 |
| 5,989,254 A | 11/1999 | Katz | 606/73 |
| 6,001,098 A | 12/1999 | Metz-Stavenhagen et al. | 606/61 |
| 6,004,322 A | 12/1999 | Bernstein | 606/61 |
| 6,010,503 A | 1/2000 | Richelsoph et al. | 606/61 |
| 6,015,409 A | 1/2000 | Jackson | 606/61 |
| 6,036,693 A | 3/2000 | Yuan et al. | 606/61 |
| 6,050,997 A | 4/2000 | Mullane | 606/61 |
| 6,053,917 A | 4/2000 | Sherman et al. | 606/61 |
| 6,063,089 A | 5/2000 | Errico et al. | 606/61 |
| 6,077,262 A | 6/2000 | Schläpfer et al. | 606/61 |
| 6,086,588 A | 7/2000 | Ameil et al. | 606/61 |
| 6,090,111 A | 7/2000 | Nichols | 606/61 |
| 6,096,039 A | 8/2000 | Stoltenberg et al. | 606/61 |
| 6,113,600 A | 9/2000 | Drummond et al. | 606/61 |
| 6,113,601 A | 9/2000 | Tatar | 606/61 |
| 6,127,597 A | 10/2000 | Beyar et al. | 623/16 |
| 6,132,430 A | 10/2000 | Wagner | 606/61 |
| 6,132,434 A | 10/2000 | Sherman et al. | 606/78 |
| 6,136,000 A | 10/2000 | Louis et al. | 606/61 |
| 6,146,383 A | 11/2000 | Studer et al. | 606/61 |
| 6,171,311 B1 | 1/2001 | Richelsoph | 606/61 |
| 6,193,720 B1 | 2/2001 | Yuan et al. | 606/61 |
| 6,197,028 B1 | 3/2001 | Ray et al. | 606/61 |
| 6,210,413 B1 | 4/2001 | Justis et al. | 606/61 |
| 6,217,578 B1 | 4/2001 | Crozet et al. | 606/61 |
| 6,248,106 B1 | 6/2001 | Ferree | 606/61 |
| 6,254,602 B1 | 7/2001 | Justis | 606/61 |
| 6,261,287 B1 | 7/2001 | Metz-Stavenhagen | 606/61 |
| 6,273,888 B1 | 8/2001 | Justis | 606/61 |
| 6,273,914 B1 | 8/2001 | Papas | 623/17.11 |
| 6,280,443 B1 | 8/2001 | Gu et al. | 606/61 |
| 6,287,311 B1 | 9/2001 | Sherman et al. | 606/78 |
| 6,293,949 B1 | 9/2001 | Justis et al. | 606/61 |
| 6,302,882 B1 | 10/2001 | Lin et al. | |
| 6,302,888 B1 | 10/2001 | Mellinger et al. | 606/73 |
| 6,309,391 B1 | 10/2001 | Crandall et al. | 606/61 |
| 6,325,802 B1 | 12/2001 | Frigg | 606/61 |
| 6,328,740 B1 | 12/2001 | Richelsoph | 606/61 |
| 6,344,057 B1 | 2/2002 | Rabbe et al. | 623/17 |
| 6,355,040 B1 | 3/2002 | Richelsoph et al. | 606/61 |
| 6,379,354 B1 | 4/2002 | Rogozinski | 606/61 |
| 6,402,749 B1 | 6/2002 | Ashman | 606/61 |
| 6,402,751 B1 | 6/2002 | Hoeck et al. | 606/61 |
| 6,402,752 B2 | 6/2002 | Schäffler-Wachter et al. | 606/61 |
| 6,413,257 B1 | 7/2002 | Lin et al. | 606/61 |
| 6,416,515 B1 | 7/2002 | Wagner | 606/61 |
| 6,423,064 B1 | 7/2002 | Kluger | 606/61 |
| 6,440,169 B1 | 8/2002 | Elberg et al. | 623/17.16 |
| 6,451,021 B1 | 9/2002 | Ralph et al. | 606/61 |
| 6,454,773 B1 | 9/2002 | Sherman et al. | 606/78 |
| 6,458,131 B1 | 10/2002 | Ray | 606/61 |
| 6,458,132 B2 | 10/2002 | Choi | 606/61 |
| 6,468,276 B1 | 10/2002 | McKay | 606/61 |
| 6,471,705 B1 | 10/2002 | Biedermann et al. | 606/61 |
| 6,478,797 B1 | 11/2002 | Paul | 606/61 |
| 6,482,207 B1 | 11/2002 | Errico | 606/61 |
| 6,485,491 B1 | 11/2002 | Farris et al. | 606/61 |
| 6,488,681 B2 | 12/2002 | Martin et al. | 606/61 |
| 6,520,962 B1 | 2/2003 | Taylor et al. | 606/61 |
| 6,520,990 B1 | 2/2003 | Ray | 623/17.11 |
| 6,537,276 B2 | 3/2003 | Metz-Stavenhagen | 606/61 |
| 6,540,748 B2 | 4/2003 | Lombardo | 606/61 |
| 6,540,749 B2 | 4/2003 | Schäfer et al. | 606/61 |
| 6,547,789 B1 | 4/2003 | Ventre et al. | 606/61 |
| 6,554,832 B2 | 4/2003 | Shluzas | 606/61 |
| 6,554,834 B1 | 4/2003 | Crozet et al. | 606/65 |
| 6,565,565 B1 | 5/2003 | Yuan et al. | 606/61 |
| 6,565,566 B1 | 5/2003 | Wagner et al. | 606/61 |
| 6,565,567 B1 | 5/2003 | Haider | 606/61 |
| 6,565,605 B2 | 5/2003 | Goble et al. | 623/17.11 |
| 6,572,617 B1 | 6/2003 | Senegas | 606/61 |
| 6,572,653 B1 | 6/2003 | Simonson | 623/17.13 |
| 6,579,290 B1 | 6/2003 | Hardcastle et al. | 606/61 |
| 6,585,737 B1 | 7/2003 | Baccelli et al. | 606/61 |
| 6,616,669 B2 | 9/2003 | Ogilvie et al. | 606/61 |
| 6,623,485 B2 | 9/2003 | Doubler et al. | 606/61 |
| 6,626,905 B1 | 9/2003 | Schmiel et al. | 606/61 |
| 6,626,908 B2 | 9/2003 | Cooper et al. | 606/61 |
| 6,645,207 B2 | 11/2003 | Dixon et al. | 606/61 |
| 6,652,526 B1 | 11/2003 | Arafiles | 606/61 |
| 6,656,181 B2 | 12/2003 | Dixon et al. | 606/69 |
| 6,660,004 B2 | 12/2003 | Barker et al. | 606/61 |
| 6,660,005 B2 | 12/2003 | Toyama et al. | 606/61 |
| 6,695,845 B2 | 2/2004 | Dixon et al. | 606/70 |
| 6,706,045 B2 | 3/2004 | Lin et al. | 606/61 |
| 6,709,434 B1 | 3/2004 | Gournay et al. | 606/61 |
| 6,716,213 B2 | 4/2004 | Shitoto | 606/61 |
| 6,716,214 B1 | 4/2004 | Jackson | 606/61 |
| 6,726,689 B2 | 4/2004 | Jackson | 606/73 |
| 6,736,820 B2 | 5/2004 | Biedermann et al. | 606/73 |
| 6,740,086 B2 | 5/2004 | Richelsoph | |
| 6,749,614 B2 | 6/2004 | Teitelbaum et al. | 606/61 |
| 6,752,807 B2 | 6/2004 | Lin et al. | 606/61 |
| 6,755,829 B1 | 6/2004 | Bono et al. | 606/61 |
| 6,755,835 B2 | 6/2004 | Schultheiss et al. | 606/73 |
| 6,761,719 B2 | 7/2004 | Justis et al. | 606/61 |
| 6,783,526 B1 | 8/2004 | Lin et al. | 606/61 |
| 6,783,527 B2 | 8/2004 | Drewry et al. | 606/61 |
| 6,786,907 B2 | 9/2004 | Lange | 606/61 |
| 6,793,656 B1 | 9/2004 | Mathews | 606/61 |
| 6,805,695 B2 | 10/2004 | Keith et al. | 606/61 |
| 6,805,714 B2 | 10/2004 | Sutcliffe | 623/17.11 |
| 6,811,567 B2 | 11/2004 | Reiley | 623/17.11 |
| 6,832,999 B2 | 12/2004 | Ueyama et al. | 606/61 |
| 6,840,940 B2 | 1/2005 | Ralph et al. | 606/61 |
| 6,843,791 B2 | 1/2005 | Serhan | 606/61 |
| 6,852,128 B2 | 2/2005 | Lange | 623/17.11 |
| 6,858,030 B2 | 2/2005 | Martin et al. | 606/61 |
| 6,869,433 B2 | 3/2005 | Glascott | 606/73 |
| 6,875,211 B2 | 4/2005 | Nichols et al. | 606/61 |
| 6,881,215 B2 | 4/2005 | Assaker et al. | 606/61 |
| 6,883,520 B2 | 4/2005 | Lambrecht | 128/898 |
| 6,887,242 B2 | 5/2005 | Doubler et al. | 606/61 |
| 6,899,714 B2 | 5/2005 | Vaughan | 606/61 |
| 6,918,911 B2 | 7/2005 | Biedermann et al. | 606/61 |
| 6,932,817 B2 | 8/2005 | Baynham et al. | 606/61 |
| 6,945,974 B2 | 9/2005 | Dalton | 606/70 |
| 6,951,561 B2 | 10/2005 | Warren et al. | 606/73 |
| 6,964,666 B2 | 11/2005 | Jackson | 606/61 |
| 6,966,910 B2 | 11/2005 | Ritland | 606/61 |
| 6,986,771 B2 | 1/2006 | Paul et al. | 606/61 |
| 6,991,632 B2 | 1/2006 | Ritland | 606/61 |
| 7,008,423 B2 | 3/2006 | Assaker et al. | 606/61 |
| 7,011,685 B2 | 3/2006 | Arnin et al. | 623/17.16 |
| 7,018,378 B2 | 3/2006 | Biedermann et al. | 606/61 |
| 7,018,379 B2 | 3/2006 | Drewry | 606/61 |
| 7,022,122 B2 | 4/2006 | Amrein et al. | 606/61 |
| 7,029,475 B2 | 4/2006 | Panjabi | 606/61 |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,214,227 B2 | 5/2007 | Colleran et al. | 606/61 |
| 7,250,052 B2 | 7/2007 | Landry et al. | 606/61 |
| 7,282,064 B2 | 10/2007 | Chin | 623/17.15 |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,326,210 B2 | 2/2008 | Jahng et al. | 606/61 |

| Patent/Publication | Date | Name |
|---|---|---|
| 7,335,201 B2 | 2/2008 | Doubler et al. ............... 606/61 |
| 7,713,288 B2 * | 5/2010 | Timm et al. .................. 606/257 |
| 7,722,649 B2 * | 5/2010 | Biedermann et al. ......... 606/257 |
| 7,819,902 B2 * | 10/2010 | Abdelgany et al. ........... 606/267 |
| 7,854,752 B2 * | 12/2010 | Colleran et al. .............. 606/279 |
| 2002/0013586 A1 | 1/2002 | Justis et al. |
| 2002/0026192 A1 | 2/2002 | Schmiel et al. |
| 2002/0068975 A1 | 6/2002 | Teitelbaum et al. |
| 2002/0082603 A1 | 6/2002 | Dixon et al. |
| 2002/0120271 A1 | 8/2002 | Dixon et al. |
| 2002/0143329 A1 | 10/2002 | Serhan et al. |
| 2002/0169450 A1 | 11/2002 | Lange |
| 2003/0004511 A1 | 1/2003 | Ferree |
| 2003/0073996 A1 | 4/2003 | Doubler et al. |
| 2003/0073997 A1 | 4/2003 | Doubler et al. |
| 2003/0083657 A1 | 5/2003 | Drewry et al. |
| 2003/0125742 A1 | 7/2003 | Yuan et al. |
| 2003/0171749 A1 | 9/2003 | Le Couedic et al. |
| 2004/0015166 A1 | 1/2004 | Gorek |
| 2004/0030337 A1 | 2/2004 | Alleyne et al. |
| 2004/0039384 A1 | 2/2004 | Boehm, Jr. et al. |
| 2004/0097925 A1 | 5/2004 | Boehm, Jr. et al. |
| 2004/0097933 A1 | 5/2004 | Lourdel et al. |
| 2004/0111088 A1 | 6/2004 | Picetti et al. |
| 2004/0116929 A1 | 6/2004 | Barker et al. |
| 2004/0122425 A1 | 6/2004 | Suzuki et al. |
| 2004/0138662 A1 | 7/2004 | Landry et al. |
| 2004/0143264 A1 | 7/2004 | McAfee |
| 2004/0143265 A1 | 7/2004 | Landry et al. |
| 2004/0147928 A1 | 7/2004 | Landry et al. |
| 2004/0153077 A1 | 8/2004 | Biedermann et al. |
| 2004/0158245 A1 | 8/2004 | Chin |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172024 A1 | 9/2004 | Gorek |
| 2004/0215192 A1 | 10/2004 | Justis et al. |
| 2004/0225289 A1 | 11/2004 | Biedermann et al. |
| 2004/0230192 A1 | 11/2004 | Graf |
| 2004/0236327 A1 | 11/2004 | Paul et al. |
| 2004/0236330 A1 | 11/2004 | Purcell et al. |
| 2005/0033441 A1 | 2/2005 | Lambrecht et al. |
| 2005/0049589 A1 | 3/2005 | Jackson |
| 2005/0065515 A1 | 3/2005 | Jahng |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085813 A1 | 4/2005 | Spitler et al. |
| 2005/0090822 A1 | 4/2005 | DiPoto |
| 2005/0096652 A1 | 5/2005 | Burton |
| 2005/0096659 A1 | 5/2005 | Freudiger |
| 2005/0107788 A1 | 5/2005 | Beaurain et al. |
| 2005/0113927 A1 | 5/2005 | Malek |
| 2005/0113929 A1 | 5/2005 | Cragg et al. |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0143737 A1 | 6/2005 | Pafford et al. |
| 2005/0143823 A1 | 6/2005 | Boyd et al. |
| 2005/0171537 A1 | 8/2005 | Mazel et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0187548 A1 | 8/2005 | Butler et al. |
| 2005/0192569 A1 | 9/2005 | Nichols et al. |
| 2005/0192571 A1 | 9/2005 | Abdelgany |
| 2005/0192572 A1 | 9/2005 | Abdelgany et al. |
| 2005/0203514 A1 | 9/2005 | Jahng et al. |
| 2005/0203517 A1 | 9/2005 | Jahng et al. |
| 2005/0203518 A1 | 9/2005 | Biedermann et al. |
| 2005/0222570 A1 | 10/2005 | Jackson |
| 2005/0228375 A1 | 10/2005 | Mazda et al. |
| 2005/0228382 A1 | 10/2005 | Richelsoph et al. |
| 2005/0228385 A1 | 10/2005 | Iott et al. |
| 2005/0234451 A1 | 10/2005 | Markworth |
| 2005/0234454 A1 | 10/2005 | Chin |
| 2005/0234557 A1 | 10/2005 | Lambrecht et al. |
| 2005/0240180 A1 | 10/2005 | Vienney et al. |
| 2005/0240265 A1 | 10/2005 | Kuiper et al. |
| 2005/0240266 A1 | 10/2005 | Kuiper et al. |
| 2005/0261770 A1 | 11/2005 | Kuiper et al. |
| 2005/0267470 A1 | 12/2005 | McBride |
| 2005/0267472 A1 | 12/2005 | Biedermann et al. |
| 2005/0277922 A1 | 12/2005 | Trieu et al. |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0288670 A1 | 12/2005 | Panjabi et al. |
| 2005/0288671 A1 | 12/2005 | Yuan et al. |
| 2006/0004357 A1 | 1/2006 | Lee et al. |
| 2006/0025771 A1 | 2/2006 | Jackson |
| 2006/0030839 A1 | 2/2006 | Park et al. |
| 2006/0036242 A1 | 2/2006 | Nilsson et al. |
| 2006/0036324 A1 | 2/2006 | Sachs et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058787 A1 | 3/2006 | David |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0069391 A1 | 3/2006 | Jackson |
| 2006/0074419 A1 | 4/2006 | Taylor et al. |
| 2006/0079894 A1 | 4/2006 | Colleran et al. |
| 2006/0079896 A1 | 4/2006 | Kwak et al. |
| 2006/0084978 A1 | 4/2006 | Mokhtar |
| 2006/0084980 A1 | 4/2006 | Melkent et al. |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084990 A1 | 4/2006 | Gournay et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0095035 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106380 A1 | 5/2006 | Colleran et al. |
| 2006/0106383 A1 | 5/2006 | Biedermann et al. |
| 2006/0111712 A1 | 5/2006 | Jackson |
| 2006/0111715 A1 | 5/2006 | Jackson |
| 2006/0116676 A1 | 6/2006 | Gradel et al. |
| 2006/0122597 A1 | 6/2006 | Jones et al. |
| 2006/0122599 A1 | 6/2006 | Drewry et al. |
| 2006/0122620 A1 | 6/2006 | Kim |
| 2006/0129147 A1 | 6/2006 | Biedermann et al. |
| 2006/0129148 A1 | 6/2006 | Simmons et al. |
| 2006/0129149 A1 | 6/2006 | Iott et al. |
| 2006/0142761 A1 | 6/2006 | Landry et al. |
| 2006/0149231 A1 | 7/2006 | Bray |
| 2006/0149232 A1 | 7/2006 | Sasing |
| 2006/0149234 A1 | 7/2006 | de Coninck |
| 2006/0149237 A1 | 7/2006 | Markworth et al. |
| 2006/0149238 A1 | 7/2006 | Sherman et al. |
| 2006/0149240 A1 | 7/2006 | Jackson |
| 2006/0149242 A1 | 7/2006 | Kraus et al. |
| 2006/0149244 A1 | 7/2006 | Amrein et al. |
| 2006/0149380 A1 | 7/2006 | Lotz et al. |
| 2006/0155277 A1 | 7/2006 | Metz-Stavenhagen |
| 2006/0155278 A1 | 7/2006 | Warnick |
| 2006/0161153 A1 | 7/2006 | Hawkes et al. |
| 2006/0173456 A1 | 8/2006 | Hawkes et al. |

| Publication No. | Date | Inventor |
|---|---|---|
| 2006/0189983 A1 | 8/2006 | Fallin et al. |
| 2006/0195093 A1 | 8/2006 | Jahng |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200133 A1 | 9/2006 | Jackson |
| 2006/0217716 A1 | 9/2006 | Baker et al. |
| 2006/0229606 A1 | 10/2006 | Clement et al. |
| 2006/0229607 A1 | 10/2006 | Brumfield |
| 2006/0229613 A1 | 10/2006 | Timm et al. |
| 2006/0229615 A1 | 10/2006 | Abdou |
| 2006/0229616 A1 | 10/2006 | Albert et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241594 A1 | 10/2006 | McCarthy et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0241757 A1 | 10/2006 | Anderson |
| 2006/0247623 A1 | 11/2006 | Anderson et al. |
| 2006/0247624 A1 | 11/2006 | Banouskou et al. |
| 2006/0247628 A1 | 11/2006 | Rawlins et al. |
| 2006/0247631 A1 | 11/2006 | Ahn et al. |
| 2006/0247636 A1 | 11/2006 | Yuan et al. |
| 2006/0247637 A1 | 11/2006 | Colleran et al. |
| 2006/0253118 A1 | 11/2006 | Bailey |
| 2006/0264935 A1 | 11/2006 | White |
| 2006/0264937 A1 | 11/2006 | White |
| 2006/0276897 A1 | 12/2006 | Winslow et al. |
| 2006/0282073 A1 | 12/2006 | Simanovsky |
| 2006/0282078 A1 | 12/2006 | Labrom et al. |
| 2007/0005062 A1 | 1/2007 | Lange et al. |
| 2007/0005063 A1 | 1/2007 | Bruneau et al. |
| 2007/0016190 A1 | 1/2007 | Martinez et al. |
| 2007/0016194 A1 | 1/2007 | Shaolian et al. |
| 2007/0016201 A1 | 1/2007 | Freudiger |
| 2007/0032123 A1 | 2/2007 | Timm et al. |
| 2007/0043356 A1 | 2/2007 | Timm et al. |
| 2007/0043358 A1 | 2/2007 | Molz, IV et al. |
| 2007/0049936 A1 | 3/2007 | Colleran et al. |
| 2007/0073289 A1 | 3/2007 | Kwak et al. |
| 2007/0083200 A1 | 4/2007 | Gittings et al. |
| 2007/0088359 A1 | 4/2007 | Woods et al. |
| 2007/0093814 A1 | 4/2007 | Callahan, II et al. |
| 2007/0093820 A1 | 4/2007 | Freudiger |
| 2007/0093821 A1 | 4/2007 | Freudiger |
| 2007/0093829 A1 | 4/2007 | Abdou |
| 2007/0118122 A1 | 5/2007 | Butler et al. |
| 2007/0123861 A1 | 5/2007 | Dewey et al. |
| 2007/0123871 A1 | 5/2007 | Jahng |
| 2007/0156143 A1 | 7/2007 | Lancial |
| 2007/0161994 A1 | 7/2007 | Lowery et al. |
| 2007/0161997 A1 | 7/2007 | Thramann et al. |
| 2007/0162007 A1 | 7/2007 | Shoham |
| 2007/0167947 A1 | 7/2007 | Gittings |
| 2007/0168035 A1 | 7/2007 | Koske |
| 2007/0198014 A1 | 8/2007 | Graf et al. |
| 2007/0213714 A1 | 9/2007 | Justis |
| 2007/0213719 A1 | 9/2007 | Hudgins et al. |
| 2007/0233068 A1 | 10/2007 | Bruneau et al. |
| 2007/0233072 A1 | 10/2007 | Dickinson et al. |
| 2007/0233075 A1 | 10/2007 | Dawson |
| 2007/0233090 A1 | 10/2007 | Naifeh et al. |
| 2007/0233091 A1 | 10/2007 | Naifeh et al. |
| 2007/0233092 A1 | 10/2007 | Falahee |
| 2007/0233093 A1 | 10/2007 | Falahee |
| 2007/0233094 A1 | 10/2007 | Colleran et al. |
| 2007/0244481 A1 | 10/2007 | Timm |
| 2007/0250061 A1 | 10/2007 | Chin et al. |
| 2007/0270819 A1 | 11/2007 | Justis et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0276380 A1 | 11/2007 | Jahng et al. |
| 2007/0288009 A1 | 12/2007 | Brown et al. |
| 2007/0288012 A1 | 12/2007 | Colleran et al. |
| 2008/0009864 A1 | 1/2008 | Forton et al. |
| 2008/0021285 A1 | 1/2008 | Drzyzga et al. |
| 2008/0021459 A1 | 1/2008 | Lim |
| 2008/0021461 A1 | 1/2008 | Barker et al. |
| 2008/0033433 A1 | 2/2008 | Implicito |
| 2008/0039838 A1 | 2/2008 | Landry et al. |
| 2008/0045951 A1 | 2/2008 | Fanger et al. |
| 2008/0045957 A1 | 2/2008 | Landry et al. |
| 2008/0051787 A1 | 2/2008 | Remington et al. |
| 2008/0065073 A1 | 3/2008 | Perriello et al. |
| 2008/0065075 A1 | 3/2008 | Dant et al. |
| 2008/0065079 A1 | 3/2008 | Bruneau et al. |
| 2008/0071273 A1 | 3/2008 | Hawkes et al. |
| 2008/0077139 A1 | 3/2008 | Landry et al. |

FOREIGN PATENT DOCUMENTS

| | | |
|---|---|---|
| DE | 3639810 A1 | 5/1988 |
| EP | 0128058 A1 | 12/1984 |
| EP | 0669109 B1 | 8/1995 |
| EP | 1281362 A2 | 2/2003 |
| EP | 1330987 A1 | 7/2003 |
| FR | 2612070 A1 | 9/1988 |
| FR | 2615095 A1 | 11/1988 |
| FR | 2880256 B1 | 7/2006 |
| GB | 780652 | 8/1957 |
| GB | 2173104 | 10/1986 |
| GB | 2382304 | 5/2003 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO 2004/024011 | 3/2004 |
| WO | WO 2004/034916 | 4/2004 |
| WO | WO 2006/033503 | 3/2006 |
| WO | WO 2006/066685 | 6/2006 |
| WO | WO 2006/105935 | 10/2006 |
| WO | WO 2007/080317 | 7/2007 |
| WO | WO 2008/034130 | 3/2008 |

OTHER PUBLICATIONS

International Search Report for PCT/US/08/65444 dated Sep. 16, 2008, 4 pages.
"Flexible rods and the case for dynamic stabilization," Jason M. Highsmith, M.D., et al., *Neurosurg. Focus*, vol. 22, Jan. 2007, pp. 1-5.
"The Spinous Process: The Forgotten Appendage," Kenneth R. Kattan, M. D. eta l., *Skeletal Radiology*, vol. 6, 1981, pp. 199-204.
"Morphological and functional changes of the lumbar spinous processes in the elderly," R. Scapinelli, *Surgical Radiologic Anatomy*, vol. 11, 1989, pp. 129-133.
"The Paraspinal Sacrospinalis-Splitting Approach to the Lumbar Spine," Leon L. Wiltse et al., *The Journal of Bone & Joint Surgery*, vol. 50-A, No. 5, Jul. 1968 pp. 919-926.
*Dynamic Reconstruction of the Spine*, D.H. Kim et al., 2006, cover through p. xix.
"Historical Review of Spinal Arthroplasty and Dynamic Stabilizations," K M. Shibata et al., *Dynamic Reconstruction of the Spine*, Section I, Motion Preservation of the Spine, Chapter 1, 2006, pp. 3-15.
"Current Concepts in Spinal Fusion versus Nonfusion," D.H. Walker et al., *Dynamic Reconstruction of the Spine*, Section I, Motion Preservation of the Spine, Chapter 2, 2006, pp. 16-23.
"Biomechanical Aspects Associated with Cervical Disk Arthroplasty," D.J. DiAngelo et al., *Dynamic Reconstruction of the*

*Spine*, Section II, Restoration of Cervical Motion Segment, Chapter 3, 2006, pp. 27-32.
"Biomechanical Testing Protocol for Evaluating Cervical Disk Arthroplasty," D.J. DiAngelo et al., *Dynamic Reconstruction of the Spine*, Section II, Restoration of Cervical Motion Segment, Chapter 4, 2006, pp. 33-41.
"Cervical Disk Arthroplasty: Rationale, Indications, and Clinical Experience," M.R. Lim et al., *Dynamic Reconstruction of the Spine*, Section II, Restoration of Cervical Motion Segment, Chapter 5, 2006, pp. 42-51.
"Spinal Kinetics Cervical Disc," D.H. Kim et al., *Dynamic Reconstruction of the Spine*, Section II, Restoration of Cervical Motion Segment, Chapter 6, 2006, pp. 52-58.
"Bryan Cervical Disc Device," R. Hacker, *Dynamic Reconstruction of the Spine*, Section II, Restoration of Cervical Motion Segment, Chapter 7, 2006, pp. 59-66.
"Prestige Cervical Artificial Disk," J.T. Robertson, *Dynamic Reconstruction of the Spine*, Section II, Restoration of Cervical Motion Segment, Chapter 8, 2006, pp. 67-71.
"ProDisc-C Cervical Artificial Disk" G.K. Jeong et al., *Dynamic Reconstruction of the Spine*, Section II, Restoration of Cervical Motion Segment, Chapter 9, 2006, pp. 72-77.
"PCM (Porous Coated Motion) Artificial Cervical Disc," L Pimenta et al., *Dynamic Reconstruction of the Spine*, Section II, Restoration of Cervical Motion Segment, Chapter 10, 2006, pp. 78-85.
"Cervidisc Concept: Six-Year Follow-Up and Introducing Cervidisc II: DISCOCERV," A.S. Ramadan et al., *Dynamic Reconstruction of the Spine*, Section II, Restoration of Cervical Motion Segment, Chapter 11, 2006, pp. 86-91.
"CerviCore Cervical Intervertebral Disk Replacement," S.S. Lee et al., *Dynamic Reconstruction of the Spine*, Section II, Restoration of Cervical Motion Segment, Chapter 12, 2006, pp. 92-95.
"Prosthetic Disk Nucleus Partial Disk Replacement: Pathobiological and Biomechanical Rationale for Design and Function," C.D. Ray et al., *Dynamic Reconstruction of the Spine*, Section III, Restoration of Lumbar Motion Segment, A. Lumbar Nucleus Replacement, Chapter 13, 2006, pp. 99-104.
"Functional Lumbar Artificial Nucleus Replacement: The DASCOR System," J.E. Sherman et al., *Dynamic Reconstruction of the Spine*, Section III, Restoration of Lumbar Motion Segment, A. Lumbar Nucleus Replacement, Chapter 15, 2006, pp. 114-121.
"NeuDisc," R. Bertagnoli et al., *Dynamic Reconstruction of the Spine*, Section III, Restoration of Lumbar Motion Segment, A. Lumbar Nucleus Replacement, Chapter 16, 2006, pp. 122-126.
"Pioneer Surgical Technology Nubac Artificial Nucleus," Q. Bao et al., *Dynamic Reconstruction of the Spine*, Section III, Restoration of Lumbar Motion Segment, A. Lumbar Nucleus Replacement, Chapter 17, 2006, pp. 128-136.
"SINUX (Sinitec)," J. Zoellner, *Dynamic Reconstruction of the Spine*, Section III, Restoration of Lumbar Motion Segment, A. Lumbar Nucleus Replacement, Chapter 18, 2006, pp. 137-141.
"Nucore Injectable Disk Nucleus," S.H. Kitchel et al., *Dynamic Reconstruction of the Spine*, Section III, Restoration of Lumbar Motion Segment, A. Lumbar Nucleus Replacement, Chapter 19, 2006, pp. 142-146.
"Biomechanical Considerations for Total Lumbar Disk Replacement," J. LeHuec et al., *Dynamic Reconstruction of the Spine*, Section III, Restoration of Lumbar Motion Segment, B. Lumbar Total Disk Replacement, Chapter 20, 2006, pp. 149-153.
"Indications for Total Lumbar Disk Replacement," R. Bertagnoli, *Dynamic Reconstruction of the Spine*, Section III, Restoration of Lumbar Motion Segment, B. Lumbar Total Disk Replacement, Chapter 21, 2006, pp. 154-159.
"Charté Artificial Disc," F.H. Geisler, *Dynamic Reconstruction of the Spine*, Section III, Restoration of Lumbar Motion Segment, B. Lumbar Total Disk Replacement, Chapter 22, 2006, pp. 160-178.
"ProDisc Lumbar Artificial Disk," J.E.Zigler et al.,*Dynamic Reconstruction of the Spine*, Section III, Restoration of Lumbar Motion Segment, B. Lumbar Total Disk Replacement, Chapter 23, 2006, pp. 179-185.
"Maverick Total Disc Replacement," M.F.Gornet, *Dynamic Reconstruction of the Spine*, Section III, Restoration of Lumbar Motion Segment, B. Lumbar Total Disk Replacement, Chapter 24, 2006, pp. 186-195.
"The Mobidisc Prosthesis," J.P. Steib et al., *Dynamic Reconstruction of the Spine*, Section III, Restoration of Lumbar Motion Segment, B. Lumbar Total Disk Replacement, Chapter 25, 2006, pp. 196-203.
"Activ-L Lumbar (Aesculap) Total Disk Arthroplasty," J.J. Yue et al., *Dynamic Reconstruction of the Spine*, Section III, Restoration of Lumbar Motion Segment, B. Lumbar Total Disk Replacement, Chapter 26, 2006, pp. 204-211.
"The FlexiCore Disk," A.D. Sharan et al., *Dynamic Reconstruction of the Spine*, Section III, Restoration of Lumbar Motion Segment, B. Lumbar Total Disk Replacement, Chapter 27, 2006, pp. 212-220.
"Management of Vascular and Surgical Approach—Related Complications for Lumbar Total Disk Replacement," S.H. Lee et al., *Dynamic Reconstruction of the Spine*, Section III, Restoration of Lumbar Motion Segment, B. Lumbar Total Disk Replacement, Chapter 28, 2006, pp. 221-226.
"Complications of Lumbar Disk Arthroplasty," Sh Lee et al., *Dynamic Reconstruction of the Spine*, Section III, Restoration of Lumbar Motion Segment, B. Lumbar Total Disk Replacement, Chapter 29, 2006, pp. 227-233.
"Rationale for Dynamic Stabilization," D.S. McNally, *Dynamic Reconstruction of the Spine*, Section III, Restoration of Lumbar Motion Segment, C. Dynamic Posterior Stabilization, Chapter 30, 2006, pp. 237-243.
"Rationale for Dynamic Stabilization II—SoftFlex System," D.K. Sengupta, *Dynamic Reconstruction of the Spine*, Section III, Restoration of Lumbar Motion Segment, C. Dynamic Posterior Stabilization, Chapter 31, 2006, pp. 244-250.
"The X Stop Interspinous Process Decompression System for the Treatment of Lumbar Neurogenic Claudication," R.M. Thunder et al., *Dynamic Reconstruction of the Spine*, Section III, Restoration of Lumbar Motion Segment, C. Dynamic Posterior Stabilization, Chapter 32, 2006, pp. 251-257.
"Dynamic Lumbar Stabilization with the Wallis Interspinous Implant," J. Sénégas, *Dynamic Reconstruction of the Spine*, Section III, Restoration of Lumbar Motion Segment, C. Dynamic Posterior Stabilization, Chapter 33, 2006, pp. 258-267.
"Coflex," Es Kim et al., *Dynamic Reconstruction of the Spine*, Section III, Restoration of Lumbar Motion Segment, C. Dynamic Posterior Stabilization, Chapter 34, 2006, pp. 268-273.
DIAM (Device for Intervertebral Assisted Motion) Spinal Stabilization System, K. Singh et al., *Dynamic Reconstruction of the Spine*, Section III, Restoration of Lumbar Motion Segment, C. Dynamic Posterior Stabilization, Chapter 35, 2006, pp. 274-283.
"Tension Band System," Sh Lee et al., *Dynamic Reconstruction of the Spine*, Section III, Restoration of Lumbar Motion Segment, C. Dynamic Posterior Stabilization, Chapter 36, 2006, pp. 284-291.
"Shape Memory Implant (KIMPF-DI Fixing) System," Ys Kim et al., *Dynamic Reconstruction of the Spine*, Section III, Restoration of Lumbar Motion Segment, C. Dynamic Posterior Stabilization, Chapter 37, 2006, pp. 292-298.
"Treatment of Mobile Vertebral Instability with Dynesys," G. Dubois et al., *Dynamic Reconstruction of the Spine*, Section III, Restoration of Lumbar Motion Segment, C. Dynamic Posterior Stabilization, Chapter 38, 2006, pp. 299-304.
"Graf Soft Stabilization: Graf Ligamentoplasty," Ys Kim et al., *Dynamic Reconstruction of the Spine*, Section III, Restoration of Lumbar Motion Segment, C. Dynamic Posterior Stabilization, Chapter 39, 2006, pp. 305-311.
"Isobar TTL Dynamic Instrumentation," A.E. Castellvi et al., *Dynamic Reconstruction of the Spine*, Section III, Restoration of Lumbar Motion Segment, C. Dynamic Posterior Stabilization, Chapter 40, 2006, pp. 312-322.
"Minimally Invasive Posterior Dynamic Stabilization System," L. Pimenta et al., *Dynamic Reconstruction of the Spine*, Section III, Restoration of Lumbar Motion Segment, C. Dynamic Posterior Stabilization, Chapter 41, 2006, pp. 323-329.
"Nonfusion Stabilization of the Degenerated Lumbar Spine with Cosmic," A. von Strempel, *Dynamic Reconstruction of the Spine*, Section III, Restoration of Lumbar Motion Segment, C. Dynamic Posterior Stabilization, Chapter 42, 2006, pp. 330-339.

"BioFlex Spring Rod Pedicle Screw System," Ys Kim et al., *Dynamic Reconstruction of the Spine*, Section III, Restoration of Lumbar Motion Segment, C. Dynamic Posterior Stabilization, Chapter 43, 2006, pp. 340-344.

"Facet Replacement Technologies," M.R. Lim et al., *Dynamic Reconstruction of the Spine*, Section III, Restoration of Lumbar Motion Segment, D. Facet Replacement, Chapter 44, 2006, pp. 347-353.

"TOPS—Total Posterior Facet Replacement and Dynamic Motion Segment Stabilization System," L.T. Khoo et al., *Dynamic Reconstruction of the Spine*, Section III, Restoration of Lumbar Motion Segment, D. Facet Replacement, Chapter 45, 2006, pp. 354-363.

"Total Facet Arthroplasty System (TFAS)," S. Webb, *Dynamic Reconstruction of the Spine*, Section III, Restoration of Lumbar Motion Segment, D. Facet Replacement, Chapter 46, 2006, pp. 364-371.

"Indications and Techniques in Annuloplasty," M.Y. Wang, *Dynamic Reconstruction of the Spine*, Section III, Restoration of Lumbar Motion Segment, E. Annular Repair, Chapter 47, 2006, pp. 375-379.

"Molecular Therapy of the Intervertebral Disk," S.T. Yoon, *Dynamic Reconstruction of the Spine*, Section IV, Future Biological Approaches to Disk Repair, Chapter 48, 2006, pp. 383-388.

*Dynamic Reconstruction of the Spine*, D.H. Kim et al., 2006, Index, pp. 389-402.

International Search Report for PCT/US07/70981 dated Apr. 23, 2008, 7 pages.

International Search Report for PCT/US/08/65434 dated Oct. 9, 2008, 4 pages.

International Search Report for PCT/US/08/65435 dated Sep. 2, 2008, 4 pages.

* cited by examiner

SPINE IMPLANT WITH A DEFELCTION ROD SYSTEM ANCHORED TO A BONE ANCHOR AND METHOD

CLAIM TO PRIORITY

This application claims priority to all of the following applications including U.S. Provisional Application No. 60/942,162, filed Jun. 5, 2007, entitled "Dynamic Stabilization and Motion Preservation Spinal Implantation System and Method", U.S. patent application Ser. No. 11/832,260, filed Aug. 1, 2007, entitled "Shaped Horizontal Rod for Dynamic Stabilization and Motion Preservation Spinal Implantation System and Method", U.S. patent application Ser. No. 11/832,273, filed Aug. 1, 2007, entitled "Multi-directional Deflection Profile for a Dynamic Stabilization and Motion Preservation Spinal Implantation System and Method", U.S. patent application Ser. No. 11/832,305, filed Aug. 1, 2007, entitled "A Horizontal Rod with a Mounting Platform for a Dynamic Stabilization and Motion Preservation Spinal Implant System and Method", U.S. patent application Ser. No. 11/832,330, filed Aug. 1, 2007, entitled "Multi-dimensional Horizontal Rod for a Dynamic Stabilization and Motion Preservation Spinal Implantation System and Method", U.S. patent application Ser. No. 11/832,338, filed Aug. 1, 2007, entitled "A Bone Anchor With a Yoke-Shaped anchor head for a Dynamic Stabilization and Motion Preservation Spinal Implantation System and Method", U.S. patent application Ser. No. 11/832,358, filed Aug. 1, 2007, entitled "A Bone Anchor With a Curved Mounting Element for a Dynamic Stabilization and Motion Preservation Spinal Implantation System and Method", U.S. patent application Ser. No. 11/832,377, filed Aug. 1, 2007, entitled "Reinforced Bone Anchor for a Dynamic Stabilization and Motion Preservation Spinal Implantation System and Method", U.S. patent application Ser. No. 11/832,400, filed Aug. 1, 2007, entitled "A Bone Anchor With a Compressor Element for Receiving a Rod for a Dynamic Stabilization and Motion Preservation Spinal Implantation System and Method", U.S. patent application Ser. No. 11/832,413, filed Aug. 1, 2007, entitled "Dynamic Stabilization and Motion Preservation Spinal Implantation System and Method with a Deflection Rod", U.S. patent application Ser. No. 11/832,426, filed Aug. 1, 2007, entitled "Dynamic Stabilization and Motion Preservation Spinal Implantation System and Method with a Deflection Rod Mounted in Close Proximity to a Mounting Rod", U.S. patent application Ser. No. 11/832,436, filed Aug. 1, 2007, entitled "Dynamic Stabilization and Motion Preservation Spinal Implantation System and Method", U.S. patent application Ser. No. 11/832,446, filed Aug. 1, 2007, entitled "Super-Elastic Deflection Rod for a Dynamic Stabilization and Motion Preservation Spinal Implantation System and Method", U.S. patent application Ser. No. 11/832,470, filed Aug. 1, 2007, entitled "Revision System and Method for a Dynamic Stabilization and Motion Preservation Spinal Implantation System and Method", U.S. patent application Ser. No. 11/832,485, filed Aug. 1, 2007, entitled "Revision System for a Dynamic Stabilization and Motion Preservation Spinal Implantation System and Method", U.S. patent application Ser. No. 11/832,494, filed Aug. 1, 2007, entitled "Dynamic Stabilization and Motion Preservation Spinal Implantation System and Method", U.S. patent application Ser. No. 11/832,517, filed Aug. 1, 2007, entitled "Implantation Method for Dynamic Stabilization and Motion Preservation Spinal Implantation System and Method", U.S. patent application Ser. No. 11/832,527, filed Aug. 1, 2007, entitled "Modular Spine Treatment Kit for Dynamic Stabilization and Motion Preservation of the Spine", U.S. patent application Ser. No. 11/832,534, filed Aug. 1, 2007, entitled "Horizontally Loaded Dynamic Stabilization and Motion Preservation Spinal Implantation System and Method", U.S. patent application Ser. No. 11/832,548, filed Aug. 1, 2007, entitled "Dynamic Stabilization and Motion Preservation Spinal Implantation System with Horizontal Deflection Rod and Articulating Vertical Rods", U.S. patent application Ser. No. 11/832,557, filed Aug. 1, 2007, entitled "An Anchor System for a Spine Implantation System That Can Move About three Axes", U.S. patent application Ser. No. 11/832,562, filed Aug. 1, 2007, entitled "Rod Capture Mechanism for Dynamic Stabilization and Motion Preservation Spinal Implantation System and Method", U.S. Provisional Application No. 61/028,792, filed Feb. 14, 2008, entitled "A Deflection Rod System for a Dynamic Stabilization and Motion Preservation Spinal Implantation System and Method", U.S. Provisional Application 61/031,598, filed Feb. 26, 2008, entitled "A Deflection Rod System for a Dynamic Stabilization and Motion Preservation Spinal Implantation System and Method", and U.S. Provisional Application No. 61/057,340, filed May 30, 2008, entitled "A Spine Implant With A Deflection Rod System Aligned With A Bone Anchor And Method".

All of the afore-mentioned applications are incorporated herein by reference in their entireties.

CROSS-REFERENCE TO RELATED APPLICATIONS

This application is related to all of the following applications including U.S. patent application Ser. No. 12/130,335, filed May 30, 2008, "A Deflection Rod System For A Spine Implant Including An Inner Rod And An Outer Shell And Method";

U.S. patent application Ser. No. 12/130,359, filed May 30, 2008, entitled "A Deflection Rod System With A Deflection Contouring Shield For A Spine Implant And Method";

U.S. patent application Ser. No. 12/130,367, filed May 30, 2008, entitled "Dynamic Stabilization And Motion Preservation Spinal Implantation System With A Shielded Deflection Rod System And Method";

U.S. patent application Ser. No. 12/130,377, filed May 30, 2008, entitled "A Deflection Rod System For Spine Implant With End Connectors And Method";

U.S. patent application Ser. No. 12/130,383, filed May 30, 2008, entitled "A Deflection Rod System For A Dynamic Stabilization And Motion Preservation Spinal Implantation System And Method";

U.S. patent application Ser. No. 12/130,395, filed May 30, 2008, entitled "A Deflection Rod System For A Dynamic Stabilization And Motion Preservation Spinal Implantation System And Method";

U.S. patent application Ser. No. 12/130,411, filed May 30, 2008, entitled "A Deflection Rod System With Mount For Dynamic Stabilization And Motion Preservation Spinal Implantation System And Method";

U.S. patent application Ser. No. 12/130,423, filed May 30, 2008, entitled "A Deflection Rod System With A Non-Linear Deflection To Load Characteristic For Dynamic Stabilization And Motion Preservation Spinal Implantation System And Method";

U.S. patent application Ser. No. 12/130,454, filed May 30, 2008, entitled "A Deflection Rod System Dimensioned For Deflection To A Load Characteristic For Dynamic Stabilization And Motion Preservation Spinal Implantation System And Method";

U.S. patent application Ser. No. 12/130,457, filed May 30, 2008, entitled "A Deflection Rod System For Use With A Vertebral Fusion Implant For Dynamic Stabilization And Motion Preservation Spinal Implantation System And Method";

U.S. patent application Ser. No. 12/130,467, filed May 30, 2008, entitled "A Dual Deflection Rod System For Dynamic Stabilization And Motion Preservation Spinal Implantation System And Method";

U.S. patent application Ser. No. 12/130,475, filed May 30, 2008, entitled "Method For Implanting A Deflection Rod System And Customizing The Deflection Rod System For A Particular Patient Need For Dynamic Stabilization And Motion Preservation Spinal Implantation System";

U.S. patent application Ser. No. 12/130,095, filed May 30, 2008, entitled "A Spine Implant With A Deflection Rod System Including A Deflection Limiting Shield Associated With A Bone Screw And Method";

U.S. patent application Ser. No. 12/130,127, filed May 30, 2008, entitled "A Spine Implant With A Dual Deflection Rod System Including A Deflection Limiting Shield Associated With A Bone Screw And Method"; and U.S. patent application Ser. No. 12/130,152, filed May 30, 2008, entitled "A Spine Implant With A Deflection Rod System And Connecting Linkages And Method"

All of the afore-mentioned applications are incorporated herein by reference in their entireties.

BACKGROUND OF INVENTION

The most dynamic segment of orthopedic and neurosurgical medical practice over the past decade has been spinal devices designed to fuse the spine to treat a broad range of degenerative spinal disorders. Back pain is a significant clinical problem and the annual costs to treat it, both surgical and medical, is estimated to be over $2 billion. Motion preserving devices to treat back and extremity pain have, however, created a treatment alternative to or in combination with fusion for degenerative disk disease.

DETAILED DESCRIPTION OF THE PREFERRED EMBODIMENTS

Figure 1:
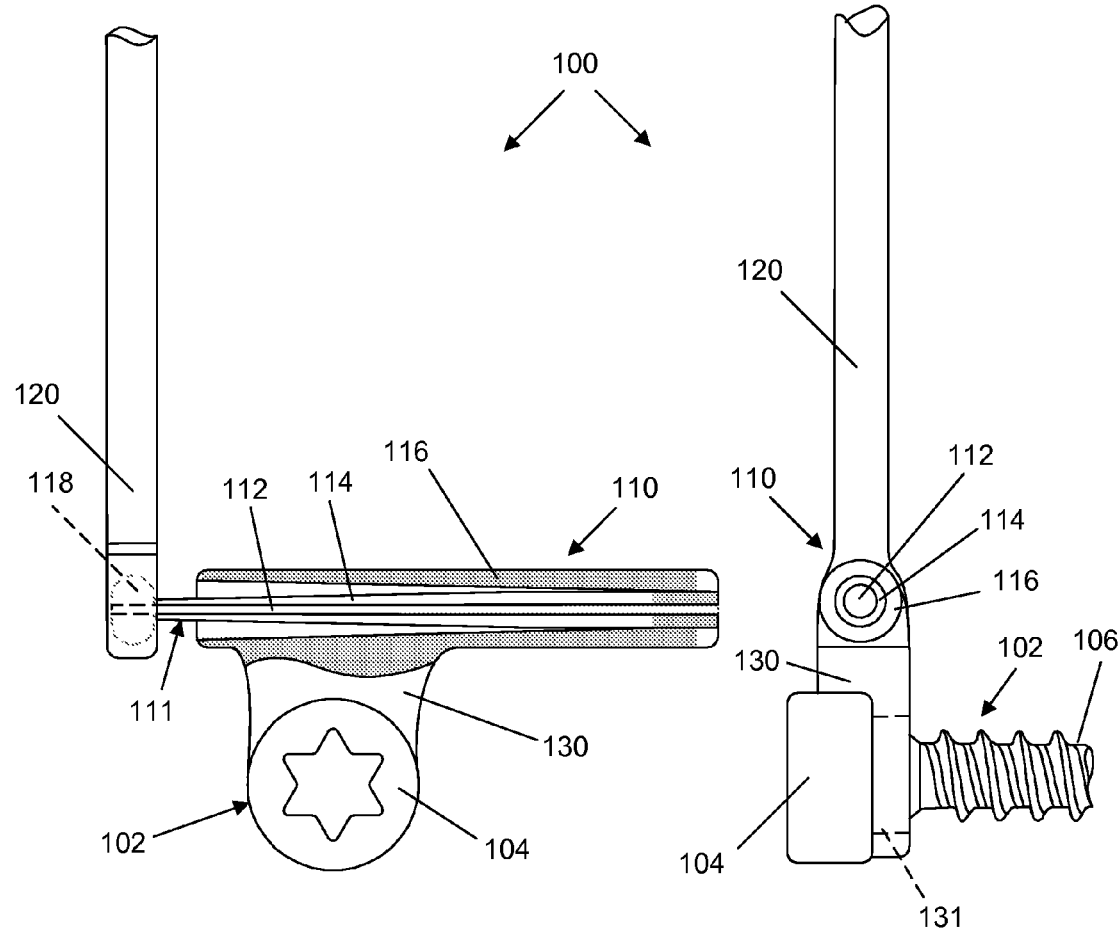
FIG. 1A is a posterior view of an embodiment of a dynamic spine stabilization system in accordance with the present invention.
FIG. 1B is a lateral view of the dynamic spine stabilization system of FIG. 1A.

Embodiments of the present invention include a system or implant and method that can dynamically stabilize the spine while providing for the preservation of spinal motion. Alternative embodiments can be used for spine fusion.

Embodiments of the invention include a construct with an anchoring system, a deflection rod system and a vertical rod system.

An advantage and aspect of some embodiments of anchoring systems in accordance with the present invention is that such embodiments include a head or saddle that allows for appropriate, efficient and convenient placement of the anchoring system relative to the spine in order to reduce the force that is placed on the anchoring system. Such embodiments have enhanced degrees of freedom which contribute to the ease of implantation of the anchor system and are designed to isolate the head from the rest of the dynamic stabilization system and the forces that the rest of the dynamic stabilization system can place on the anchor system and the anchor system/bone interface. Thus, the anchor system can provide a secure purchase in the spine.

An aspect and advantage of the invention is the ability to maximize the range of motion of the spine after embodiments of the dynamic stabilization, motion preservation implant of the invention are implanted in a patient. While traditional solutions to back pain include fusion, discectomy, and artificial implants that replace spine structure, embodiments of the present invention preserve the bone and ligament structure of the spine and preserve a wide range of motion of the spine, while stabilizing spines that were heretofore unstable due to degenerative and other spinal diseases.

Still another aspect of the invention is the preservation of the natural motion of the spine and the maintenance of the quality of motion as well as the wide range of motion so that the spine motion is as close to that of the natural spine as possible. The present embodiments of the invention allow for the selection of a less stiff, yet dynamically stable implant for use in a non-fusion situation. A less stiff, yet dynamically stable implant relates directly to a positive patient outcome, including patient comfort and the quality of motion of the spine.

In another aspect of the invention, load sharing is provided by embodiments, and, in particular, the deflection rod or loading rod of the embodiments. For embodiments of this invention, the terms "deflection rod" and "loading rod" can be used interchangeably. Accordingly this aspect of the invention is directed to restoring the normal motion of the spine. The embodiment provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod or loading rod in order to match the load sharing characteristics desired. By selecting the appropriate stiffness of the deflection rod or loading rod to match the physiology of the patient and the loads that the patient places on the spine, a better outcome is realized for the patient. Prior to implantation of the embodiment, the stiffness of the implant of the system can be selected among a number of loading rods. In other words, the stiffness is variable depending on the deflection rod or loading rod selected. In another aspect, the load sharing is between the spine and the embodiment of the invention.

As the load is carried along the deflection rod or loading rod, the embodiments of the invention can be made smaller in order to fit in more spaces relative to the spine.

An aspect of the invention is to preserve and not restrict motion between the vertebra of the spine through the use of appropriately selected vertical rods (and optionally horizontal rods) of embodiments of the invention.

Another aspect of the invention is the ability to control stiffness for extension, flexion, lateral bending and axial rotation, and to control stiffness for each of these motions independently of the other motions.

An aspect of the invention is to use the stiffness and load bearing characteristics of super elastic materials.

Another aspect of the invention is to use super elastic materials to customize the implant to the motion preservation and the dynamic stabilization needs of a patient. An aspect of such embodiments of the invention is to provide for a force plateau where motion of the implantation system continues without placement of additional force of the bone anchor system, or, in other words, the bone/implantation system interface.

Accordingly, an aspect of the invention is to be able to selectively vary the stiffness and selectively vary the orientation and direction that the stiffness is felt by varying the structure of the implantation system of the invention.

Another aspect of some embodiments of the invention is to prevent and/or provide for any off-axis implantation by allowing the implantation system to have enhanced degrees of freedom of placement of the implant.

A further aspect of embodiments of the invention is to control stabilized motion from micro-motion to broad extension, flexion, axial rotation, and lateral bending motions of the spine.

Yet another aspect of the embodiments of the invention is to be able to revise a dynamic stabilization implant should a fusion implant be indicated. This procedure can be accomplished by, for example, the removal of the deflection rod system of the implantation system and replacement with, for example, a stiffer deflection rod system. Accordingly, an aspect of the invention is to provide for a convenient path for a revision of the original implantation system, if needed.

A further aspect of the invention, due to the ease of implanting the anchoring system, is the ability to accommodate the bone structure of the spine, even if adjacent vertebra are misaligned with respect to each other.

A further aspect of the invention is that the implant is constructed around features of the spine such as the spinous processes and, thus, such features do not need to be removed and the implant does not get in the way of the normal motion of the spine features and the spine features do not get in the way of the operation of the implant.

Another aspect of embodiments of the invention is the ability to stabilize two, three and/or more levels of the spine by the selection of appropriate embodiments and components of embodiments of the invention for implantation in a patient. Further embodiments of the invention allow for fused levels to be placed next to dynamically stabilized levels. Such embodiments of the invention enable vertebral levels adjacent to fusion levels to be shielded by providing a more anatomical change from a rigid fusion level to a dynamically stable, motion preserved, and more mobile level.

Accordingly, another aspect of the embodiments of the invention is to provide a modular system that can be customized to the needs of the patient. A Deflection rod system can be selectively chosen for the particular patient as well the particular levels of the vertebrae of the spine that are treated. Further, the positioning of the embodiments of the invention can be selected to control stiffness and stability.

Another aspect of embodiments of the invention is that embodiments can be constructed to provide for higher stiffness and fusion at one level or to one portion of the spine while allowing for lower stiffness and dynamic stabilization at another adjacent level or to another portion of the spine.

Yet a further aspect of the invention is to provide for dynamic stabilization and motion preservation while preserving the bone and tissues of the spine in order to lessen trauma to the patient and to use the existing functional bone and tissue of the patient as optimally as possible in cooperation with embodiments of the invention.

Another object of the invention is to implant the embodiments of the invention in order to unload force from the spinal facets and other posterior spinal structures and also the intervertebral disc.

A further aspect of the invention is to implant the embodiment of the invention with a procedure that does not remove or alter bone or tear or sever tissue. In an aspect of the invention the muscle and other tissue can be urged out of the way during the inventive implantation procedure.

Accordingly, an aspect of the invention is to provide for a novel implantation procedure that is minimally invasive.
Dynamic Stabilization, Motion Preservation System for the Spine:

Common reference numerals are used throughout the drawings and detailed description to indicate like elements; therefore, reference numerals used in a drawing may or may not be referenced in the detailed description specific to such drawing if the associated element is described elsewhere. Further, the terms "vertical" and "horizontal" are used throughout the detailed description to describe general orientation of structures relative to the spine of a human patient that is standing.

FIG. 1A is a posterior view (in partial cross-section) and FIG. 1B is a lateral view of an embodiment of a deflection rod system implant 100 for use with dynamic stabilization, motion preservation systems (also referred to herein simply as "dynamic stabilization systems") in accordance with the present invention. The deflection rod system implant 100 comprises a deflection rod system or deflection rod system engine 110, an anchoring device 102 and a vertical rod 120. The deflection rod system 110 includes a deflection rod guide or shield 116 and a deflection rod 111 including an inner rod 112 within an outer shell 114. The deflection rod 111 can have a varying diameter along its length. A decreasing diameter allows the deflection rods 111 to be more flexible and bendable along the length deflection rod length to more evenly distribute the load placed on the deflection rod system 100 by the spine. The outer shell 114 preferably is made of PEEK or other comparable polymer and has a diameter that continuously decreases along the length of the deflection rod 111. The inner rod 112 can be comprised of a super elastic material. Preferably, the super elastic material is comprised of Nitinol (NiTi). In addition to Nitinol or nickel-titanium (NiTi), other super elastic materials include copper-zinc-aluminum and copper-aluminum-nickel. However, for biocompatibility, nickel-titanium is the preferred material. The inner rod 112, like the overall deflection rod 111, can vary in diameter and shape, although in a preferred embodiment, the inner rod 112 is substantially cylindrical.

Alternatively, the diameter of the outer shell 114 can decrease in discrete steps along the length of the distraction rod 111, with the diameter of one step not being continuous with the diameter of the next adjacent step. Alternatively, for different force and load carrying criteria the diameters of the deflection rod can continuously increase in diameter or can have discreet step increases in diameter along the length of the deflection rod 111. Still further, the deflection rod 111 can have at least one step of decreasing diameter and at least one step of increasing diameter in any order along the length of the deflection rod 111, as desired for the force and load carrying characteristics of the deflection rod 111.

The deflection rod 111 is arranged within the deflection rod guide or shield 116 which covers and, in this embodiment, substantially surrounds the deflection rod 111. The deflection rod system 110 can be a preassembled unit provided to a surgeon for implantation by affixing the deflection rod system 110 to a bone (e.g., the pedicle of a vertebra) using an anchoring device 102 such as a bone screw. The deflection rod system 110 is connected with the anchoring device 102 by an arm 130, which arm 130 can be integrally formed with the deflection rod system 110, affixed to the deflection rod system 110 by one or more fasteners or fastening features (such as protruding structures that interlockingly engage each other when coupled), press fit to the deflection rod system 110, or otherwise fixedly secured to the deflection rod system 110. In the embodiment, the arm 130 includes an aperture 131 through which the anchoring device 102 is received and driven into the bone. The anchoring device 102 includes a head 104 that interferes with passage of the anchoring device 102 through the aperture 131. Threads 106 of the anchoring device 102 grip the bone to hold the arm 130 between the bone and the head 104, thereby affixing the arm 103 and by extension the deflection rod system 110 to the bone. Preferably, the anchoring device 102 is comprised of titanium; however, other biocompatible materials such as stainless steel and/or PEEK can be used. As will be appreciated upon reflecting on the different embodiments, the structures described herein can vary in size and shape based on factors such as material of construction, anatomical structure of the implantation site, implantation technique and targeted system performance (e.g., stiffness).

Figure 2:
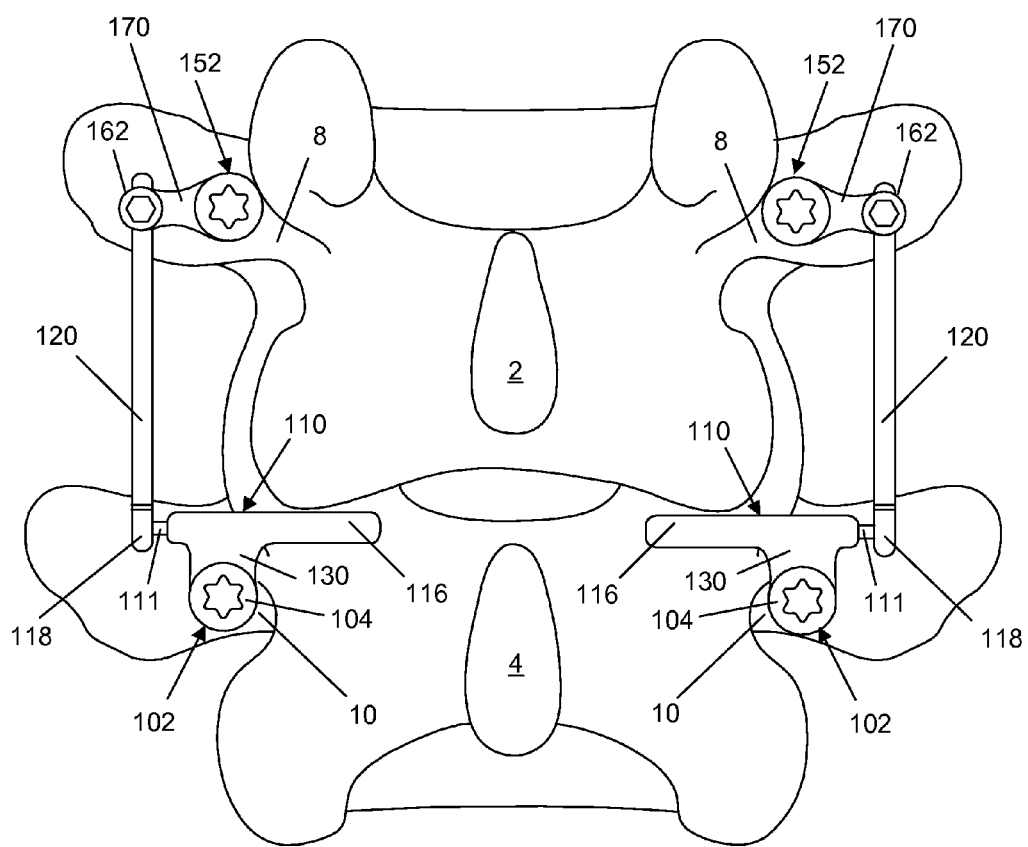
FIG. 2 is a posterior view of the dynamic spine stabilization system of FIG. 1A implanted and extending between two vertebrae of a spine.
Figure 3A:
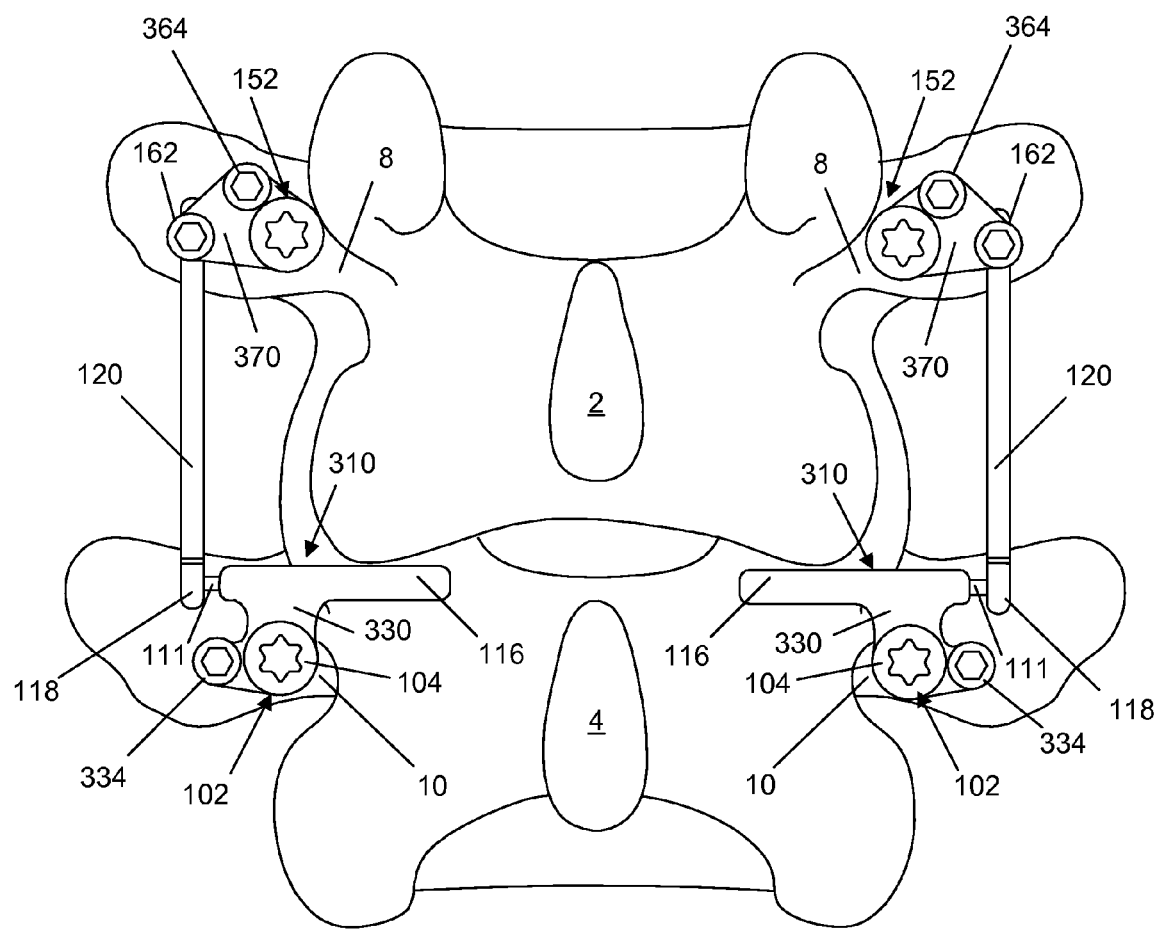
FIG. 3A is a posterior view of the dynamic spine stabilization system of FIG. 1A implanted as shown in FIG. 2 and further comprising locking screws to resist rotation of the dynamic spine stabilization system.
Figure 3B:
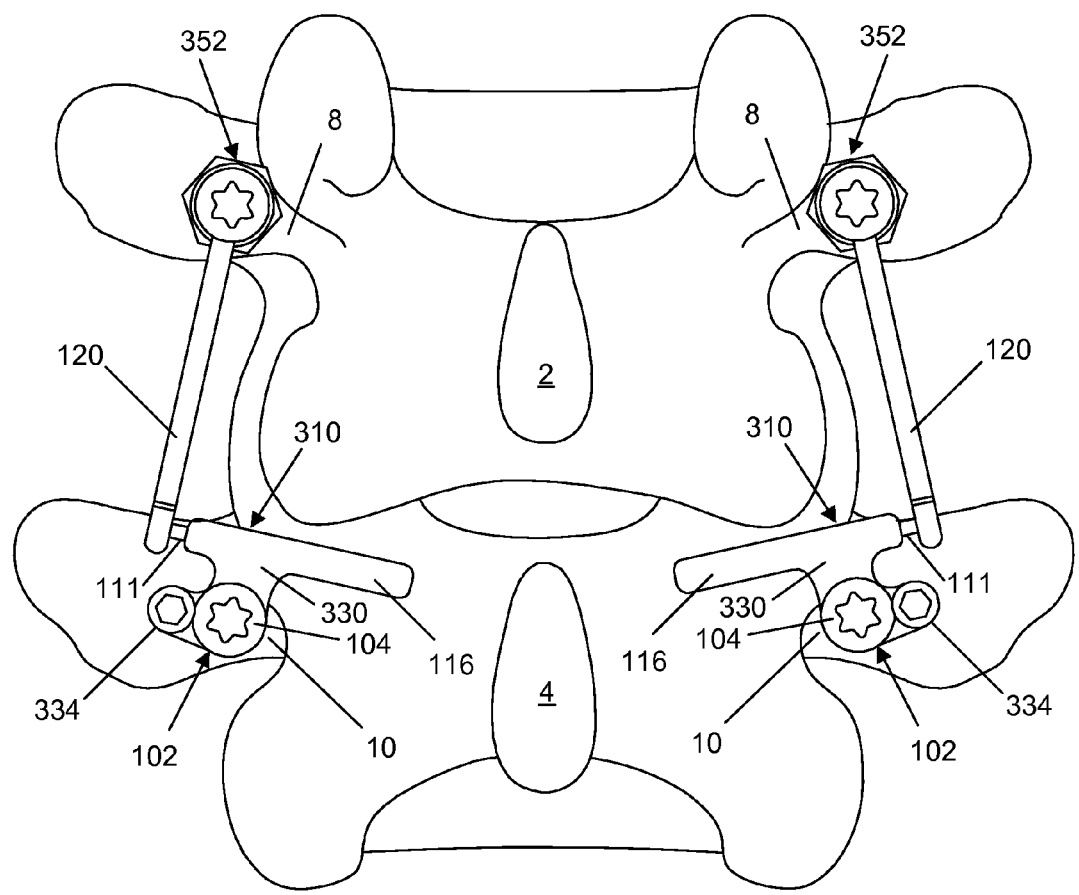
FIG. 3B is a posterior view of another embodiment of the dynamic spine stabilization system of the invention.
Figure 7A:
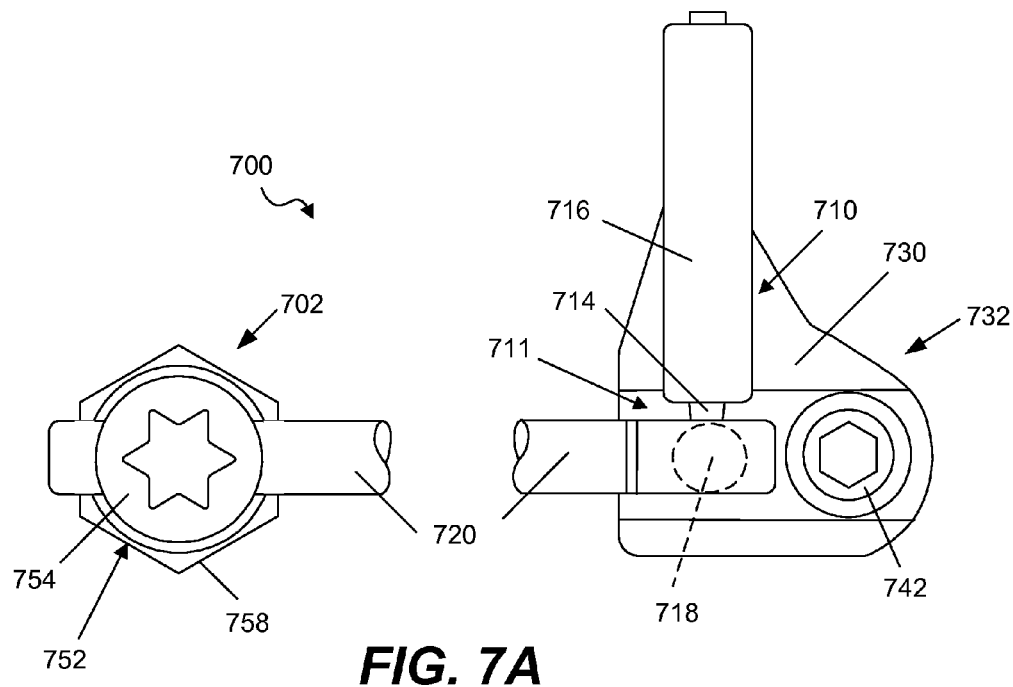
FIG. 7A is a posterior view of an alternative embodiment of a dynamic spine stabilization system in accordance with the present invention.
Figure 7B:
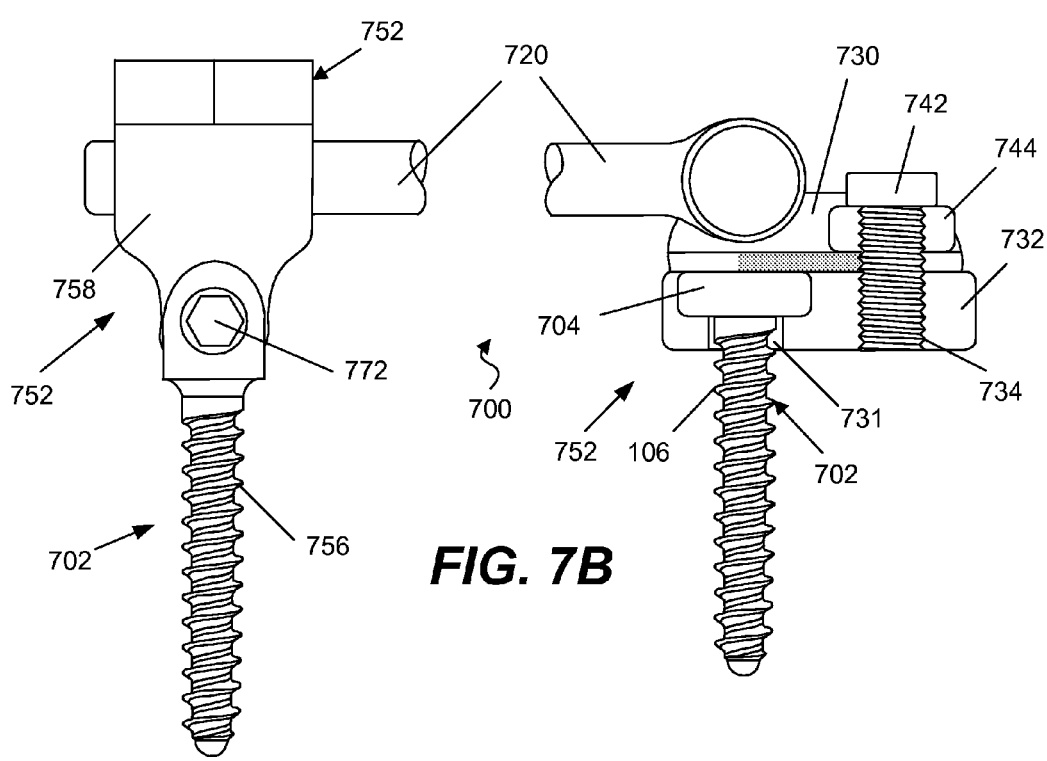
FIG. 7B is a lateral view of the dynamic spine stabilization system of FIG. 7A.

Referring to FIG. 2, the vertical rod 120 is connected to the deflection rod 111 and can urge the deflection rod 111 in response to relative movement of two vertebrae between which the vertical rod 120 extends. In the embodiment shown, a distal end of the deflection rod 111 can be fixedly mated with a spherical (or semi-spherical) ball or joint 118 that can pivot within a cradle at a proximal end of the vertical rod 120. The vertical rod 120 can pivot in a posterior-to-anterior or anterior-to-posterior direction about the joint 118, and optionally can pivot slightly in a lateral direction. The pivoting motion can allow adjustment of the vertical rod 120 relative to the deflection rod system 110 to ease manipulation of the dynamic stabilization system during implantation and optionally to reduce torque forces applied to the deflection rod 111. A distal end of the vertical rod 120 can be fixedly connected with an upper (or lower) vertebra of the two vertebrae by an additional anchoring device 152, such as a bone screw. The anchoring device 152 can include an arm 170 extending a clamp 162 that receives and secures the vertical rod 120. The arm 170 extends laterally from the anchoring device 152 so that the anchoring device 152 can be positioned and secured to the upper pedicle 8 (a good source of bone for anchoring) while the clamp 162 can be aligned with the vertical rod 120 to receive the vertical rod 120, which extends generally (though not necessarily) parallel to the spine. The dynamic stabilization system 100 comprises two substantially similar, mirrored structures connected at opposite pedicles 8,10 of the vertebrae 2,4. However, in alternative embodiments, the dynamic stabilization system can comprise dissimilar structures, for example to accommodate anatomical asymmetry. FIG. 3A illustrates an alternative embodiment wherein one or both of the deflection rod system arms 330 and clamp arm 370 can include a secondary aperture for receiving a locking screw 334,364 that can resist rotation of the corresponding arm. FIG. 3B illustrates an alternative embodiment wherein the deflection rod system arm 330 includes a secondary aperture for receiving the locking screw 334, and wherein the clamp and clamp arm are supplanted by an anchoring device 352 that receives the vertical rod 120 over a bone screw thread. The anchoring device 352 can resemble the anchoring device 752 shown in FIGS. 7A, 7B, and described below in the description of FIGS. 7A, 7B. Such anchoring devices can resemble anchoring devices described in U.S. Provisional Application 61/031,598, entitled "A DEFLECTION ROD SYSTEM FOR A DYNAMIC STABILIZATION AND MOTION PRESERVATION SPINAL IMPLANTATION SYSTEM AND METHOD" (SPART-01037US0), incorporated herein by reference. The alternative embodiment may reduce torque applied to the anchoring device 352 and simplify the anchoring device 352 to ease implantation of the anchoring device 352.

More lateral placement of the vertical rods provides for more stiffness in lateral bending and an easier implant approach by, for example, a Wiltse approach as described in "The Paraspinal Sacraspinalis-Splitting Approach to the Lumber Spine," by Leon L. Wiltse et al., *The Journal of Bone & Joint Surgery*, Vol. 50-A, No. 5, July 1968, which is incorporated herein by reference.

The stiffness of the deflection rod system 100 can preferably be adjusted by the selection of the materials and placement and diameters of the deflection rod system as well as the horizontal and vertical rods. Larger diameter rods would increase the resistance of the deflection rod system 100 to flexion, extension rotation, and bending of the spine, while smaller diameter rods would decrease the resistance of the deflection rod system 100 to flexion, extension, rotation and bending of the spine. Further, continually or discretely changing the diameter of the deflection rods 111 along the length of the deflection rods 111 changes the stiffness characteristics. Thus, with the deflection rods 111 tapered toward the vertical rod 120, the deflection rod system 100 can have more flexibility in flexion and extension of the spine. Further, using a super elastic material for the vertical rod 120 in addition to the deflection rod 111 adds to the flexibility of the deflection rod system 100. Further, the vertical rods 120, in addition to the deflection rods 111, can be made of titanium or stainless steel or PEEK should a stiffer deflection rod system 100 be required. Thus, it can be appreciated that the deflection rod system 100 can selectively accommodate the desired stiffness for the patient depending on the materials uses, and the diameter of the materials, and the placement of the elements of the deflection rod system 100.

Should an implanted deflection rod system 100 need to be revised, that can be accomplished by removing and replacing the vertical rod 120 and/or deflection rod system 110 to obtain the desired stiffness. By way of example only, should a stiffer revised deflection rod system 100 be desired, more akin to a fusion, or, in fact, a fusion, then the deflection rod system 110 having the deflection rods 111 can be removed and replaced by a deflection rod system 110 having the deflection rods 111 made of titanium, or stainless steel, or non-super elastic rods to increase the stiffness of the system. This can be accomplished in some embodiments described herein by leaving the anchoring device 102 in place and removing the existing deflection rod systems 110 and replacing the deflection rod systems with deflection rod systems having stiffer distraction rods 111 and outer shells and associated vertical rods 120.

Figure 4:
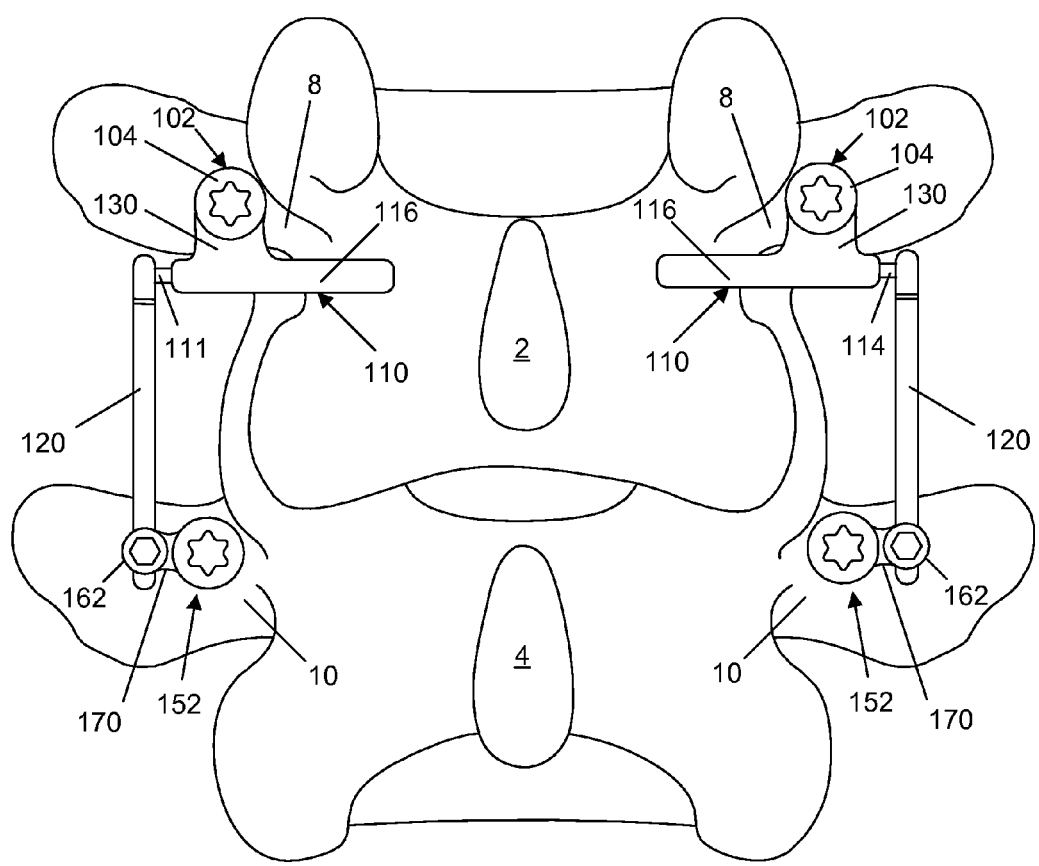
FIG. 4 is a posterior view of another embodiment of the dynamic spine stabilization system of the invention.
Figure 5:
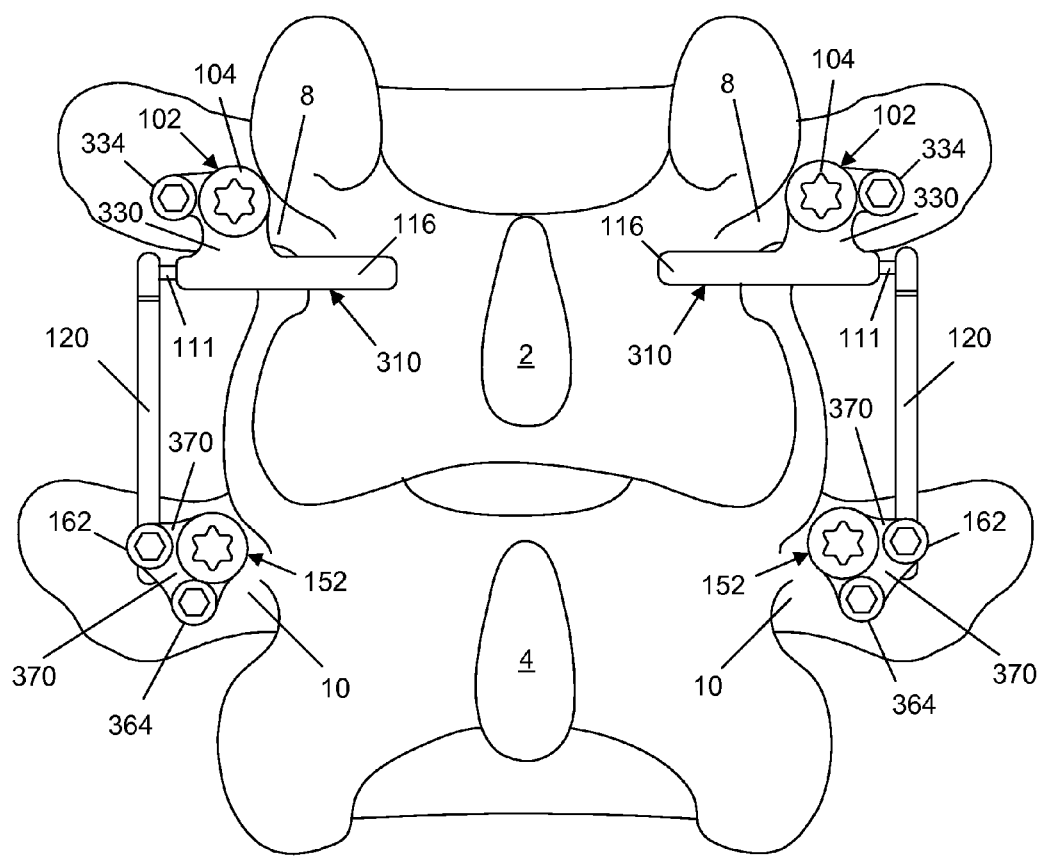
FIG. 5 is a posterior view of another embodiment of the dynamic spine stabilization system of the invention.
Figure 6:
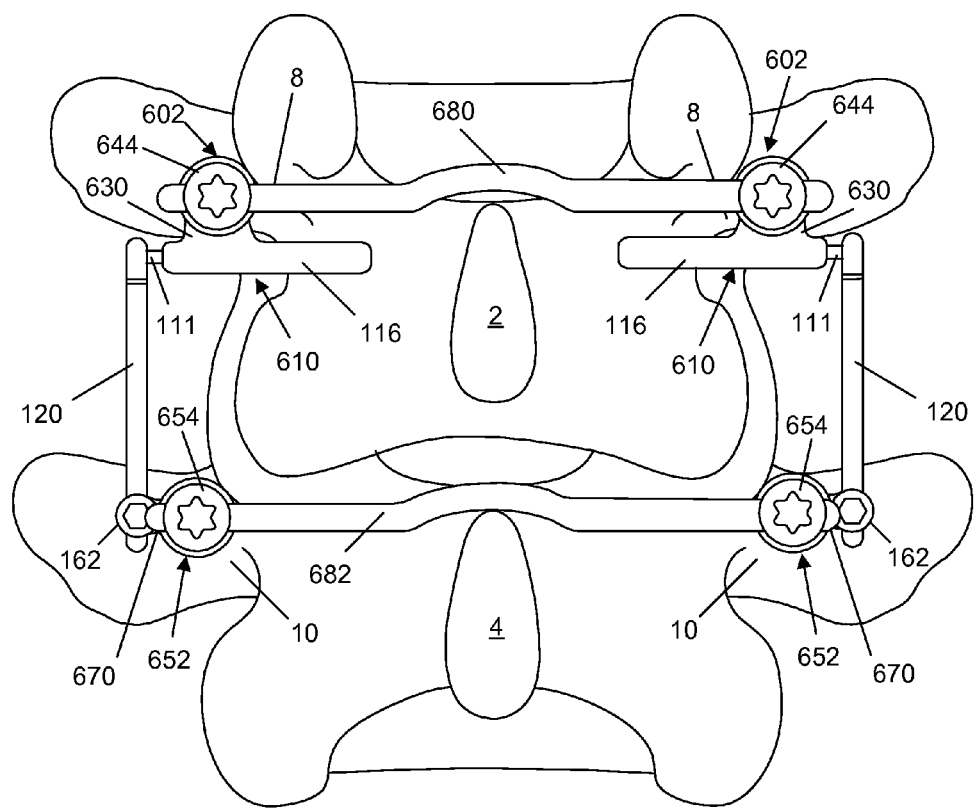
FIG. 6 is a posterior view of yet another embodiment of the dynamic spine stabilization system of the invention including horizontal rods to resist rotation.

In alternative embodiments of methods of stabilizing vertebral motion segments in accordance with the present invention, the dynamic stabilization system 100 can be implanted in an arrangement vertically flipped from the arrangement of FIG. 2. As shown in FIG. 4, the deflection rod system 110 is fixedly connected with the upper vertebra by the anchoring system 102. The vertical rod 120 is connected to the deflection rod 111 and extends caudally to the lower vertebra. The vertical rod 102 urges the deflection rod 111 in response to relative movement of the two vertebrae between which the vertical rod 120 extends. As with the previously described arrangement and as shown in FIG. 5, one or both of the deflection rod system arms 330 and clamp arms 370 can include a secondary aperture for receiving a locking screw 334, 364 that can resist rotation of the corresponding arm. Referring to FIG. 6, in still further embodiments, one or both of the deflection rod system arms 630 and clamp arms 670 can be adapted to connect with horizontal rods 680, 682 that extend between pedicles 8,10 of a vertebra. The anchoring devices 602, 652 can include a U-shaped channel for receiving the horizontal rod 680, 682, the horizontal rod being held in the channel by a locking set screw 644, 654. The horizontal rods 680, 682 are positioned between adjacent spinous processes 2, 4 associated with the vertebrae and can pierce or displace the interspinal ligament without severing or removing tissue. The horizontal rods 680, 682 can resist rotation and can be used in place of locking screws. In a preferred embodiment, the horizontal rod 680,682 can be comprised of titanium, stainless steel or PEEK or another biocompatible material, and the first and second deflection rods or loading rods can be comprised of a super elastic material. Preferably, the super elastic material is comprised of Nitinol (NiTi). In addition to Nitinol or nickel-titanium (NiTi), other super elastic materials include copper-zinc-aluminum and copper-aluminum-nickel. However, for biocompatibility, the nickel-titanium is the preferred material.

FIGS. 7A-9 illustrate a still further embodiment of a deflection rod system 700 in accordance with the present invention comprising an deflection rod system 710 connectable with an anchoring device 702 after the anchoring device 702 is secured to a pedicle. Such embodiments can reduce visual obstruction of the pedicle during seating of the anchoring device 702 by reducing the size of the structure seated. An anchoring block 732 receives the anchoring device 702 through an aperture 731 and is secured to the pedicle as threads 106 of the anchoring device 702 grip the bone and the head 704 is seated within the anchoring block 732. The anchoring block 732 includes an internal screw thread 734 through at least a portion of the anchoring block 732 for receiving a screw 742 to secure an deflection rod system arm 730 of the deflection rod system 710. As in previous embodiments, the deflection rod system 710 comprises a deflection rod shield or guide 716 and a deflection rod 711 including an inner rod (not visible) within an outer shell 714. As shown, the deflection rod system 710 is connected with an arm 730 having a curved base that meets a curved surface of the anchoring block 732 (FIG. 7C). The arm 730 can pivot slightly relative to the anchoring device 702, allowing the surgeon to adjust an angle of protrusion of the deflection rod system 710 relative to the spine. The arm 730 is fastened to the anchoring block 732 by the screw 742 which is connected through a spacer 744 having a surface in sliding contact with a curved surface of the arm 730 to distribute force generally evenly along the arm 730 when arranged at a desired orientation. In this arrangement, preferably, the joint 718 is adjacent with and located over the anchor 702 in order to minimize or eliminate the transfer of torque forces from the rod 720 to the anchor 702. Other complementary mating surfaces may be used to obtain the desired relative motion.

Figure 8:
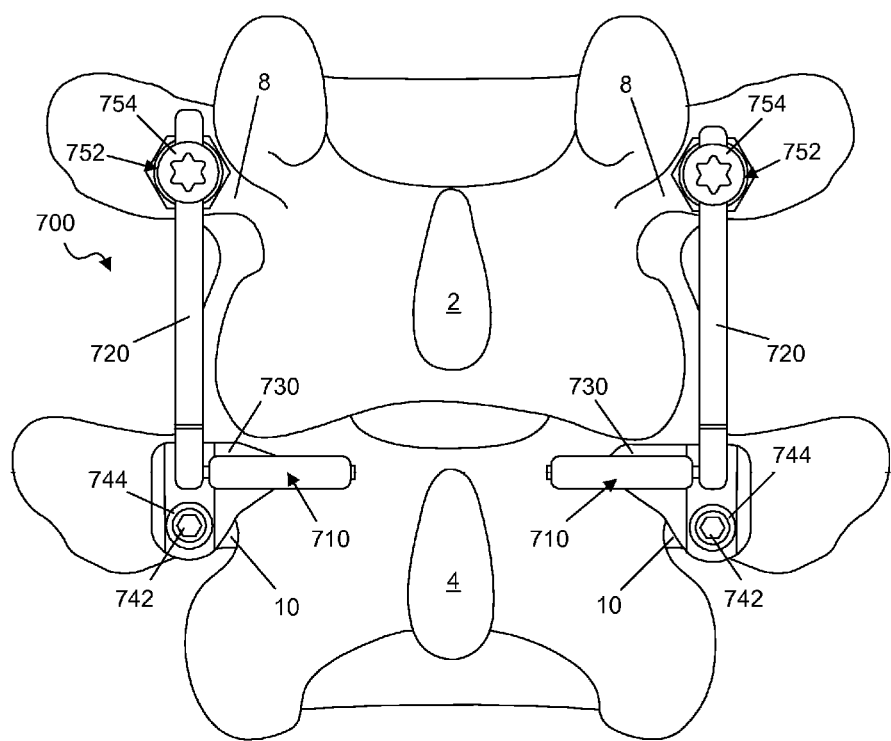
FIG. 8 is a posterior view of the dynamic spine stabilization system of FIG. 7A implanted and extending between two vertebrae of a spine.
Figure 9:
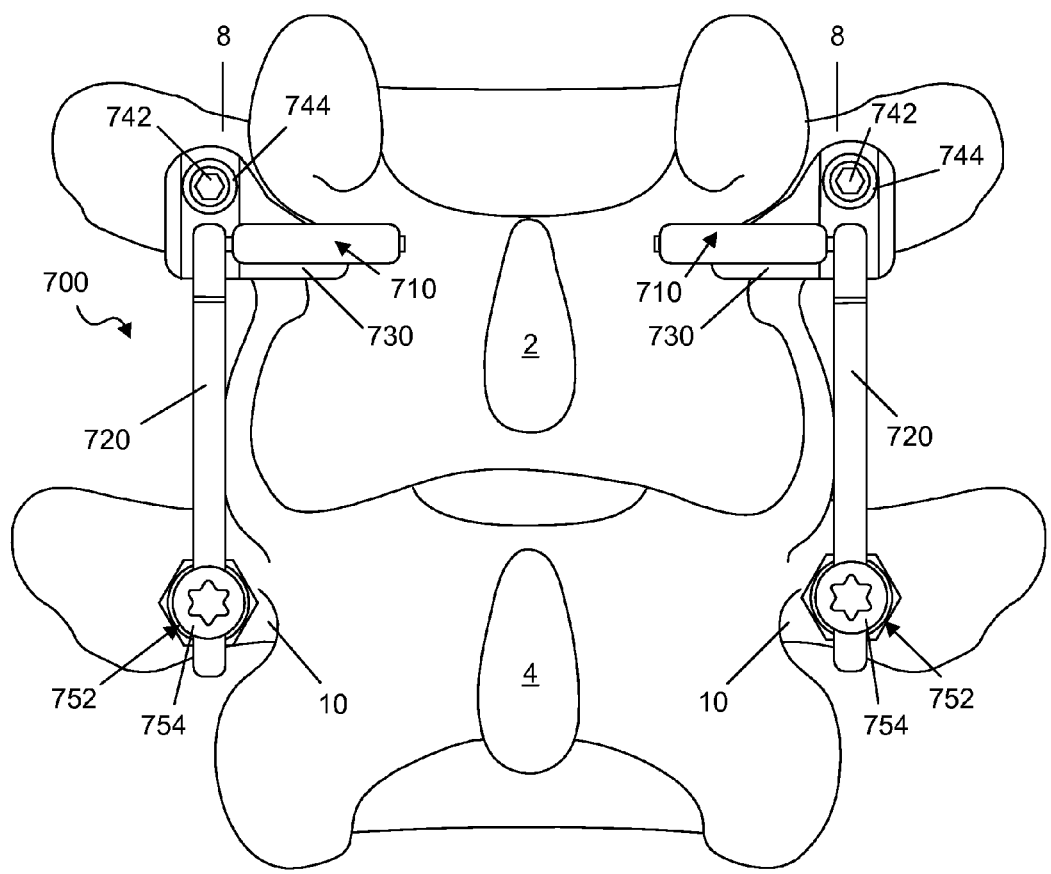
FIG. 9 is a posterior view of the dynamic spine stabilization system of FIG. 7A implanted in an alternative arrangement to FIG. 8 and extending between the two vertebrae.

A vertical rod 720 is connected to the deflection rod 711 and can urge the deflection rod 711 in response to relative movement of two vertebrae between which the vertical rod 720 extends. A distal end of the deflection rod 711 can be fixedly mated with a spherical (or semi-spherical) ball or joint 718 that can pivot within a cradle at a proximal end of the vertical rod 720. The vertical rod 720 can pivot in a posterior-to-anterior or anterior-to-posterior direction about the joint 718, and optionally can pivot in a lateral direction. The pivoting motion can allow adjustment of the vertical rod 720 relative to the deflection rod system 710 to ease manipulation of the dynamic stabilization system during implantation and optionally to reduce torque forces applied to the deflection rod 711. A distal end of the vertical rod 720 can be fixedly connected with an upper or lower vertebra of the two vertebrae by an additional anchoring device 752. The anchoring device can resemble anchoring devices as described in U.S. Provisional Application No. 61/031,598. As shown, the anchoring device 752 includes a saddle 758 that can receive the vertical rod 720. A locking set screw 754 can be urged along threads of the saddle 758 so that the locking set screw 754 secures the vertical rod 758 against the U-shaped channel of the saddle 758. A bone screw thread 756 can optionally be mated with a body of the anchoring device 752 by a fastener 772 that permits at least cranial-to-caudal pivoting. The saddle 758 can include a hex-shaped outer surface to assist in seating the bone screw 756 within the upper pedicle 8. As shown in FIGS. 8 and 9, the deflection rod system 700 can be arranged with the deflection rod system 710 anchored to an upper of two vertebrae, or alternatively, the lower of two vertebrae.

Figure 10:
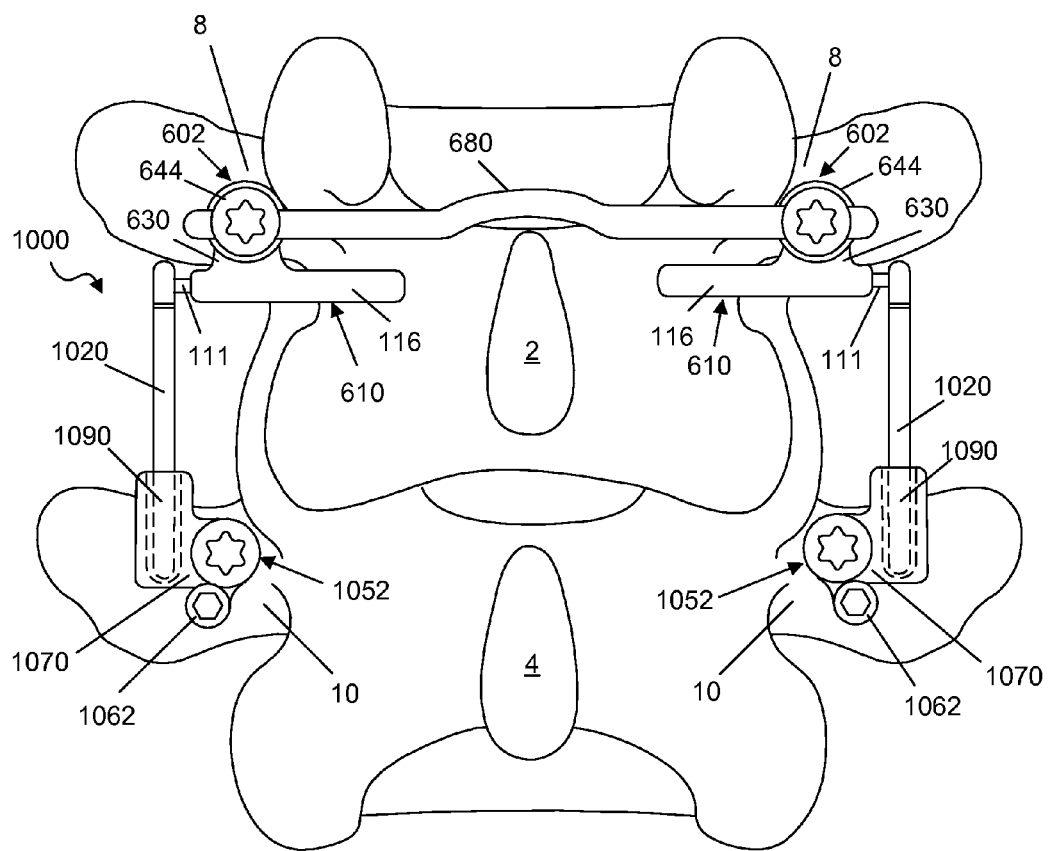
FIG. 10 is a posterior view of yet another embodiment of a dynamic spine stabilization system in accordance with the present invention implanted and extending between two vertebrae of a spine.

FIG. 10 is a posterior view of a still further embodiment of a deflection rod system implant 1000 in accordance with the present invention comprising an deflection rod system 610 that is engaged during spine extension, but not engaged during spine flexion. The deflection rod system 610 and associated structures resemble the deflection rod system and associated structures of FIG. 6, and can be connected with a horizontal rod 680 extending between pedicles of a vertebra. A vertical rod 1020 is connected at a proximal end to a deflection rod 111 of the deflection rod system 610. The distal end of the vertical rod 1010 is unattached and slides within a boot 1090. The boot 1090 blocks movement of the vertical rod 1020 when the distal end of the vertical rod 1020 abuts the base of the boot 1090, and further extension movement will cause the vertical rod 1020 to deflect the deflection rod 111. The boot 1090 is preferably sized to accommodate movement of vertical rod 1020 within the boot 1090 that spans a length of natural movement of the spine during extension, to avoid separation of the vertical rod 1020 from the boot 1090. Alternatively, the distal end of the vertical rod can include a ball or other slidable structure that is held within a cavity of the boot, enabling the boot to resist both extension and flexion, and to permit a range of free motion determined by the surgeon. As shown, the boot 1090 is connected with an anchoring device 1052 by an arm 1070. A locking screw 1062 resists rotation of the boot 1090 about the anchoring device 1052 in response to a force applied by the vertical rod 1020.

Figure 11A:
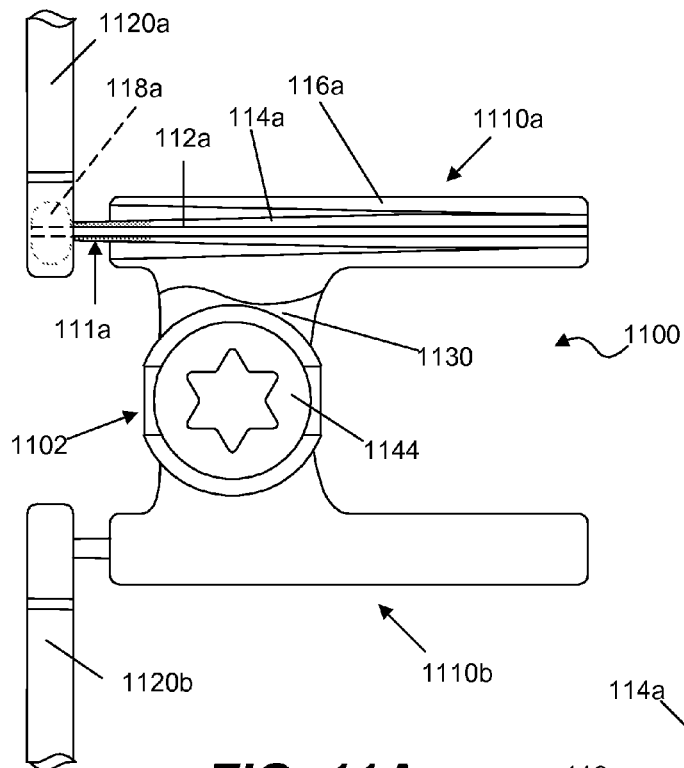
FIG. 11A is a posterior view of an alternative embodiment of a dynamic spine stabilization system in accordance with the present invention.
Figure 11B:
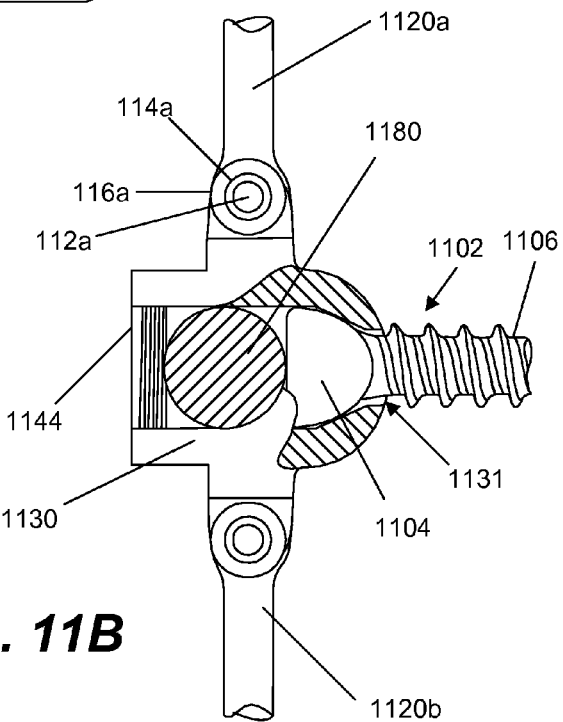
FIG. 11B is a lateral view of the dynamic spine stabilization system of FIG. 11A.

FIG. 11A is a posterior view (in partial cross-section) and FIG. 11B is a lateral view (in partial cross-section) of a still further embodiment of a deflection rod system implant 1100 for use with dynamic stabilization systems accordance with the present invention. The deflection rod system implant 1100 is adapted to support multiple motion segments and comprises a first deflection rod system 1110*a* connected with a vertical rod 1120*a* extending cranially, a second deflection rod system 1110*b* connected with a vertical rod 1120*b* extending caudally, and an anchoring device 1102. The first and second deflection rod systems 1110*a*, 1110*b* can have similar or different bending or load carrying or stiffness characteristics, as prescribed by the surgeon or a physician. A common arm 1130 connects the first and second deflection rod systems 1110*a*, 1110*b* with the anchoring device 1102. The arm 1130 includes an aperture 1131 through which the anchoring device 1102 is received and driven into the bone. The anchoring device 1102 includes a head 1104 that interferes with passage of the anchoring device 1102 through the aperture 1131. Threads 1106 of the anchoring device 1102 grip the bone to hold the arm 1130 between the bone and the head 1104, thereby affixing the arm 1103 and by extension the deflection rod systems 1110*a*, 1110*b*. The arm 1130 can be adapted to connect with a horizontal rod 1180 that extend between pedicles 10 of a vertebra. The horizontal rod 1180 can be received in U-shaped slots of the arm 1130 and urged against the head 1104 of the anchoring device 1102 by a locking set screw 1144 having external threads that mate with internal threads of the walls of the arm channel.

Figure 12:
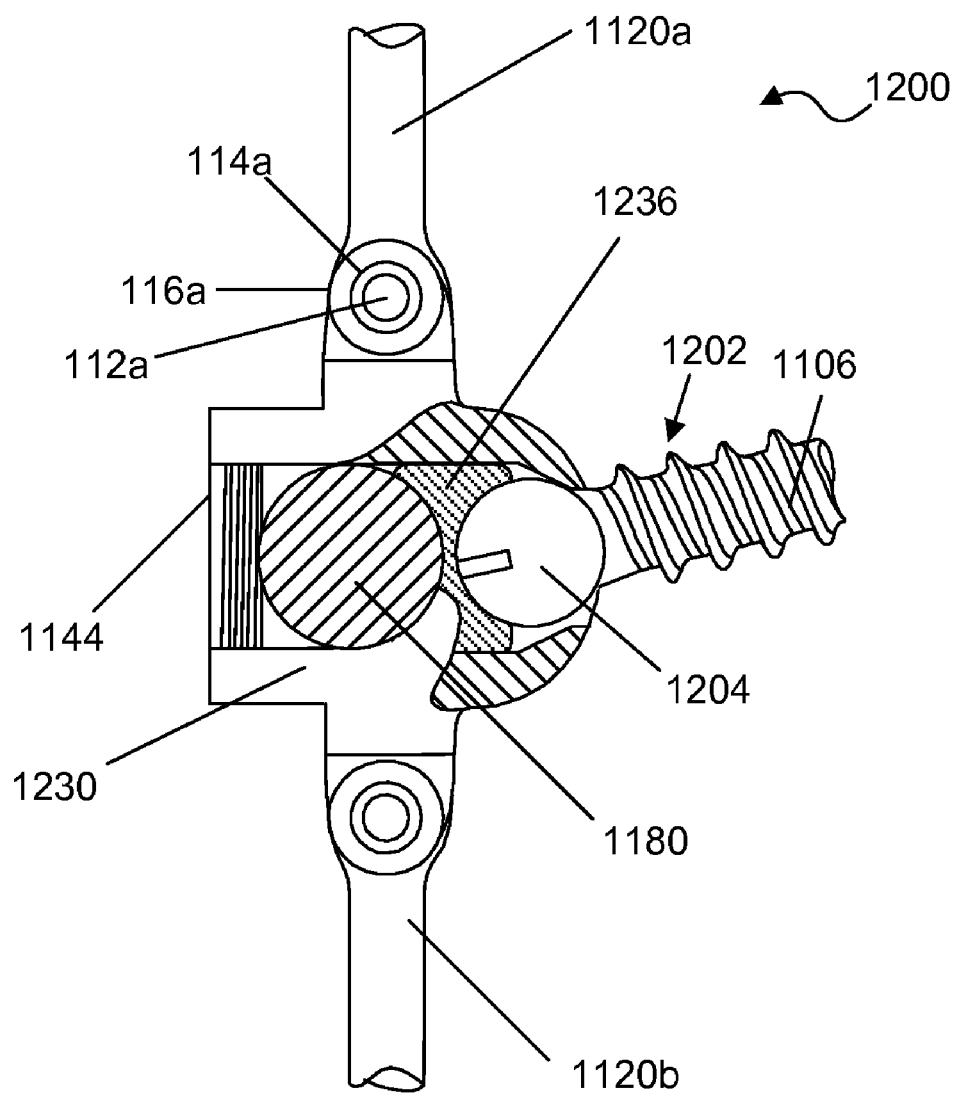
FIG. 12 is a lateral view of the dynamic spine stabilization system of FIG. 11A comprising an alternative seating arrangement for a horizontal rod.

FIG. 12 is a lateral view of a deflection rod system implant 1200 resembling the deflection rod system implant 1100 of FIG. 11B with a compressor element or cradle 1236 positioned within the channel and between the horizontal rod 1180 and anchoring device 1202. As shown, the head 1204 of the anchoring device 1202 has a spherical or semi-spherical shape, although alternatively the head can have some other shape that complements the compressor element or cradle 1236 while permitted at least limited movement between the two structures to allow flexibility in relative arrangement during implantation. For example, the head can have a rounded indention mateable with a spherical surface.

The compressor element or cradle 1236 has a generally cylindrical body so that the compressor element 1236 can fit within a bore of the arm 1230. A posterior surface of the compressor element 1236 is concave and generally complementing the horizontal rod 1180 which rests thereon. The anterior surface of the compressor 1236 is in sliding contact with the head 1204 to allow the anchoring device 1202 to be positioned as appropriate. The locking set screw 1144 urges the horizontal rod 1180 against the compressor element 1236, which in turn is urged against the anchoring device 1202. Alternatively, the compressor element 1236 and head 1204 can have some other complementary shape that allows some or no sliding contact between the structures.

Figure 13:
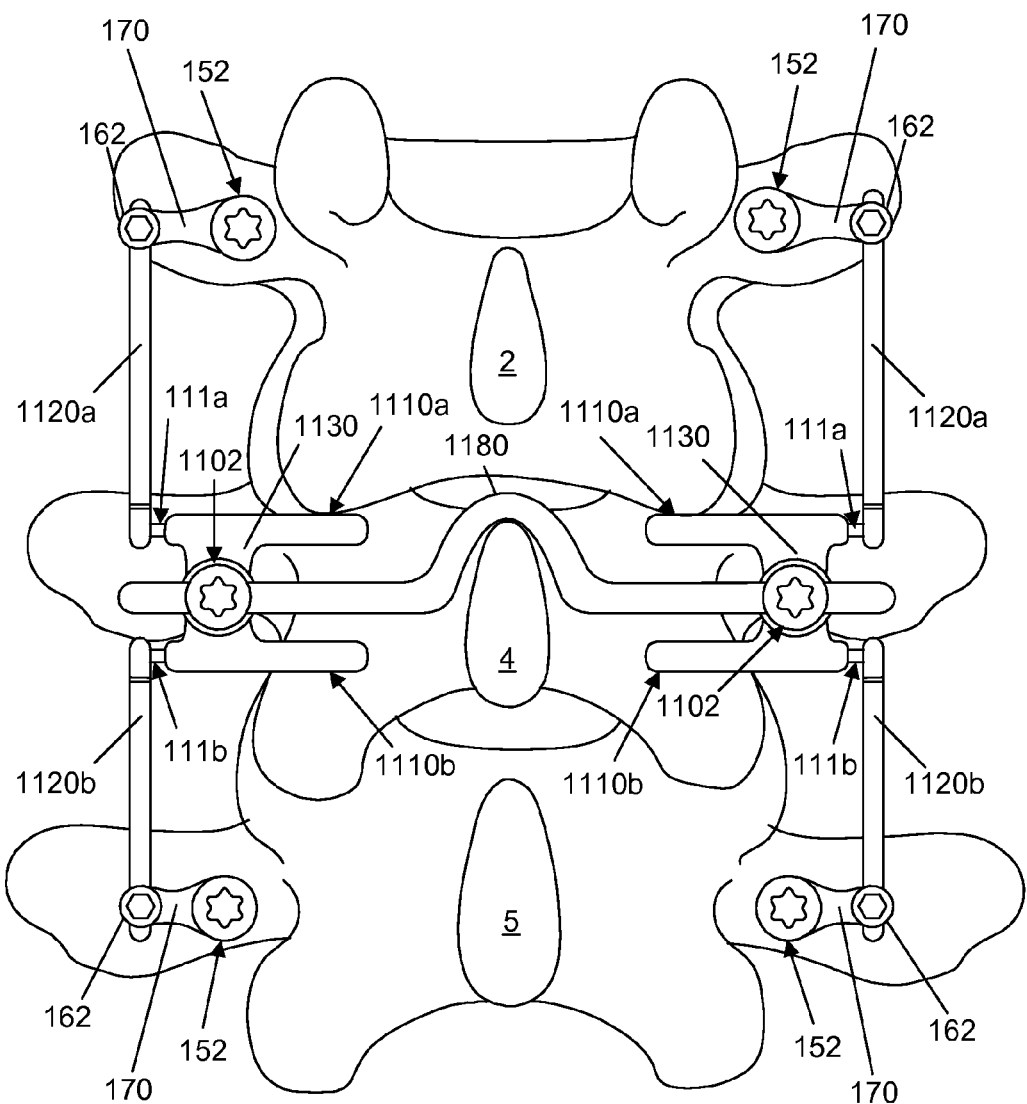
FIG. 13 is a posterior view of the dynamic spine stabilization system of FIG. 11A implanted and extending between a vertebra of the spine and two adjacent vertebrae.

FIG. 13 is a posterior view of the deflection rod system implant 1200 of FIG. 11 comprising the first deflection rod system 1110a and second deflection rod system 1110b secured to a vertebra common to two adjacent motion segments targeted for stabilization by an anchoring device 1102. A first vertical rod 1120a is connected to a deflection rod 1111a of the first deflection rod system 1110a and extends cranially to the upper vertebra of the upper targeted motion segment, and is secured to the upper vertebra by a clamp 162. A second vertical rod 1120b is connected to a deflection rod 1111b of the second deflection rod system 1110b and extends caudally to the lower vertebra of the lower targeted motion segment, and is secured to the lower vertebra by a clamp 162. The vertical rods 1120a, 1120b urge respective deflection rods 1111a, 1111b in response to relative movement of the two vertebrae between which the vertical rods 1120a, 1120b extend. Preferably, vertical rod 1120a is aligned with vertical rod 1120b in order to reduce or eliminate torque forces. An arm 1130 common to the deflection rod systems 1110a, 1110b is connected with a horizontal rod 1180 that extends between pedicles of the common vertebra to a complementary pair of deflection rod systems. The horizontal rod 1180 is positioned between adjacent spinous processes 2,4 associated with the vertebrae and can pierce or displace the interspinal ligament without severing or removing tissue. The horizontal rod 1180 can resist rotation of the deflection rod systems 1110a,1110b and can be used in place of locking screws.

FIGS. 14A and 14B illustrate yet another embodiment of a deflection rod system implant 1400 in accordance with the present invention comprising an deflection rod system 1410 connectable with an anchoring device 1402, preferably after the anchoring device 1402 is secured to a pedicle. An arm 1430 of the deflection rod system 1410 comprises a collar 1464 that can be received over a head 1404 of the anchoring device 1402 to capture a horizontal bar 1480. The arm 1430 can be secured to the head 1404 by a collar screw 1450. The horizontal bar 1480 can be held in place by one or both of the arm 1430 which is urged against the horizontal bar 1480 by the collar screw 1450, and a locking set screw 1458. Optionally, the head 1404 of the anchoring device can be connected with a yoke 1407 by a pin 1403 to allow the head 1404 to be pivoted during implantation. Such an arrangement can allow a thread 106 of the anchoring device 1402 to be seated within the pedicle at an acute angle relative to a plane of the collar.

Figure 14:
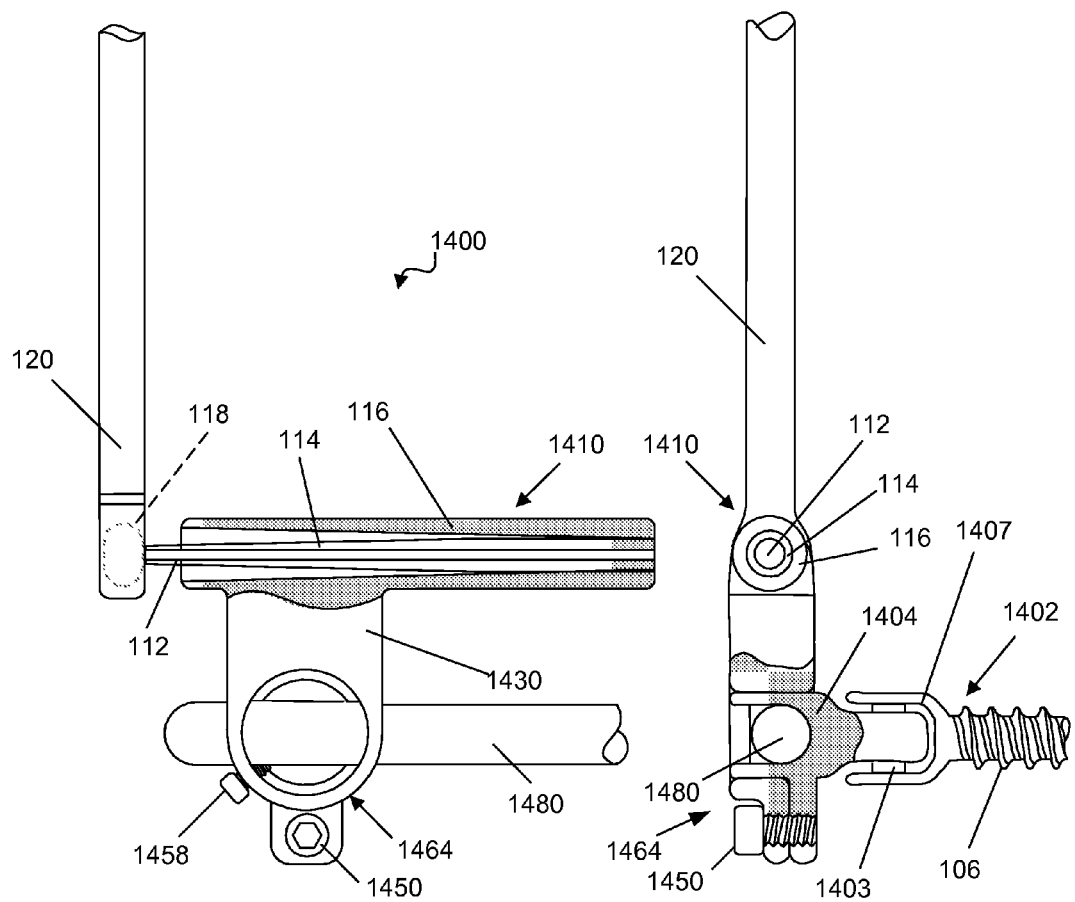
FIG. 14A is a posterior view of an alternative embodiment of a dynamic spine stabilization system in accordance with the present invention.
FIG. 14B is a lateral view of the dynamic spine stabilization system of FIG. 14A.
Figure 15:
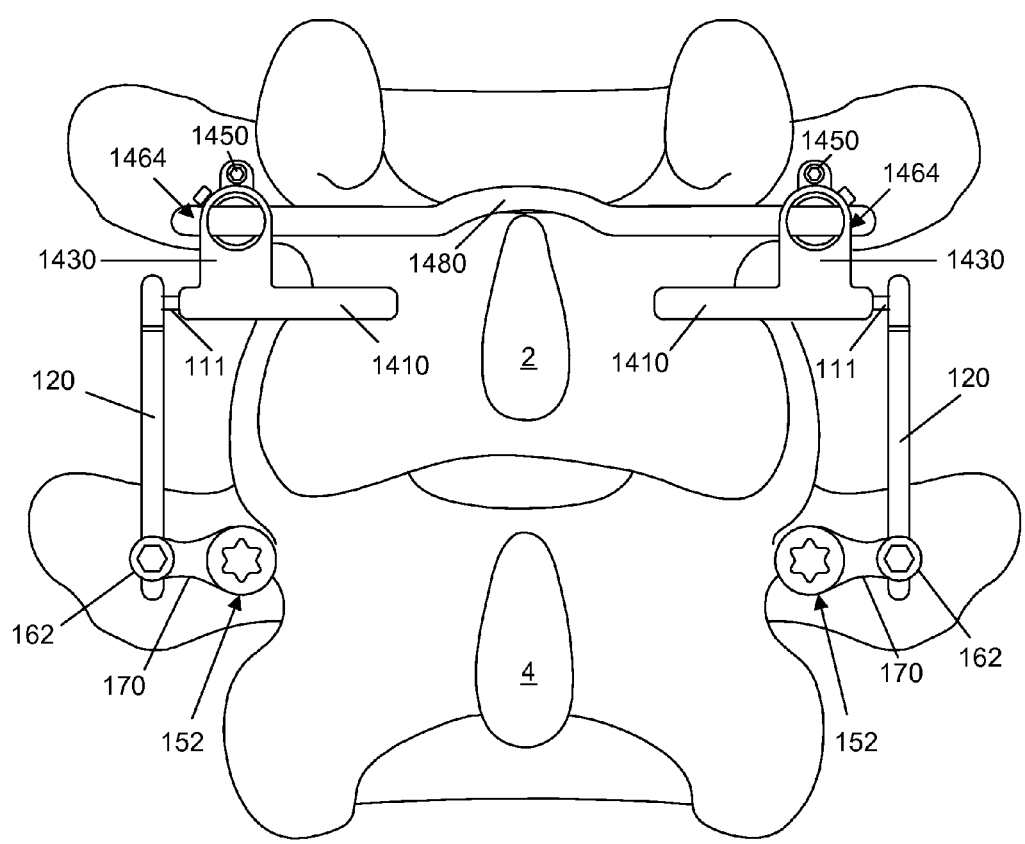
FIG. 15 is a posterior view of the dynamic spine stabilization system of FIG. 14A implanted and extending between two vertebrae of a spine.
Figure 16:
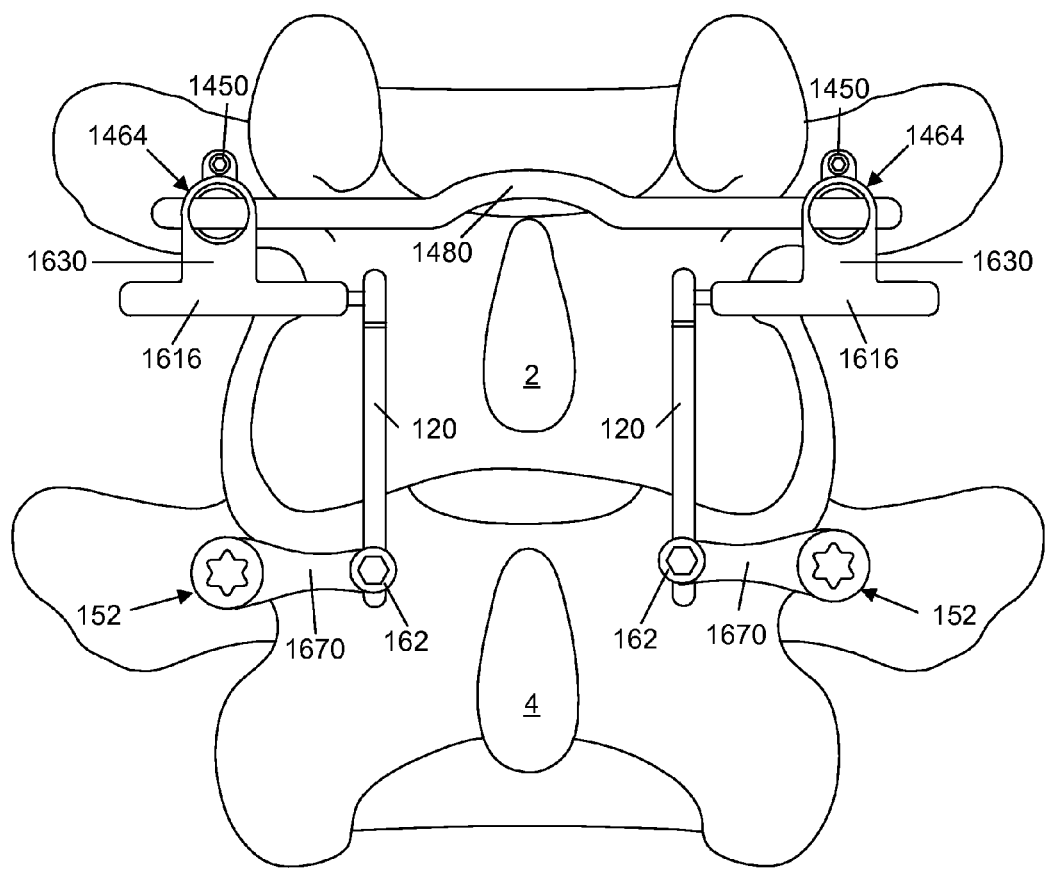
FIG. 16 is a posterior view of yet another embodiment of a dynamic spine stabilization system in accordance with the present invention implanted and extending between two vertebrae of a spine.

Referring to FIG. 15, the deflection rod system implant 1400 of FIGS. 14A and 14B is shown implanted between two vertebrae to stabilize the motion segment associated with the vertebrae. The deflection rod system 1410 is anchored to the upper vertebra of the motion segment and a vertical rod 120 is connected between a deflection rod 111 of the deflection rod system 1410 and a clamp 162 connected with the lower vertebra by an anchoring device 152. FIG. 16 is a posterior view of a still further embodiment of a deflection rod system implant 1600 in accordance with the present invention comprising an deflection rod system 1610 connected with an arm 1630 that resembles the arm 1430 of FIG. 14A-15; however, the deflection rod system 1610 is connected with the arm 1630 so that the deflection rod 111 extends toward the spinous process 2 rather than away from the spinous process (i.e., the deflection rod system 1610 is "inboard). The clamp 162 is connected with the anchoring device 152 by a clamp arm 1670 that likewise extends toward a spinous process 4.

The embodiments described above comprise deflection rods extending generally in a transverse direction to the orientation of the bone anchor screw. In still other embodiments, deflection rod systems can be oriented generally in a co-axial or collinear or parallel orientation to a bone anchor screw. Referring to FIGS. 17-22, the deflection rod system can extend substantially co-axial or parallel to the threaded shaft of an anchoring device. As will be appreciated upon reflecting on the teaching provided herein, such embodiments can simplify implantation, reduce trauma to structures surrounding an implantation site, and reduce system components.

Figure 17:
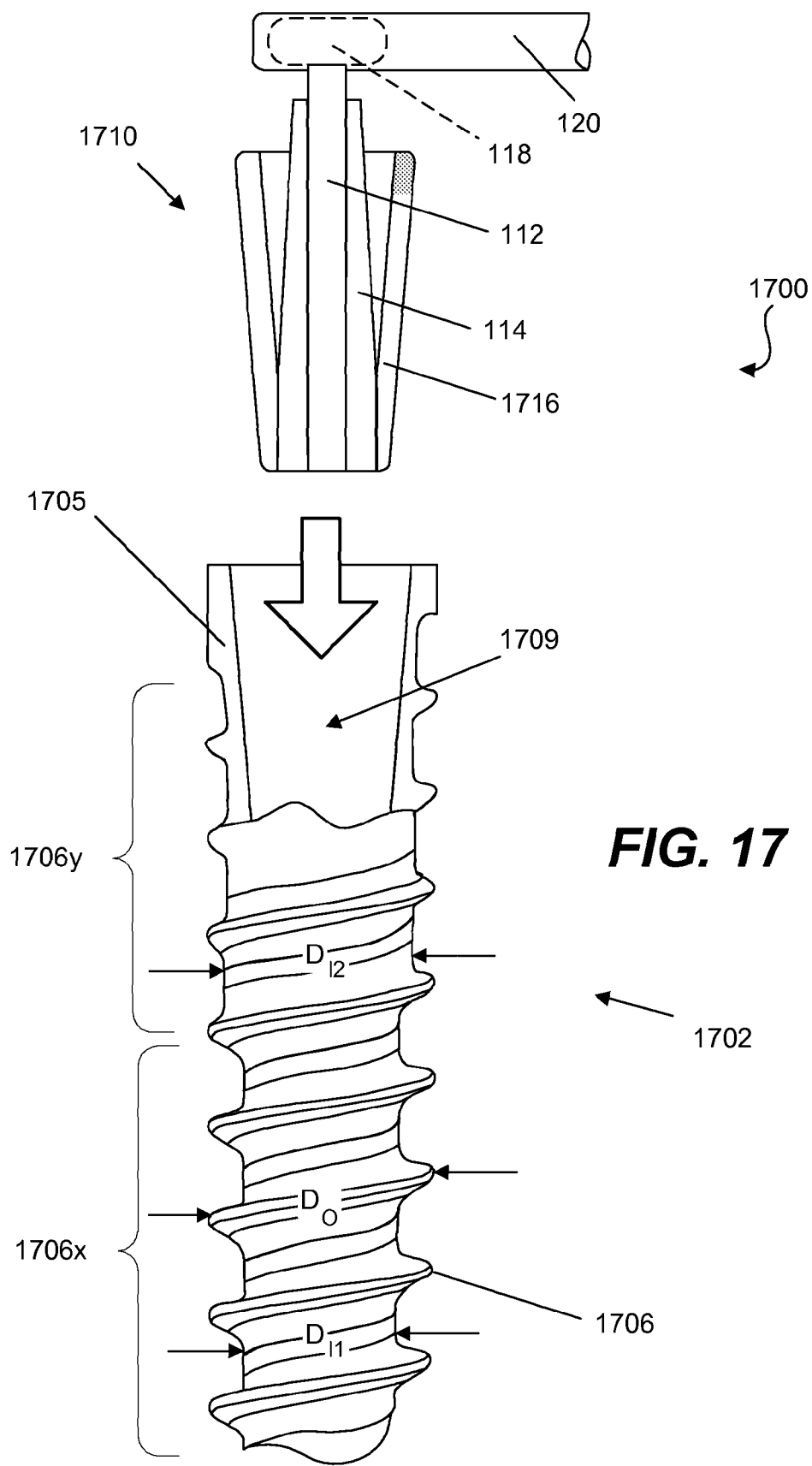
FIG. 17 is a lateral view of a further embodiment of a dynamic spine stabilization system in accordance with the present invention.

FIG. 17 illustrates an embodiment of a deflection rod system implant 1700 comprising an anchoring device 1702 with a cavity 1709 for receiving a deflection rod system 1710. It has been observed that acceptable anchoring can be achieved in a bone such as a pedicle using a thread 1706 pattern that include deep threads 1706x (i.e., having a maximum difference between inner diameter, $D_{I1}$, and outer diameter, $D_O$, of a shaft of the anchoring device) nearer the distal end of the shaft and comparatively shallow threads 1706y nearer the shank 1705. The comparatively shallow threads 1706y can enable a larger inner diameter, $D_{I2}$, of the anchoring device 1702 shaft which can accommodate the deflection rod system 1710. In some embodiments, the cavity can have a size and shape that can accommodate deflection rod systems having a range of different performance characteristics (e.g., stiffness, range of motion). A physician or surgeon can implant an anchoring device 1702 selected independently from the deflection rod system 1710 and based on the anatomy into which it is implanted. For example, the anchoring device 1702 can be selected based on the location of the vertebrae (e.g., L5-S1 vs. C7-T1) or the age and sex of the patient. The deflection rod system 1710 can then be selected based on the desired performance characteristics. The deflection rod system 1710 can be seated within the cavity using myriad different techniques. For example, the distraction rod guide or shield 1716 can be press fit into the walls of the cavity 1709, or the distraction rod guide 1716 can be cemented or otherwise adhesively fixed to the walls of the cavity 1709. Alternatively, the distraction rod guide or shield 1716 can be captured in the cavity 1709 by a locking set screw or ratchet feature. Further, the distraction rod guide 1716 (and deflection rod system 1710) can have a length longer than that of the cavity 1709 so that a portion of the distraction rod guide 1716 extends outside of the cavity 1702 and posterior to the anchoring device 1702. One of ordinary skill in the art, upon reflecting on the teachings provided herein, will appreciate the myriad ways in which the deflection rod system 1710 can be fixedly associated with an anchoring device 1702.

The distraction rod system 1700 of FIG. 17 generally includes less, or simpler footprint than the previously described embodiments, potentially reducing the amount of displacement of tissue and/or bone, reducing trauma to tissue and/or bone during surgery. Further, the smaller footprint can reduce the amount of tissue that needs to be exposed during implantation. Still further, arranging the deflection rod system 1710 co-axial with a shaft of the anchoring device 1702 can substantially transfer a moment force applied by the deflection rod system 1710 from a moment force tending to pivot or rotate the anchoring device 1702 about the axis of the shaft, to a moment force tending to act perpendicular to the axis of the shaft. The distraction rod system implant 1700 can effectively resist repositioning of the deflection rod system 1710 and/or anchoring device 1702 without the use of locking screws or horizontal bars to resist rotation. Eliminating locking screws and/or horizontal bars can reduce exposure of tissue and/or bone to foreign bodies.

Figure 18:
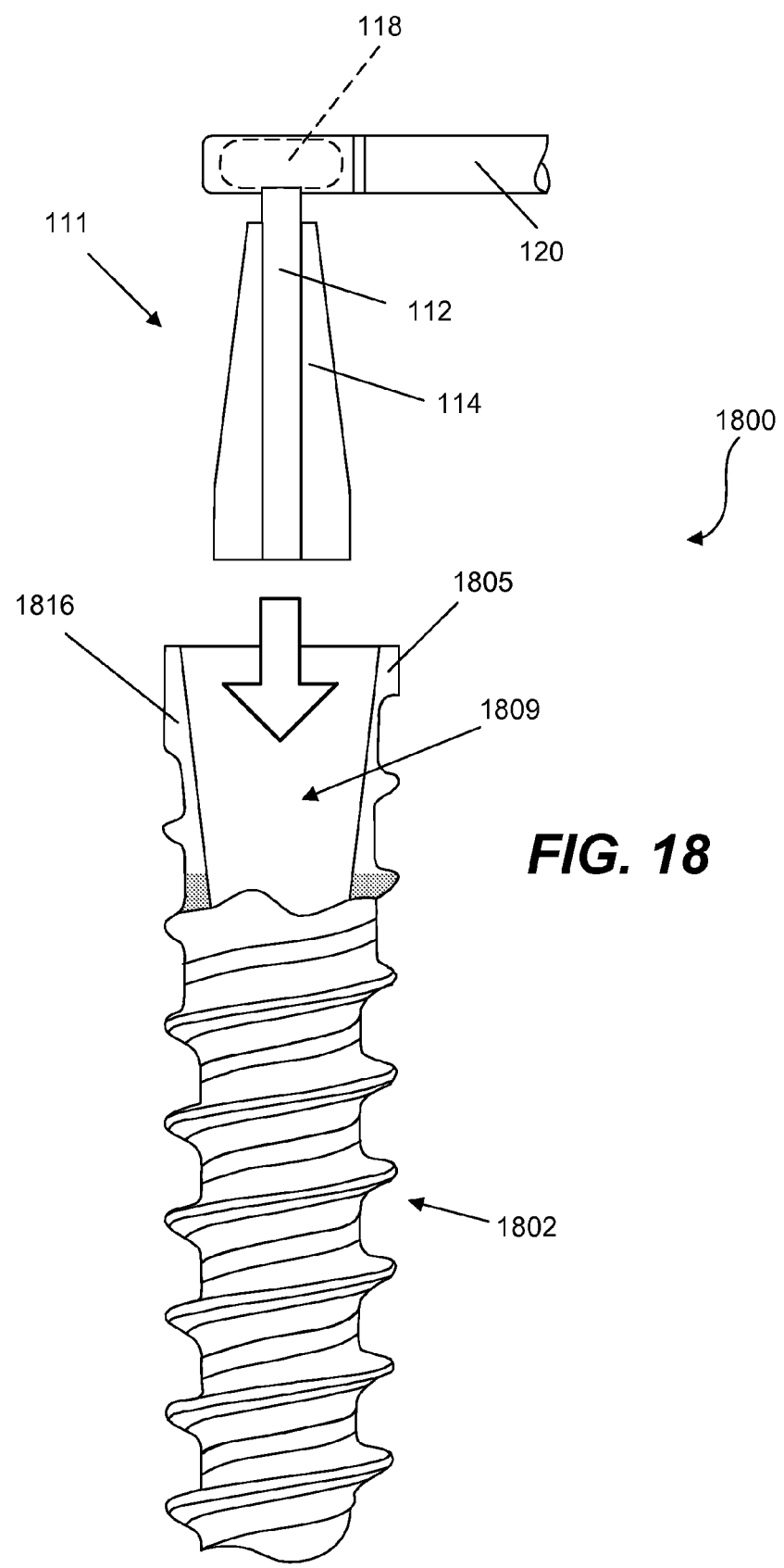
FIG. 18 is a lateral view of yet another embodiment of a dynamic spine stabilization system in accordance with the present invention.

FIG. 18 illustrates an alternative embodiment of a deflection rod system implant 1800 comprising an anchoring device 1802 with a cavity 1809 for receiving a distraction rod 111. The embodiment resembles the deflection rod system 1700 of FIG. 17; however, the distraction rod guide or shield 1816 is integrally formed in a shank 1805 of the anchoring device 1802. The distraction rod guide or shield 1816 can be sized and shaped to provide, in combination with the choice of inner rod 112 and outer shell 114, a desired performance characteristic. Integrally forming the distraction rod guide 1816 in a shank 1805 of the anchoring device 1802 can potentially reduce a thickness otherwise required to accommodate separate components. The distraction rod 111 can be mated with the distraction rod guide 1816 applying similar techniques to mate distraction rods within previously described distraction rod guide or shield.

Figure 19:
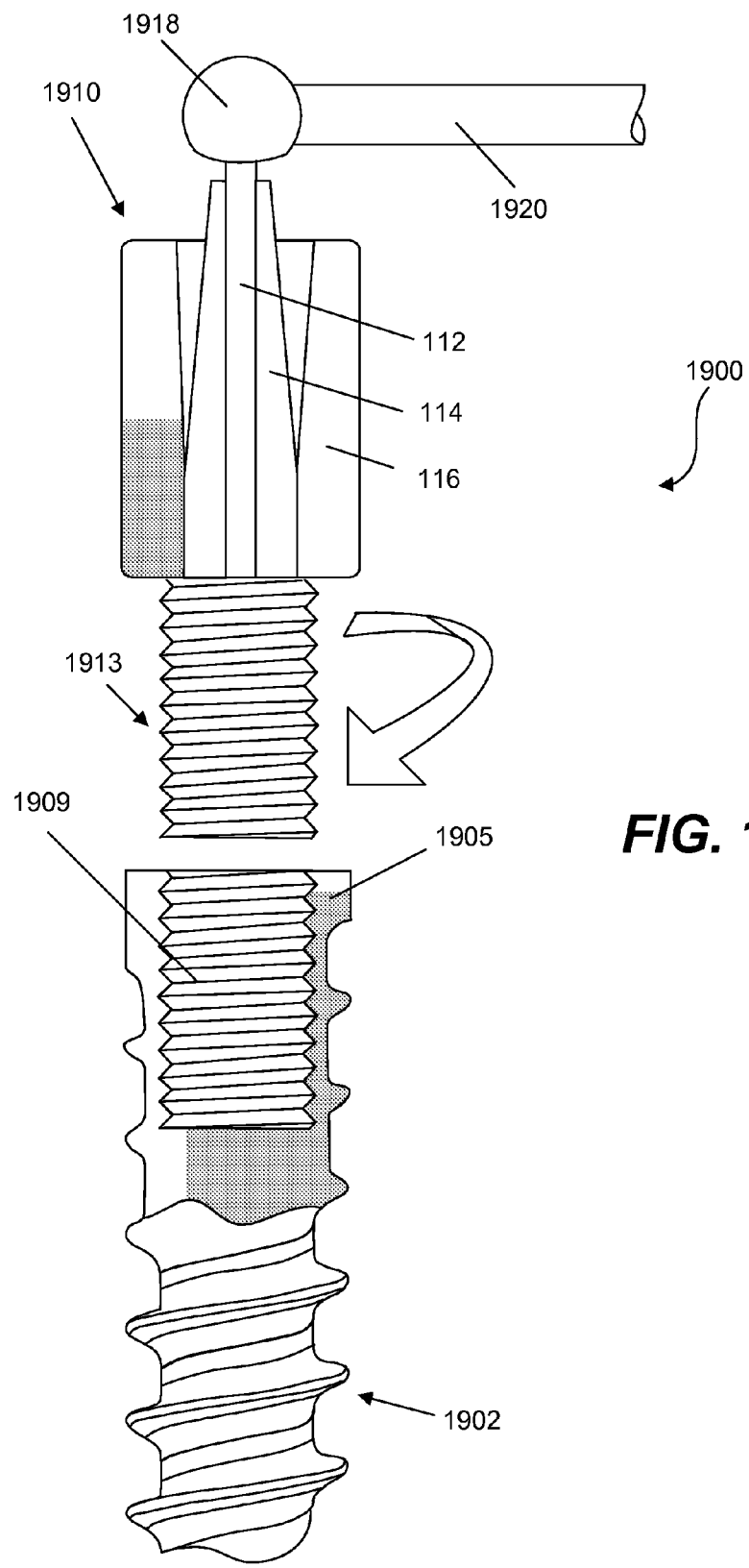
FIG. 19 is a lateral view of a further embodiment of a dynamic spine stabilization system in accordance with the present invention.

FIG. 19 illustrates a still further embodiment of a deflection rod system implant 1900 comprising an anchoring device 1902 with a cavity 1909 including inner threads for receiving an deflection rod system screw 1913, with complementary external threads extending from an deflection rod system 1910. The deflection rod system screw 1913 provides easy mating of the deflection rod system 1910 with the anchoring device 1902. The deflection rod system 1910 can further include a spherical (or semi-spherical) ball or joint 1918 that allows pivoting of a vertical rod 1920 connected with the deflection rod system 1910 so that the vertical rod 1920 can be oriented in a needed direction as the deflection rod system 1910 is rotated and the deflection rod system screw 1913 is seated within the cavity 1909. The vertical rod 1920 can then be pivoted into place extending between pedicles. The embodiment of FIG. 19 can simplify and shorten surgery by providing an easy technique for implanting the deflection rod system 1910.

Figure 20A:
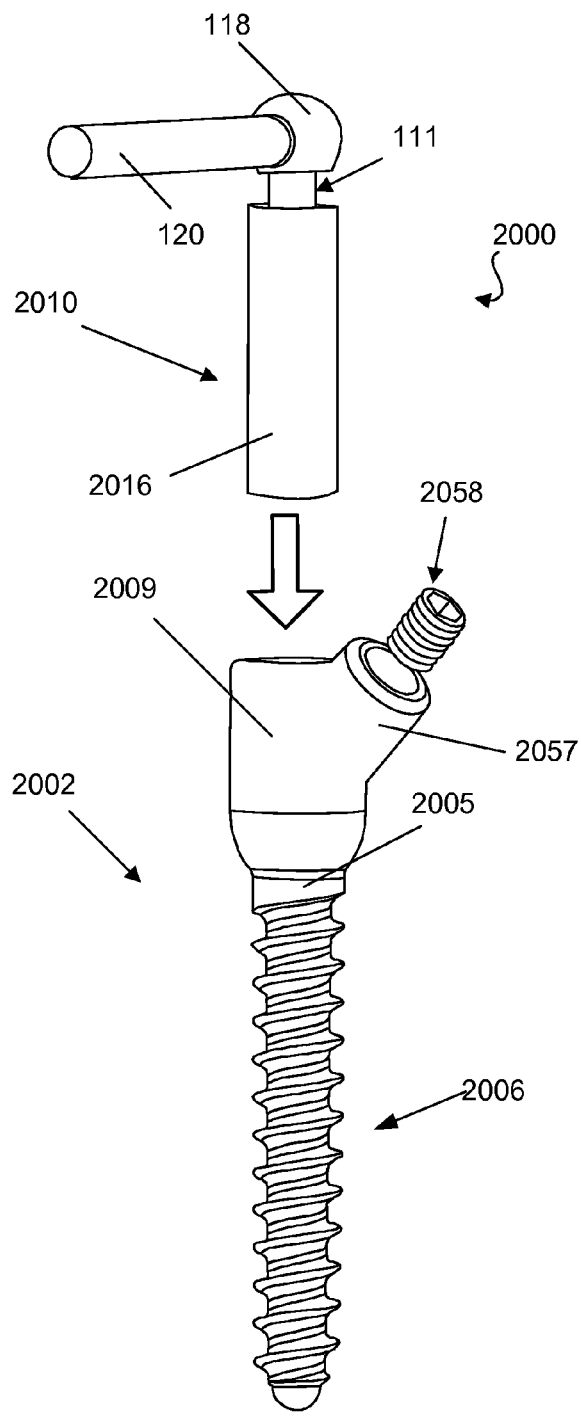
FIG. 20A is an exploded perspective view of yet another embodiment of a dynamic spine system in accordance with the present invention.
Figure 20B:
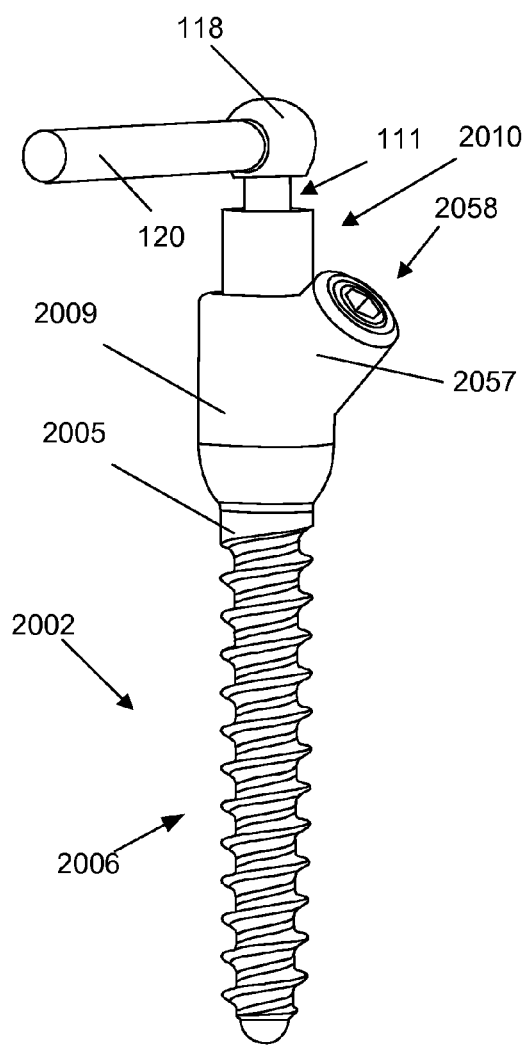
FIG. 20B is an perspective view the dynamic spin stabilization system of FIG. 20A with the distraction rod system and set screw seated within the anchoring device.

FIGS. 20A and 20B illustrate yet another embodiment of a deflection rod system implant 2000 in accordance with the present invention comprising an anchoring device 2002 with a housing 2009 for receiving a deflection rod system 2010. The embodiment resembles the deflection rod system implant 1700 of FIG. 17; however, housing 2009 is connected with the anchoring device 2002 at the shank 2005, but is not formed in the shank 2005. Depending on the outer diameter of the housing 2009 and the inner diameter of the cavity that receives the deflection rod system 2010, the housing 2009 permits use of one or both of (1) a threaded shaft 2006 having a smaller diameter (for example for use in smaller bones, such as in the cervical region) and (2) a deflection rod system 2010 comprising a deflection rod guide shield 2016 with a larger diameter (e.g., for use with thicker (and stiffer) deflection rods). As shown, the housing 2009 further comprises a threaded screw hole 2057 extending along an axis at an acute angle to the axis of the threaded shaft. The threaded screw hole 2057 receives a locking set screw 2058 that when seated (FIG. 20B) protrudes into the housing 2009 or against the deflection rod system 2010, where the deflection rod system 2010 is seated within the housing 2009. The locking set screw 2058 holds the deflection rod system 2018 in place within the housing 2009. In this embodiment, a deflection rod system 2010 can be selected to have an appropriate stiffness for the patient. Further, if several deflection rod system implants 2000 are used in a patient, each deflection rod system 2010, if desired, can have a different stiffness.

Figure 21:
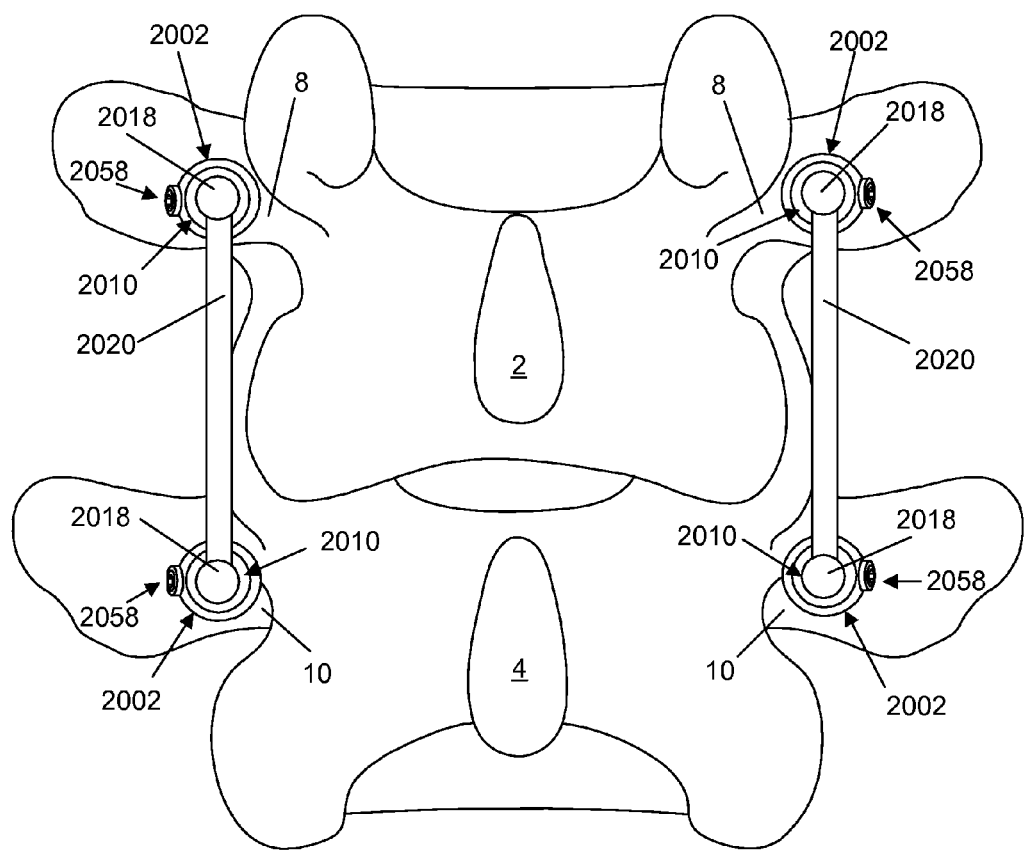
FIG. 21 is a posterior view of the dynamic spine stabilization system of FIG. 20A implanted and extending between a vertebra of the spine and two adjacent vertebrae.

FIG. 21 is a posterior view of the deflection rod system implant 2000 of FIGS. 20A and 20B implanted between pedicles 8,10 of adjacent vertebrae of a targeted motion segment. As shown, both ends of a vertical rod 2020 connected with the deflection rod system implant 2000 is connected with an deflection rod system 2010, in contrast to previous figures. Alternatively, one end of the vertical rod 2020 can be connected with an anchoring device such as described above, for example in FIG. 9. As will be appreciated, the deflection rod system implant 2000 has a small footprint from a posterior perspective.

Figure 22:
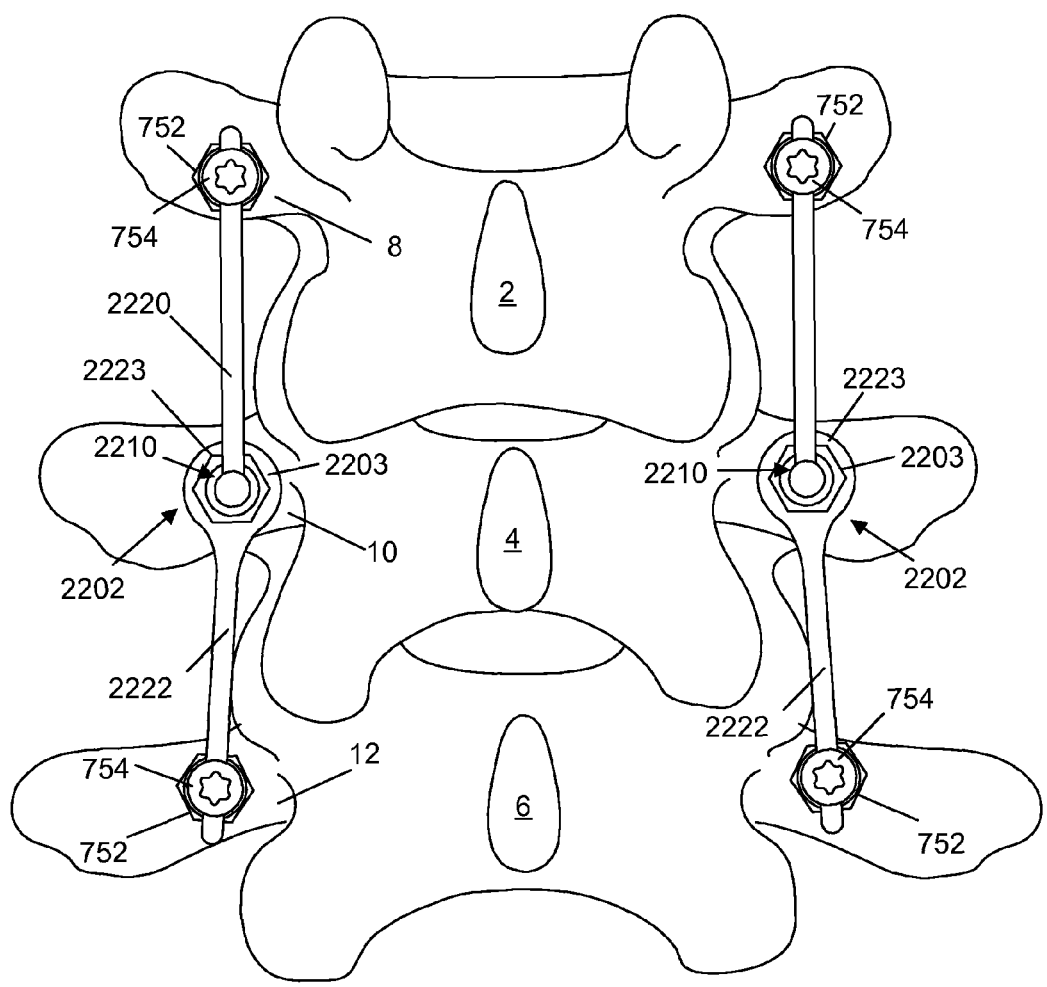
FIG. 22 is a posterior view of an alternative embodiment of a dynamic spine stabilization system in accordance with the present invention.

FIG. 22 is a posterior view of still another embodiment of a deflection rod system implant 2200 in accordance with the present invention adapted to support multiple motion segments. An anchoring device 2202 resembles the anchoring devices of FIGS. 17-20B and includes an outer wall 2203 having a hex portion for gripping using a torque wrench or other tool during implantation of the anchoring device 2202 in a bone. An anchoring device 2202 is secured to the two pedicles 10 of a vertebra common to the two motion segments to be supported. A vertical rod 2220 connected with an deflection rod system 2210 mated with the anchoring device 2202, extends between the vertebra and an upper vertebra of the upper motion segment, and is connected to a pedicle 8 of the segment by an upper anchoring device 752. As above, the vertical rod 2220 is connected to the deflection rod and can deflect the deflection rod in response to relative movement of two vertebrae between which the vertical rod 2220 extends. Another vertical rod 2222 includes a yolk 2223 resembling a box-end wrench with a shape generally complementing the hex pattern of the outer wall of the bone anchor. The yolk 2223 is received over the outer wall 2203 of the anchoring device 2202, and can resist rotation the vertical rod 2222 relative to the anchoring device 2202. The vertical rod 2222 extends to the lower vertebra of the lower motion segment, and is connected to a pedicle 12 of the motion segment by a lower anchoring device 752. The vertical rod 2222 can resist movement between vertebrae 4 and 6, and thus supplement or substitute for other fusion devices, for example.

Figure 23:
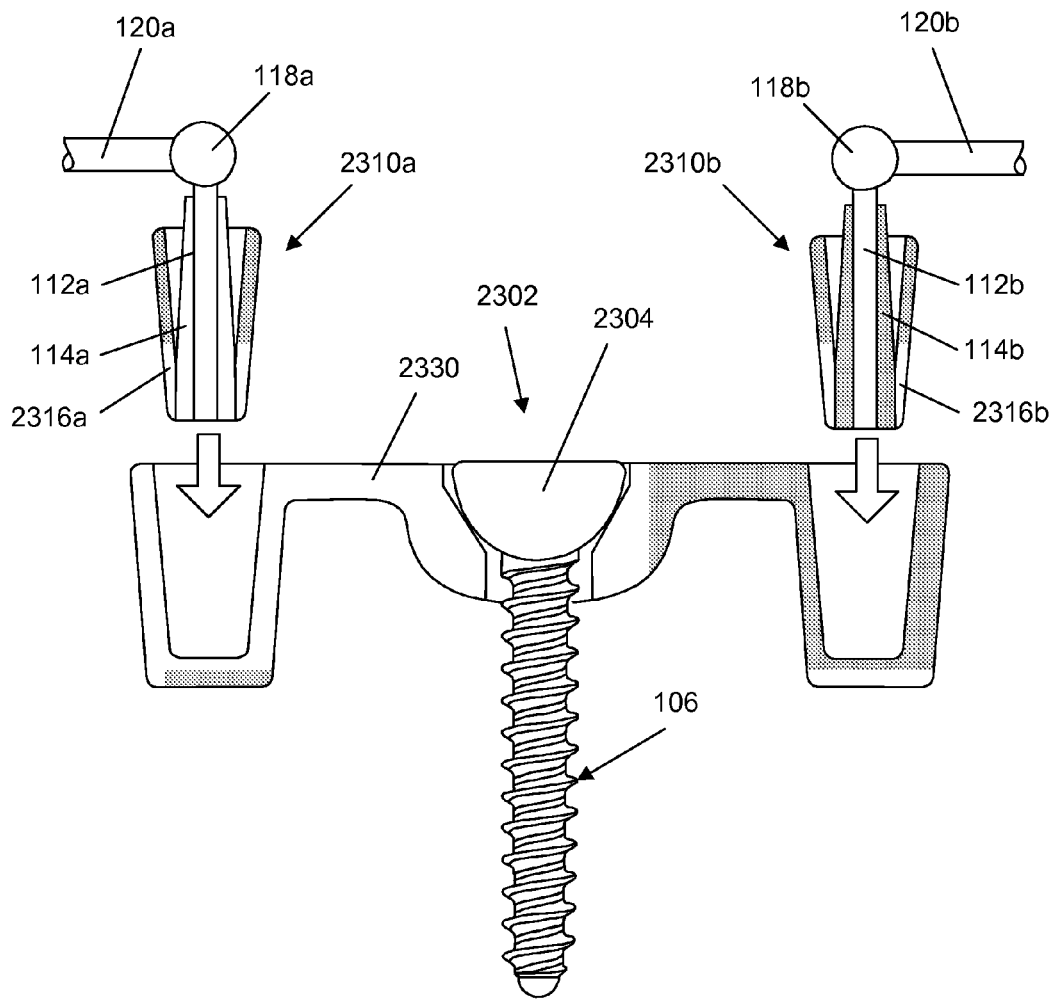
FIG. 23 is a lateral view (in partial cross-section) of an alternative embodiment of a dynamic spine stabilization system in accordance with the present invention.

FIG. 23 is a lateral view (in partial cross-section) of an alternative embodiment of a deflection rod system implant 2300 for use with dynamic stabilization systems in accordance with the present invention and adapted to dynamically support multiple motion segments of the spine. The deflection rod system implant 2300 resembles the deflection rod system implant 1100 of FIG. 11A, but includes deflection rod systems generally oriented in an anterior-to-posterior direction. The deflection rod system implant 2300 is adapted to support multiple motion segments and comprises a first deflection rod system 2310a connected with a vertical rod 120a extending cranially, a second deflection rod system 2310b connected with a vertical rod 120b extending caudally, and an anchoring device 2302. The first and second deflection rod systems 2310a, 2310b can have similar or different bending characteristics, as prescribed by the surgeon or a physician. A common arm 2330 connects the first and second deflection rod systems 2310a, 2310b with the anchoring device 2302. The orientation of the deflection rod systems 2310a, 2310b can reduce the moment force that tends to cause rotation of the arm 2330; however, in other embodiments it may be desirable to include a head capable of receiving a horizontal rod to further resist moment force. In this embodiment, the deflection rod systems 2310a, 2310b are substantially parallel.

Figure 7C:
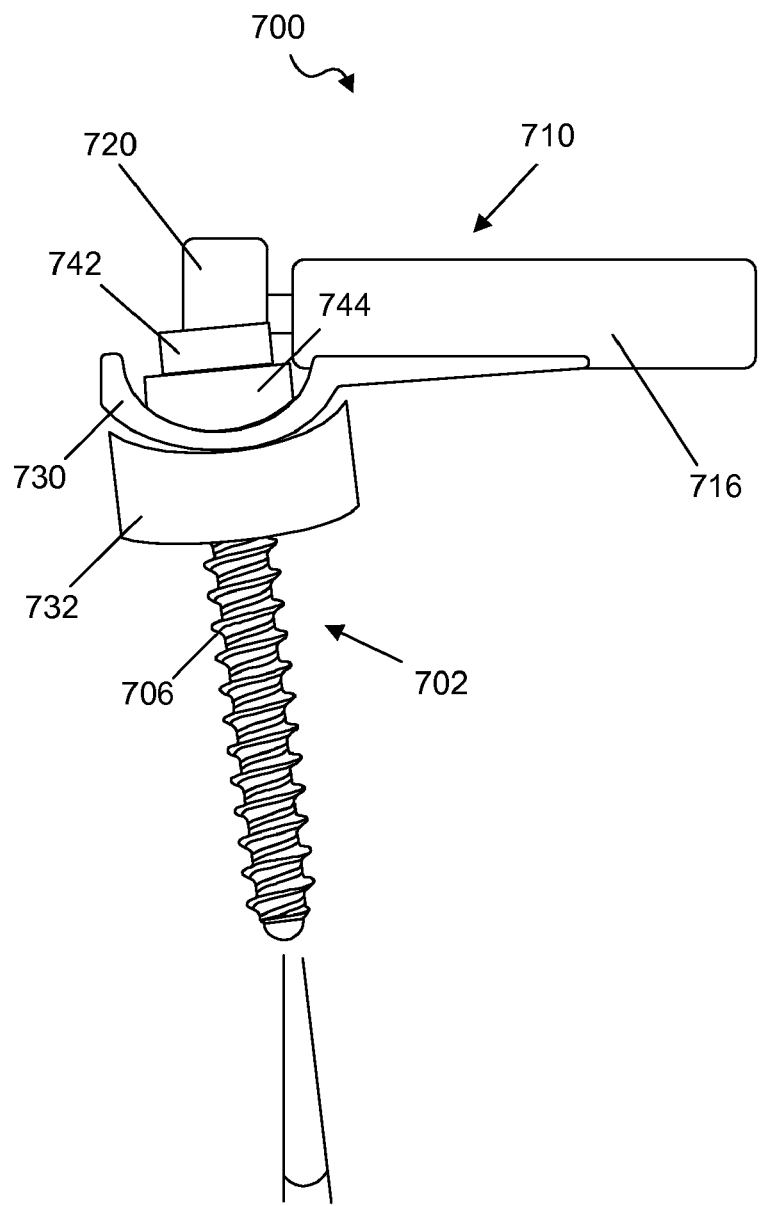
FIG. 7C is a caudal view of the dynamic spine stabilization system of FIG. 7A.
Figure 24A:
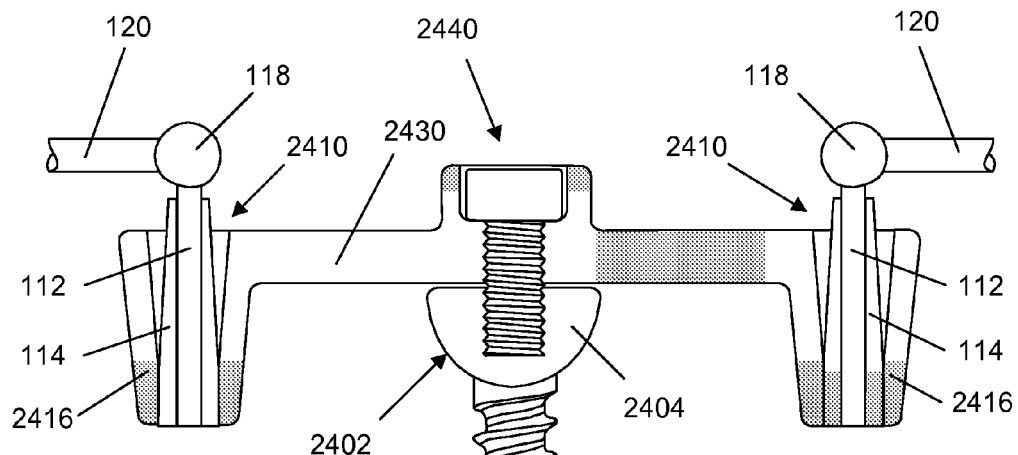
FIG. 24A is a lateral view (in partial cross-section) of an alternative embodiment of a dynamic spine stabilization system in accordance with the present invention.
Figure 24B:
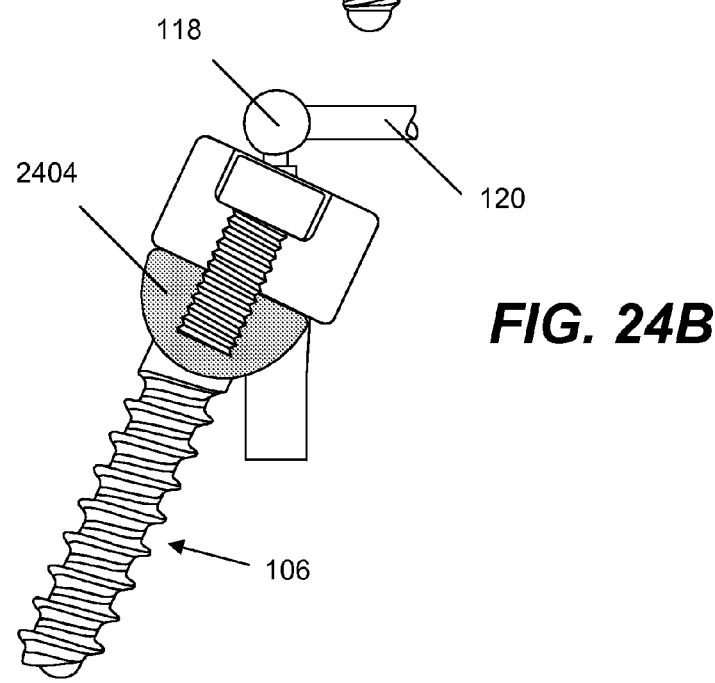
FIG. 24B is a lateral view of the dynamic spine stabilization system of FIG. 24A.

FIG. 24A is a lateral view (in partial cross-section) and FIG. 24B is a cranial view (in partial cross-section) of still another embodiment of a deflection rod system implant 2400 for use with dynamic stabilization systems accordance with the present invention and adapted to dynamically support multiple motion segments is shown. The deflection rod system implant 2400 resembles the deflection rod system implant 2300 of FIG. 23. An arm 2430 that is mated with the anchoring device 2402 after the anchoring device 2402 has been implanted within a bone. The arm 2430 receives a locking screw 2440 having threads that complement threads of a screw hole within the head 2404 of the anchoring device 2402. The locking screw 2440 fixedly connects the arm 2430 to the anchoring device 2402 when the locking screw 2440 is seated within the head 2404. The embodiment also includes a distraction rod guide or shield 2416 integrally formed with the arm 2430. In this embodiment, the deflection rod systems 2410 are substantially parallel. As seen in FIGS. 24A, 24B the arm 2430 can connect to the head 2404 in a number of orientations. This can be accomplished with an arm 2430 with a convex surface that mates with a concave surface of the head 2404 as shown, by way of example only, as depicted in FIG. 7C.

Figure 25:
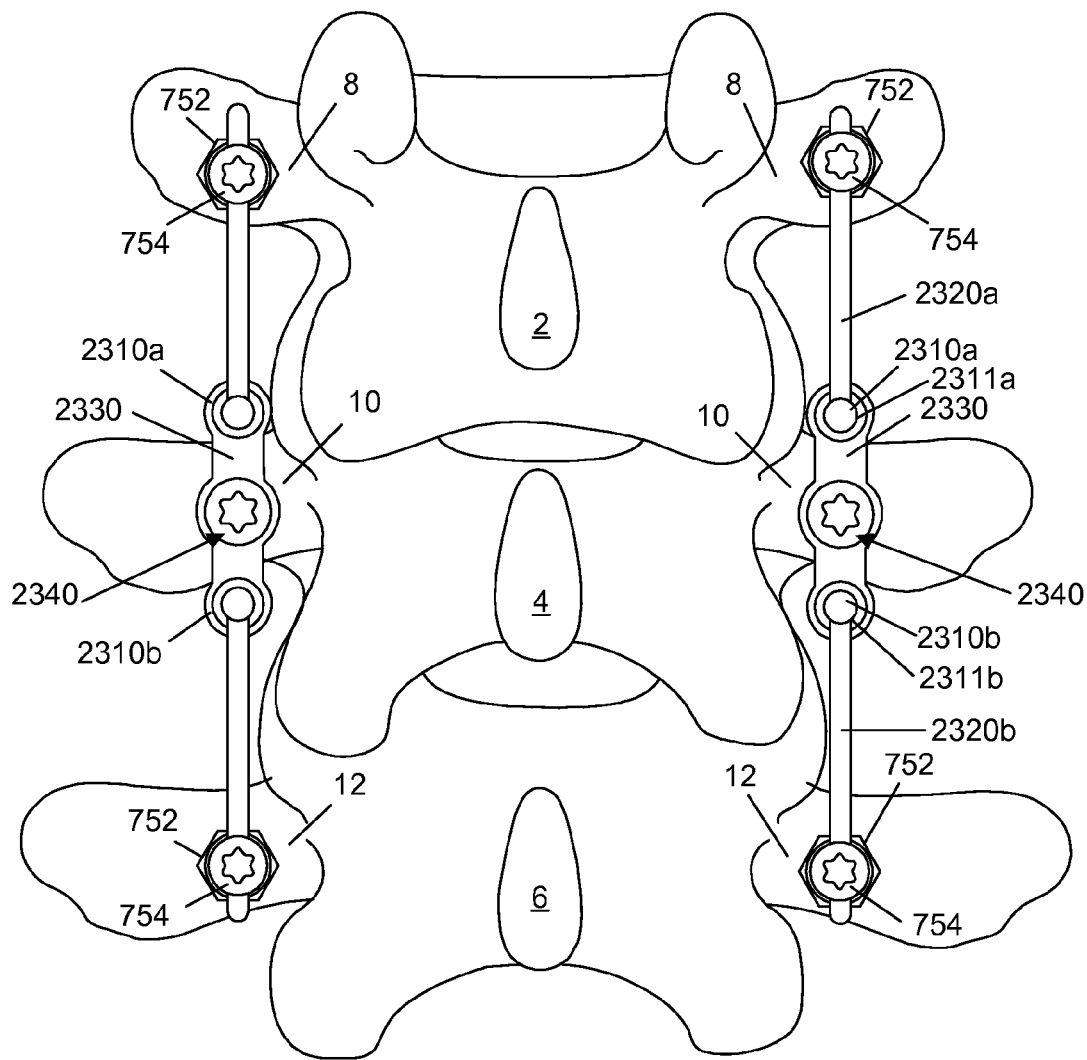
FIG. 25 is a posterior view of the dynamic spine stabilization system of FIG. 24A implanted and extending between a vertebra of the spine and two adjacent vertebrae.

FIG. 25 is a posterior view of the deflection rod system implant 2300 of FIG. 23 comprising the first deflection rod system 2310a and second deflection rod system 2310b secured to a vertebra common to two adjacent motion segments or vertebrae targeted for stabilization by an anchoring device. A first vertical rod 2320a is connected to a deflection rod 2311a of the first deflection rod system 2310a and extends cranially to the upper vertebra of the upper targeted motion segment, and is secured to the upper vertebra by an upper anchoring device 752. A second vertical rod 2320b is connected to a deflection rod 2311b of the second deflection rod system 2310b and extends caudally to the lower vertebra of the lower targeted motion segment, and is secured to the lower vertebra by a lower anchoring device 752. The vertical rods 2320a, 2310b deflect respective deflection rods 2311a, 2311b in response to relative movement of the two vertebrae between which the vertical rods 2320a, 2320b extend.

Figure 26:
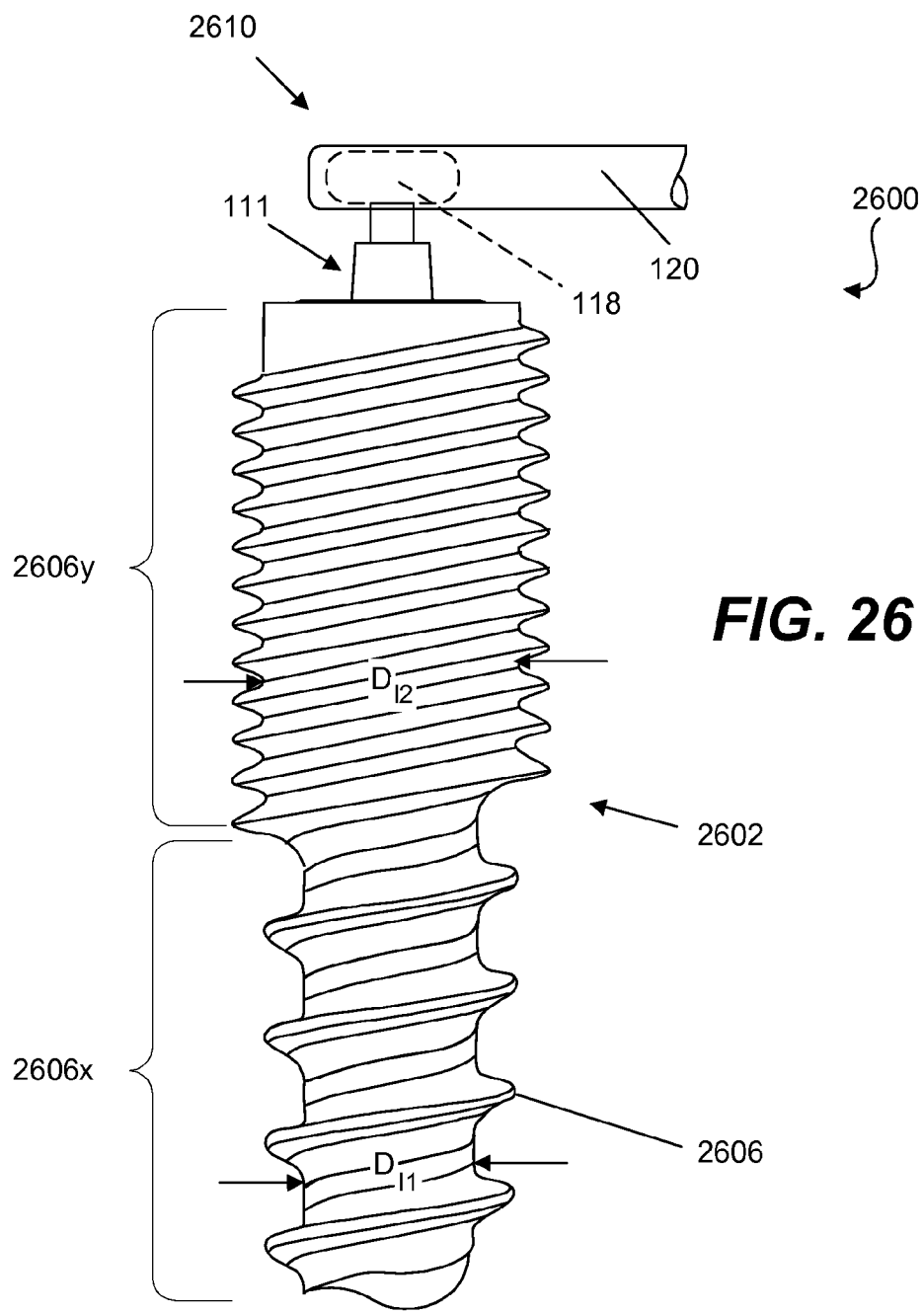
FIG. 26 is a lateral view of a further embodiment of a dynamic spine stabilization system in accordance with the present invention.

FIG. 26 illustrates an embodiment of a deflection rod system implant 2600 comprising an anchoring device 2602 with a cavity 2609 for receiving a deflection rod system 2610. As mentioned above, it has been observed that acceptable anchoring can be achieved in a bone such as a pedicle using a thread 2606 pattern that include deep threads 2606y and shallow threads 2606x. The anchoring device 2602 can have a length such that when implanted a portion of the anchoring device 2602 further from the deflection rod system 2610 is seated within cancellous bone while a portion of the anchoring device 2602 nearer the deflection rod system 2610 is seated within cortical bone. Screw threads 2606x having a high pitch (i.e., having a comparatively large gap between threads) and deep threads are usable with satisfactory results in cancellous bone, which bone is an osseous tissue with a low density strength but high surface area. Screw threads 2606y having a low pitch and shallow threads are usable with satisfactory results in cortical bone, which bone is an osseous tissue with a high density strength. The diameter, $D_{12}$, of the anchoring device shaft can be expanded along a portion of the shaft that is seated within the cortical bone and/or a portion of the shaft that accommodates the deflection rod system 2610. Expanding the diameter of the shaft can allow the threads to cut new thread patterns within the cortical bone, and can accommodate a deflection rod system 2610 (or range of deflection rod systems) having a larger diameter. Further, the diameter of the shaft can be larger where the cortical threads are shallow, as the vertebral bone is thicker in this area. For the same reason, the corresponding diameter of the bone as shown in FIG. 27 can be larger.

Figure 27:
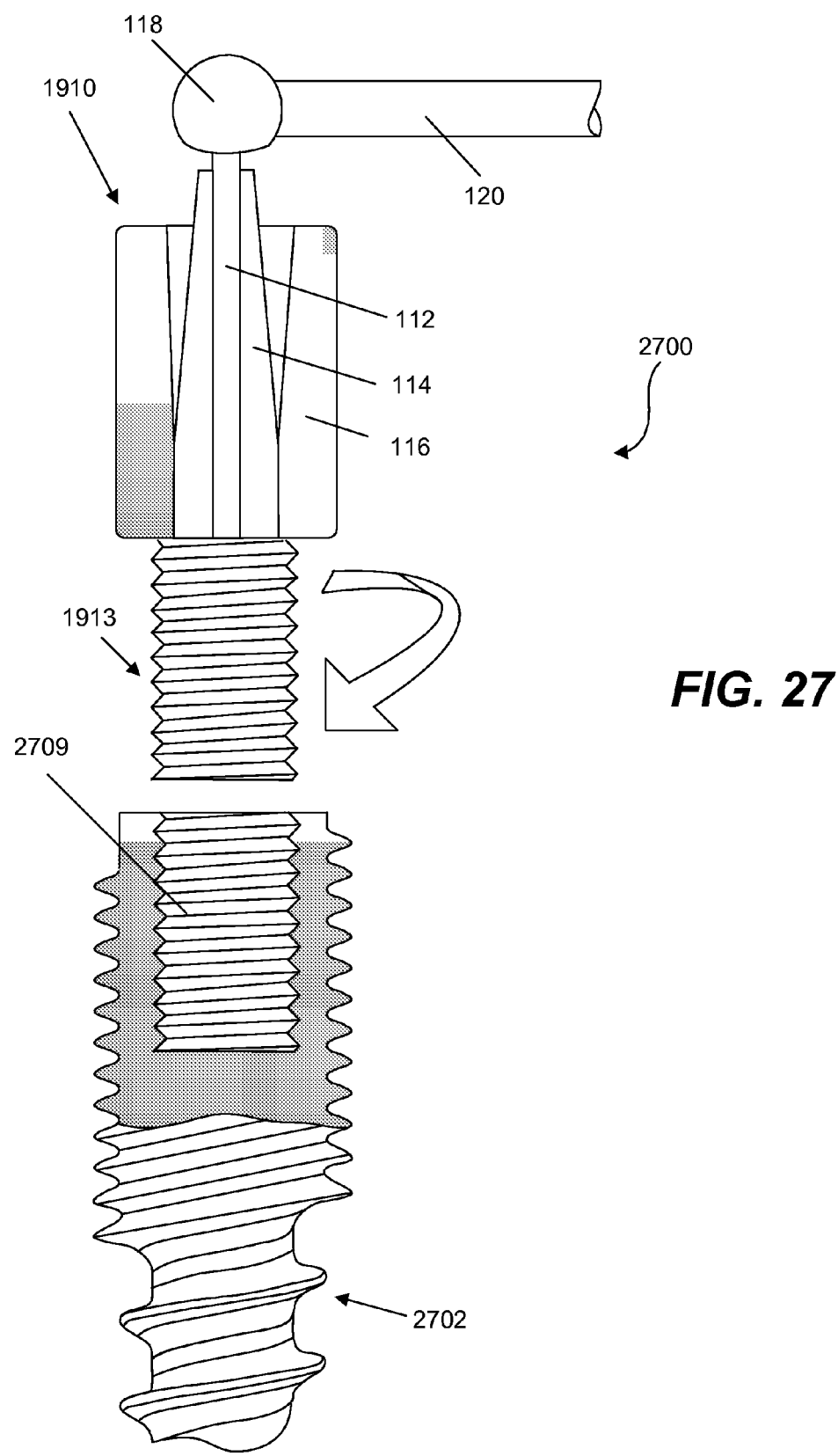
FIG. 27 is a lateral view of yet another embodiment of a dynamic spine stabilization system in accordance with the present invention.

FIG. 27 illustrates a still further embodiment of a deflection rod system implant 2700 comprising an anchoring device 2702 including an external thread pattern resembling the external thread pattern of FIG. 26, and further including a cavity 2709 with inner threads for receiving an deflection rod system screw 1913, with complementary external threads extending from an deflection rod system 1910. The deflection rod system screw 1913 provides easy mating of the deflection rod system 1910 with the anchoring device 1902. The deflection rod system 1910 can further include a spherical (or semi-spherical) ball or joint 1918 that allows pivoting of a vertical rod 1920 connected with the deflection rod system 1910 so that the vertical rod 1920 can be oriented in a needed direction as the deflection rod system 1910 is rotated and the deflection rod system screw 1913 is seated within the cavity 1909. The vertical rod 1920 can then be pivoted into place extending between pedicles.

Figure 28:
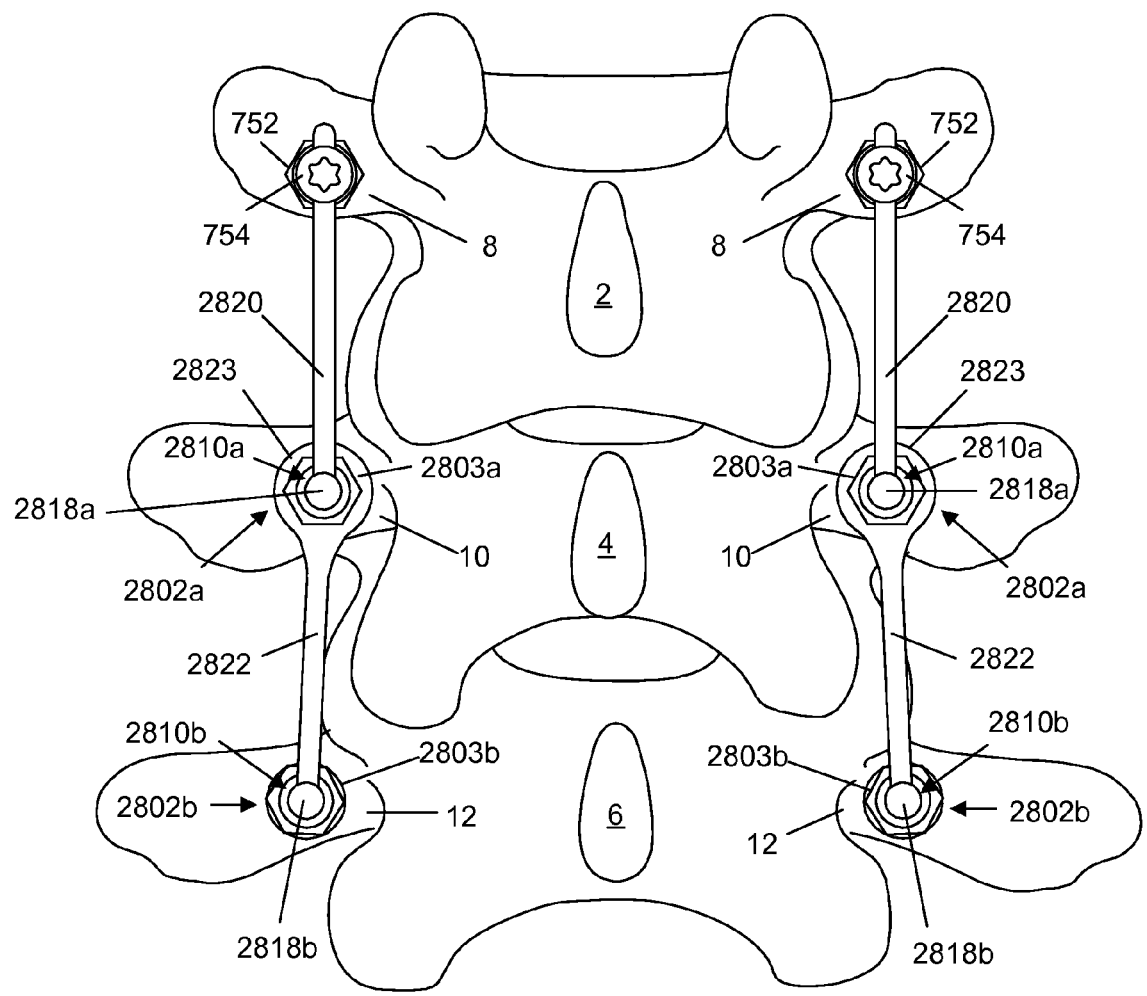
FIG. 28 is a posterior view of an alternative embodiment of a dynamic spine stabilization system in accordance with the present invention.

Referring again to FIG. 22, multiple motion segments can be stabilized by stringing together vertical rods and deflection rod systems individually selected for the corresponding motion segment. As shown in FIG. 22, the yoke 2223 of a vertical rod 2222 is fitted over the outer wall 2203 of a deflection rod system 2210. An opposite end of the vertical rod 2222 is connected to an anchoring device 2202. However, in still other embodiment (as shown in FIG. 28), the vertical rod 2822 can be connected with a second deflection rod system 2810b anchored by an anchoring device 2802b to a pedicle 12 of a lower vertebra of the motion segment. The deflection rod system 2810b allows controlled relative movement of the two vertebrae. Systems and methods in accordance with the present invention can comprise a series of implants connected with, and selected for the corresponding motion segment. The implants can comprise vertical rods rigidly connected between vertebrae as shown in FIG. 22 (for example to support fusion), or alternatively the vertical rods can be dynamically connected between vertebrae by a deflection rod system as shown in FIG. 28. Any combination of implants can be used having a stiffness selected for the respective motion segment. For example, FIG. 29 illustrates dynamic stabilization of three motion segments with two yoked vertical rods 2922a, 2922b fitted over dynamic stabilization systems 2810a, 2810b anchored at an upper vertebra of the targeted segment.

Figure 29:
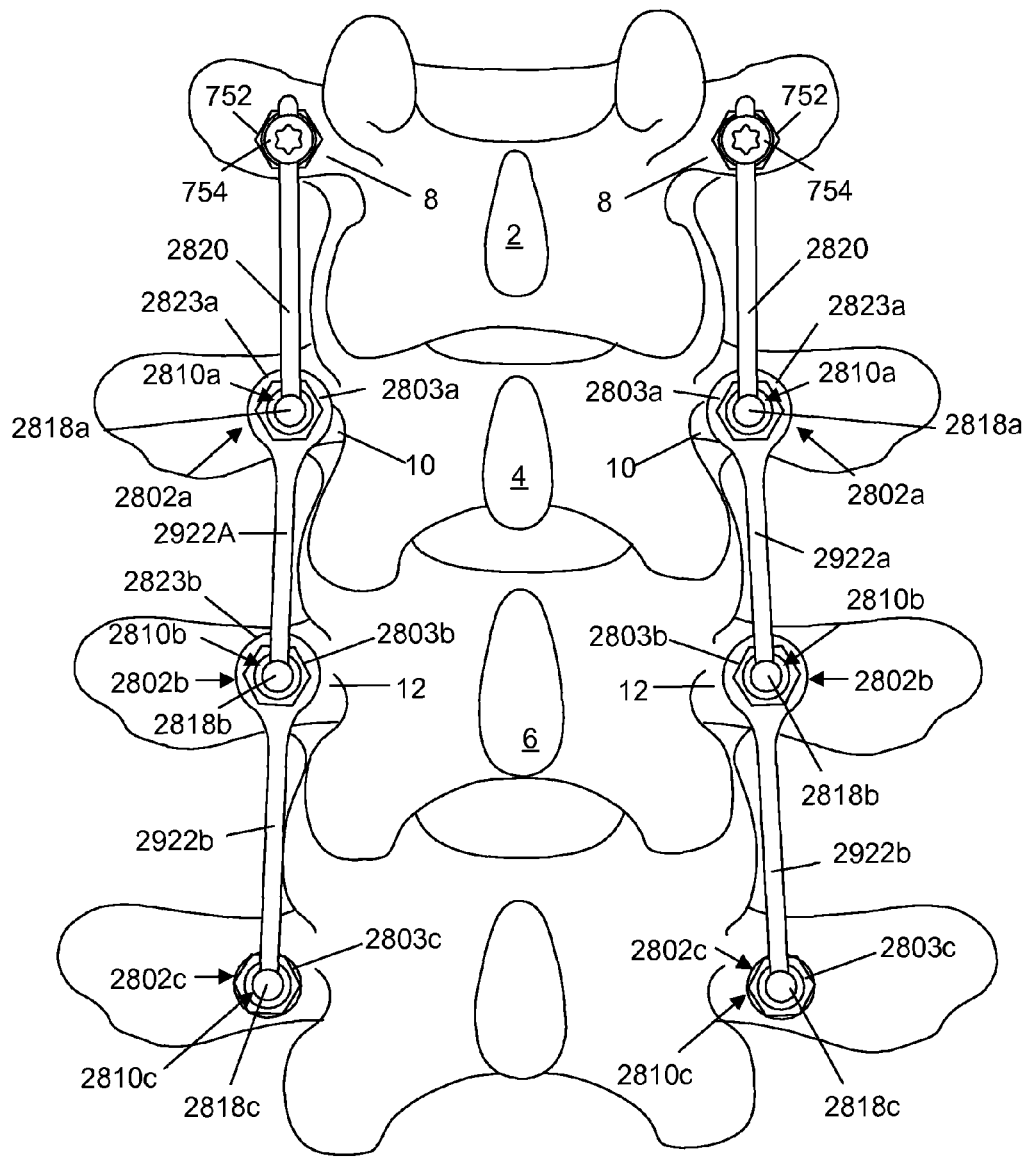
FIG. 29 is a posterior view of an alternative embodiment of a dynamic spine stabilization system in accordance with the present invention.

While the vertical rods 2822, 2922 of FIGS. 28 and 29 are shown to be connected with dynamic stabilization systems implanted in respective pedicles, embodiments of systems and methods can comprise vertical rods that are connected with dynamic stabilization systems after implantation of dynamic stabilization systems. The vertical rods 2822, 2922 can be attachable with a dynamic stabilization system at or near the connection with the spherical ball joint. Such an arrangement can allow a yoke of a vertical rod to be placed over and around the outer wall of a dynamic stabilization system (or simply past the spherical ball joint in a staging position for further adjustment) without interference from the vertical rod of that dynamic stabilization system.

It is proposed that a preferred embodiment may have the following preferred dimensions, although dimension can vary substantially based on a number of performance factors.
- Inner rod having a diameter of about 0.080 inches.
- Outer shell having a major diameter of about 165 inches and the tapered portion tapers at about 2.5 degrees per side.
- Shield and deflection guide having a housing diameter of about 0.265 inches.
- The deflection rod is secured to the deflection guide along a length of about 0.200 inches from the end of the deflection rod system.
- The deflection rod system has a working length from the end of the system to the center of the ball joint of about 1.040 less the press fit length of about 0.200 which is length of about 0.840.

The overall length of the deflection rod system is about 1.100 inches.

The spherical ball in the ball and socket joint that secures the vertical rod to the deflection rod system has a diameter of about 188 inches.

The vertical rod has a diameter of about 0.150 inches.

Materials of Embodiments of the Invention:

In addition to Nitinol or nickel-titanium (NiTi) other super elastic materials include copper-zinc-aluminum and copper-aluminum-nickel. However for biocompatibility the nickel-titanium is the preferred material.

As desired, the implant can, in part, be made of titanium or stainless steel. Other suitable material includes by way of example only polyetheretherketone (PEEK), polyetherketoneketone (PEKK), polyetherketone (PEK), polyetherketoneetherketoneketone (PEKEKK), and polyetheretherketoneketone (PEEKK). Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention.

Reference to appropriate polymers that can be used in the spacer can be made to the following documents. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials."

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A deflection rod system adapted to be mounted to a bone anchor implanted in a spine, the deflection rod system comprising:
    a shield having a shield cavity having a shield cavity axis;
    a deflectable rod having a proximal end and a distal end, the deflectable rod being disposed in the shield cavity aligned with the shield cavity axis such that the proximal end extends out of the shield cavity and the distal end is connected to said shield;
    wherein a proximal portion of the deflectable rod is spaced from the shield within the shield cavity such that the proximal portion of the deflection rod can deflect within said shield cavity transverse to the shield cavity axis thereby permitting the proximal end of the deflection rod to deflect;
    a connector rod that is attached to said proximal end of said deflectable rod with a connector; and
    a mount connected to said shield that mounts said deflection rod system relative to said bone anchor in one of a plurality of positions.

2. The deflection rod system of claim 1 wherein said connector is adapted to be mounted in-line with the bone anchor so as to minimize any torque that said connector rod can place on the bone anchor.

3. The deflection rod system of claim 1 wherein the bone anchor includes a bone anchor head and said mount is adapted to mount said deflection rod system relative to said bone anchor head in one said plurality of positions.

4. The deflection rod system of claim 1 wherein the bone anchor includes a curved anchor surface and wherein said mount includes a curved mount surface adapted to be mated with the curved anchor surface with the curved mount surface moveable relative to said curved anchor surface.

5. The deflection rod system of claim 1 wherein said deflectable rod includes an inner rod and an outer shell positioned about said inner rod.

6. The deflection rod system of claim 1 wherein said deflectable rod comprises a super elastic material.

7. The deflection rod system of claim 1 wherein said connector permits movement between said connector rod and said deflectable rod.

8. The deflection rod system of claim 1 wherein said mount mounts said deflection rod system such that the shield cavity axis is oriented about transverse to the bone anchor.

9. The deflection rod system of claim 1 wherein said mount mounts said deflectable rod about perpendicular to said connector in a first position and said mount allows said connector and said deflectable rod to move relative to each other from said first position.

10. The deflection rod system of claim 5 wherein said inner rod has a proximal end that extends from said outer shell and from said shield, and said connector is connected to said proximal end of said inner rod.

11. A deflection rod system adapted to be mounted to a bone anchor which is implanted in a spine wherein the deflection rod system comprises:
    a shield having a shield cavity having a shield cavity axis;
    a deflectable rod having a proximal end and a distal end, the deflectable rod being disposed in the shield cavity aligned with the shield cavity axis such that the proximal end extends out of the shield cavity and the distal end is connected to said shield;
    wherein a proximal portion of the deflectable rod is spaced from the shield within the shield cavity such that the proximal portion of the deflection rod can deflect within said shield cavity transverse to the shield cavity axis thereby permitting the proximal end of the deflection rod to deflect;
    a connector rod that is attached to said proximal end of said deflectable rod with a connector;
    said shield including a mount that is adapted to mount to said deflection rod relative to the bone anchor in one of a plurality of positions; and
    wherein the bone anchor includes a curved anchor surface and wherein said mount includes a curved mount surface adapted to be mated with the curved anchor surface with the curved mount surface moveable relative to said curved anchor surface.

12. The deflection rod system of claim 11 wherein said connector is adapted to be mounted in-line with the bone anchor so as to minimize any torque that said connector rod can place on the bone anchor.

13. The deflection rod system of claim 11 wherein said mount is adapted to mount said deflection rod system about transverse to the bone anchor.

14. The deflection rod system of claim 11 wherein said deflectable rod includes an inner rod and an outer shell positioned about said inner rod.

15. The deflection rod system of claim 11 wherein said deflectable rod comprises a super elastic material.

16. The deflection rod system of claim 11 wherein said connector is a ball and socket connector and said ball and socket connector is adapted to be positioned in-line with the bone anchor.

17. A deflection rod system adapted to be mounted to a bone anchor implanted in a spine, the deflection rod system comprising:
　a shield having a shield cavity having a shield cavity axis;
　a deflectable rod having a proximal end and a distal end, the deflectable rod being disposed in the shield cavity aligned with the shield cavity axis such that the proximal end extends out of the shield cavity and the distal end is connected to said shield;
　wherein a proximal portion of the deflectable rod is spaced from the shield within the shield cavity such that the proximal portion of the deflection rod can deflect within said shield cavity transverse to the shield cavity axis thereby permitting the proximal end of the deflection rod to deflect;
　a connector rod that is attached to said proximal end of said deflectable rod with a connector;
　a mount connected to said shield that is adapted to mount said deflection rod system relative to a bone anchor in one of a plurality of positions;
　wherein said bone anchor includes a curved anchor surface and said mount includes a curved mount surface adapted to mate with the curved anchor surface with the curved mount surface moveable relative to said curved anchor surface;
　wherein said connector is adapted to be mounted in-line with the bone anchor so as to minimize any torque that said connector rod can place on the bone anchor; and
　wherein said mount is adapted to mount said deflection rod system such that the shield cavity axis is about transverse to the bone anchor.

18. The deflection rod system of claim 17, wherein said deflectable rod includes an inner rod and an outer shell positioned about said inner rod, and said inner rod comprises a super elastic material.

19. The deflection rod system of claim 17, wherein said connector is a ball and socket connector, and said ball and socket connector is positioned in-line with the bone anchor.

20. The deflection rod system of claim 17, wherein said connector permits movement between said connector rod and said deflectable rod.

* * * * *